(12) United States Patent
Papy-Garcia et al.

(10) Patent No.: US 10,324,096 B2
(45) Date of Patent: Jun. 18, 2019

(54) METHOD OF DIAGNOSIS, PROGNOSTIC OR TREATMENT OF NEURODEGENERATIVE DISEASE

(71) Applicants: CENTRE NATIONAL DE LA RECHERCHE SCIENTIFIQUE, Paris (FR); UNIVERSITE PARIS-EST CRETEIL VAL DE MARNE, Creteil (FR); UNIVERSITE PIERRE ET MARIE CURIE (PARIS 6), Paris (FR); ICM - INSTITUT DU CERVEAU ET DE LA MOELLE EPINIERE, Paris (FR); OTR3, Paris (FR); ASSISTANCE PUBLIQUE-HOPITAUX DE PARIS, Paris (FR)

(72) Inventors: Dulce Papy-Garcia, Chily Mazarin (FR); Minh Bao Huynh, Vitry sur Seine (FR); Nadia Soussi-Yanicostas, Paris (FR); Rita Vozari, Paris (FR); Fernando Sineriz, Montigny les Bretonneux (FR); Constantin Yanicostas, Paris (FR)

(73) Assignees: CENTRE NATIONAL DE LA RECHERCHE SCIENTIFIQUE, Paris (FR); UNIVERSITE PARIS-EST CRETEIL VAL DE MARNE, Creteil (FR); SORBONNE UNIVERSITÉ, Paris (FR); ICM-INSTITUT DU CERVEAU ET DE LA MOELLE EPINIERE, Paris (FR); OTR3, Paris (FR); ASSISTANCE PUBLIQUE-HOPITAUX DE PARIS, Paris (FR)

( * ) Notice: Subject to any disclaimer, the term of this patent is extended or adjusted under 35 U.S.C. 154(b) by 0 days.

(21) Appl. No.: 15/196,180

(22) Filed: Jun. 29, 2016

(65) Prior Publication Data

US 2016/0334421 A1    Nov. 17, 2016

Related U.S. Application Data

(62) Division of application No. 14/351,616, filed as application No. PCT/EP2012/070435 on Oct. 15, 2012, now abandoned.

(60) Provisional application No. 61/547,226, filed on Oct. 14, 2011.

(30) Foreign Application Priority Data

Apr. 6, 2012   (EP) .................................... 12305414

(51) Int. Cl.
| | | |
|---|---|---|
| *G01N 33/68* | (2006.01) | |
| *C12Q 1/68* | (2018.01) | |
| *A61K 31/70* | (2006.01) | |
| *A61K 31/737* | (2006.01) | |
| *A61K 31/713* | (2006.01) | |
| *C12Q 1/6886* | (2018.01) | |
| *C12N 15/113* | (2010.01) | |
| *A61K 31/727* | (2006.01) | |
| *A61K 38/17* | (2006.01) | |
| *C12Q 1/686* | (2018.01) | |
| *G01N 33/53* | (2006.01) | |
| *A61K 31/721* | (2006.01) | |
| *C12Q 1/6883* | (2018.01) | |
| *C07H 21/02* | (2006.01) | |

(52) U.S. Cl.
CPC ......... *G01N 33/6896* (2013.01); *A61K 31/70* (2013.01); *A61K 31/713* (2013.01); *A61K 31/721* (2013.01); *A61K 31/727* (2013.01); *A61K 31/737* (2013.01); *A61K 38/1703* (2013.01); *A61K 38/1709* (2013.01); *C12N 15/1137* (2013.01); *C12Q 1/686* (2013.01); *C12Q 1/6883* (2013.01); *C12Q 1/6886* (2013.01); *C12Y 208/02023* (2013.01); *C12Y 208/02029* (2013.01); *G01N 33/5308* (2013.01); *C12N 2310/14* (2013.01); *C12N 2310/3233* (2013.01); *C12N 2320/30* (2013.01); *C12Q 2600/118* (2013.01); *C12Q 2600/136* (2013.01); *C12Q 2600/158* (2013.01); *G01N 2333/47* (2013.01); *G01N 2333/91194* (2013.01); *G01N 2440/14* (2013.01); *G01N 2500/20* (2013.01); *G01N 2800/28* (2013.01); *G01N 2800/2821* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,180,715 A | 1/1993 | Parsons |
| 8,476,220 B2 | 7/2013 | Barritault et al. |
| 2010/0048638 A1 | 2/2010 | Crawford et al. |

FOREIGN PATENT DOCUMENTS

| | | |
|---|---|---|
| JP | 2000-065837 A | 3/2000 |
| JP | 2009-525039 A | 7/2009 |
| JP | 2010-537200 A | 12/2010 |

(Continued)

OTHER PUBLICATIONS

Peters et al., European Heart Journal, vol. 29:324-331, 2008.
(Continued)

*Primary Examiner* — Sean McGarry
(74) *Attorney, Agent, or Firm* — Young & Thompson

(57) ABSTRACT

Methods for the diagnosis and prognosis of neurodegenerative diseases, such as Alzheimer's disease, are described. Compositions and method for the treatment of neurodegenerative diseases are also described.

4 Claims, 34 Drawing Sheets

Specification includes a Sequence Listing.

(56) References Cited

FOREIGN PATENT DOCUMENTS

| WO | 0005270 | 2/2000 |
|---|---|---|
| WO | 0069444 | 11/2000 |
| WO | 02/41842 A2 | 5/2002 |

OTHER PUBLICATIONS

Fitton, Mar. Drugs, vol. 9:1731-1760, 2011.
Samama et al., New England Journal of Medicine, vol. 341 (11): 793-800, 1999.
Bruinsma et al., "Sulfation of heparan sulfate associated with amyloid-β plaques in patients with Alzheimer's disease", Acta Neuropathol, 2010, vol. 119, pp. 211-220.
Gandhi et al., "Heparin/heparan sulphate-based drugs", Drug Discovery Today, 2010, vol. 15, Nos. 23/24, pp. 1058-1069.
Goedert et al., "Assembly of microtubule-associated protein tau into Alzheimer-like filaments induced by sulphated glycosaminoglycans", Nature, 1996, vol. 383, pp. 550-553.
Hampel et al., "Total and phosphorylated tau protein as biological markers of Alzheimer's disease", Experimental Gerontology, 2010, vol. 45, pp. 30-40.
Ishiguro et al., "Phosphorylated tau in human cerebrospinal fluid is a diagnostic marker for Alzheimer's disease", Neuroscience Letters, 1999, vol. 270, pp. 91-94.
Lawrence et al., "The principal neuronal gD-type 3-O-sulfotransferases and their products in central and peripheral nervous system tissues", Matrix Biology, 2007, vol. 26, pp. 442-455.
Malavaki et al., "Heparan sulfate: biological significance, tools for biochemical analysis and structural characterization", Biomedical Chromatography, 2011, vol. 25, pp. 11-20.
Paquet et al., "A zebrafish model of tauopathy allows in vivo imaging of neuronal cell death and drug evaluation", The Journal of Clinical Investigation, 2009, vol. 119, No. 5, pp. 1382-1395.
Snow et al., "Early Accumulation of Heparan Sulfate in Neurons and in the Beta-amyloid Protein-containing Lesions of Alzheimer's Disease and Down's Syndrome", American Journal of Pathology, 1990, vol. 137, No. 5, pp. 1253-1270.
International Search Report, dated Jan. 17, 2013, from corresponding PCT application.
European Search Report, dated Aug. 27, 2012, from corresponding EP application.
Matsumoto, et al., "The 68 kDa Beta-Secretase with Heparan Sulfate is Expressed in Serum and Lymphocyte cytosol of Normal Aged and Alzheimer's Disease Patients," Alzheimer's Research, vol. 2, No. 4, 1196, pp. 115-119.
Leveugle, et al., "Binding of Heparan Sulfate Glycosaminoglycan to Beta-amyloid Peptide: Inhibition by Potentially Therapeutic Polysulfated Compounds," NeuroReport, vol. 5, 1994, pp. 1389-1392.
Japanese Office Action issued in Application No. 2014-535120, dated Nov. 7, 2017 with English Translation.
Japanese Office Action issued in Application No. 2014-535120, dated Mar. 7, 2017 with English Translation.

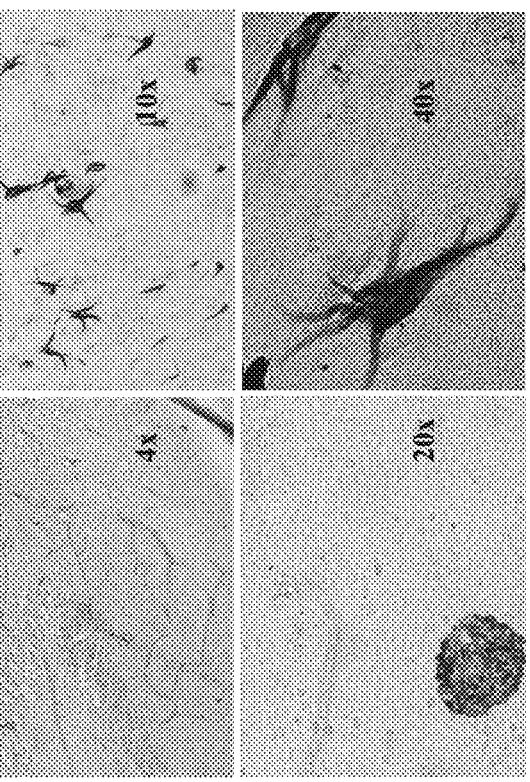
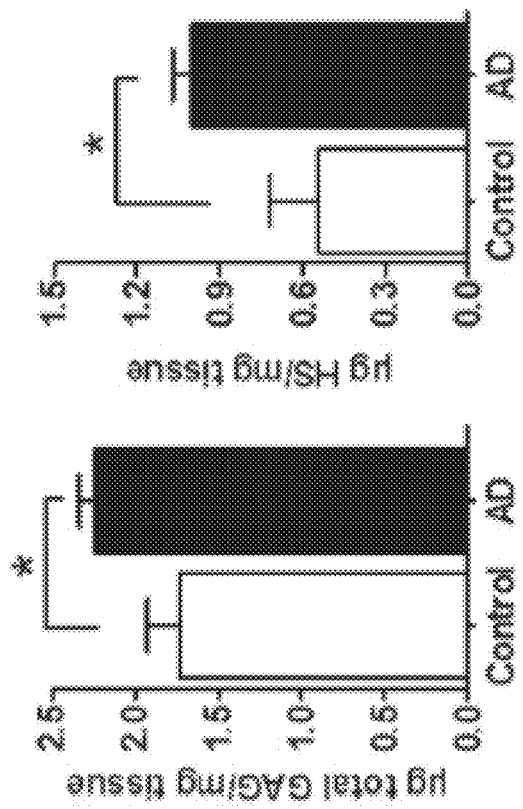
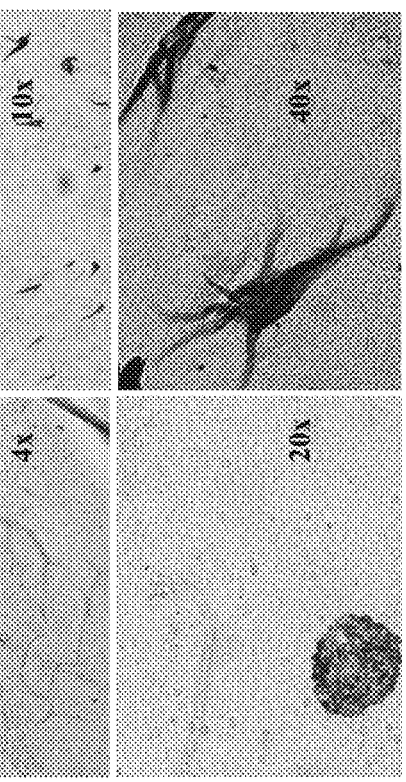
Figure 2C
Figure 2B
Figure 2A

| Target | Enzymes | Isoforms | Expression AD vs Control |
|---|---|---|---|
| Heparan sulfate | N-deacetylase/N-sulfotransferase | NDST-1 | NS |
| | | NDST-2 | ↑* |
| | | NDST-3 | ND |
| | | NDST-4 | ND |
| | D-glucuronyl C5-epimerase | GLCE | ↑* |
| | 2-O-sulfotransferase | 2-OST | ↑* |
| | 6-O-sulfotransferase | 6-OST-1 | ↑* |
| | | 6-OST-2-Var1 | ↑* |
| | | 6-OST-2-VarS | NS |
| | | 6-OST-3 | NS |
| | 3-O-sulfotransferase | 3-OST-1 | NS |
| | | 3-OST-2 | ↑** |
| | | 3-OST-3a1 | ↑* |
| | | 3-OST-3b1 | ↑* |
| | | 3-OST-4 | ↑*** |
| | | 3-OST-5 | NS |
| | | 3-OST-6 | ND |
| Chondroitin sulfate | Carbohydrate (N-acetylgalactosamine 4-0) sulfotransferase 8 | CHST8 Var1 | NS |
| | | CHST8 Var2 | NS |
| | | CHST8 Var3 | NS |
| Others | Heparanase | HSPE | ↑* |
| | Glutamine synthetase | GS | ↑** |
| | Glyceraldehyde-3-phosphate dehydrogenase | GAPDH | ↑* |
| | Chemokine (C-X-C) receptor 4 | CXCR4 | NS |

NS : No significant change in enzyme expression
ND : the enzyme was not detected

Figure 3

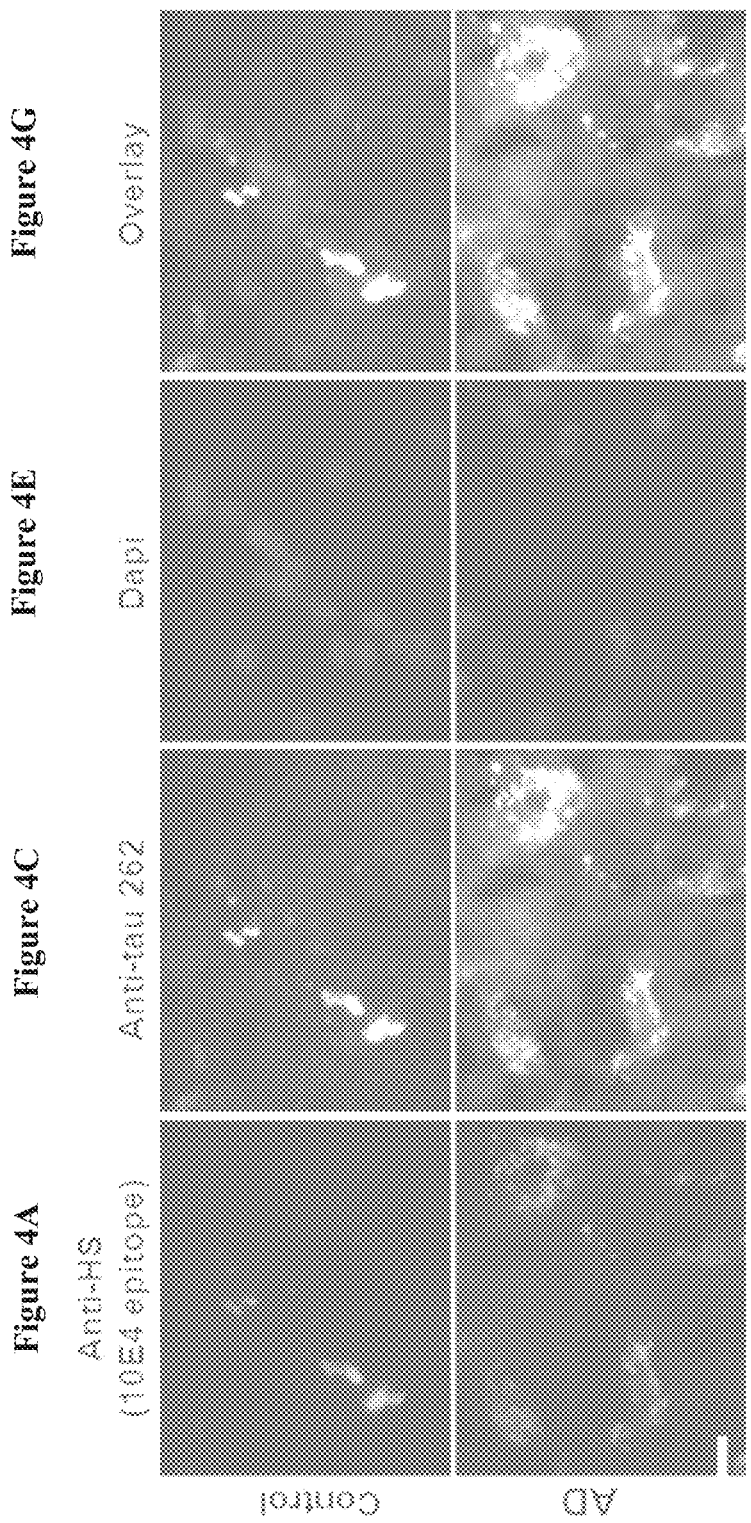

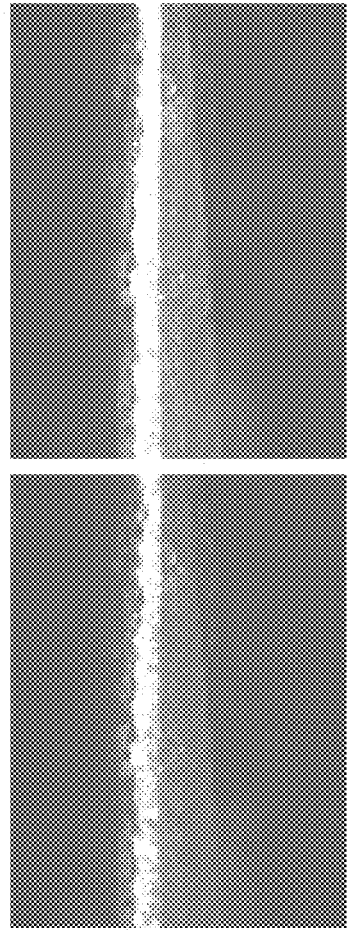
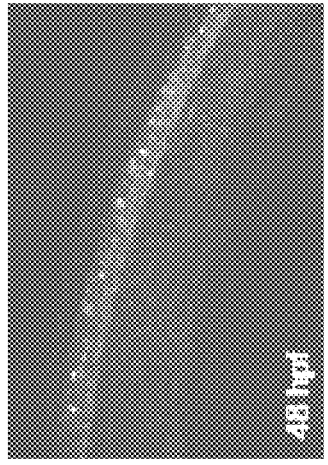
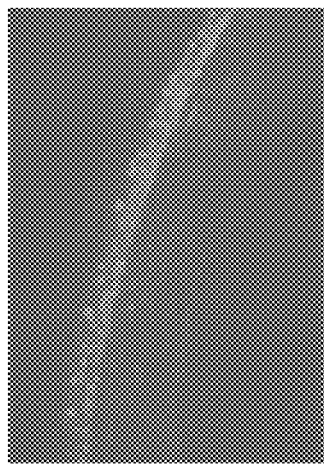
Figure 13A  Figure 13C  Figure 13E
Figure 13B  Figure 13D  Figure 13F

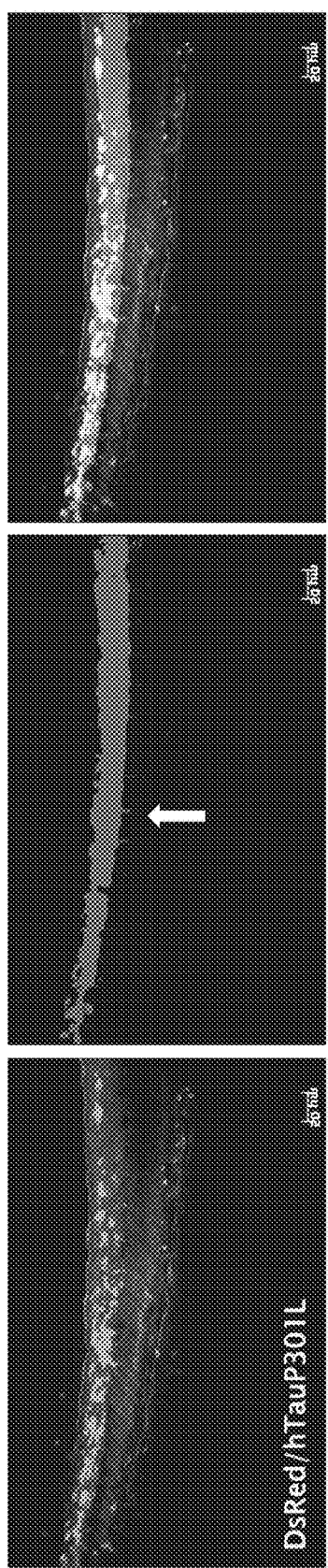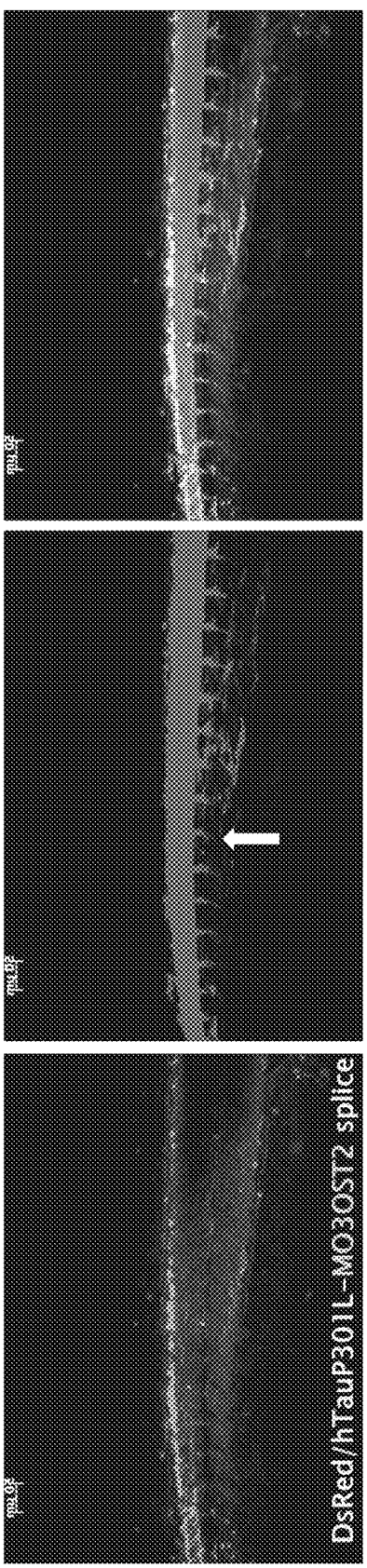

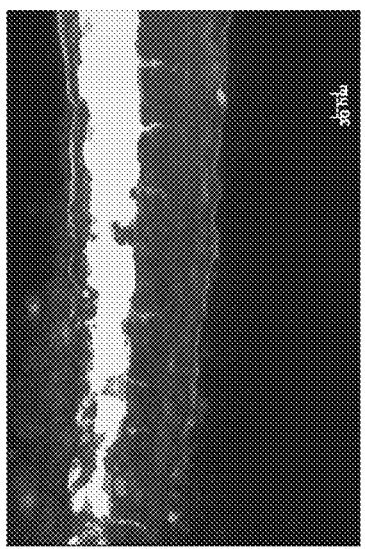 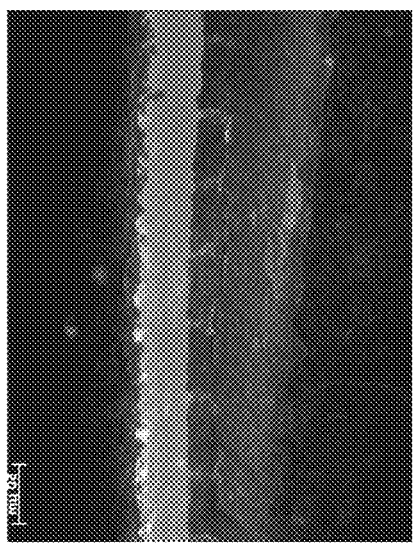
Figure 16A  Figure 16E
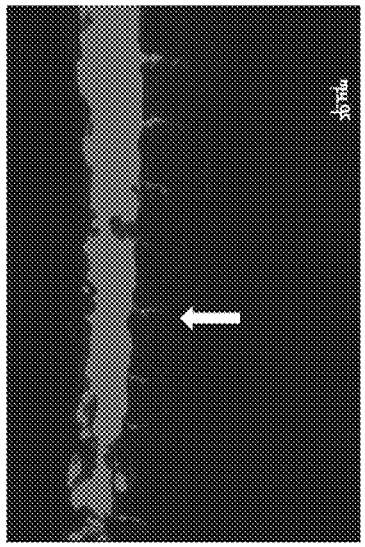 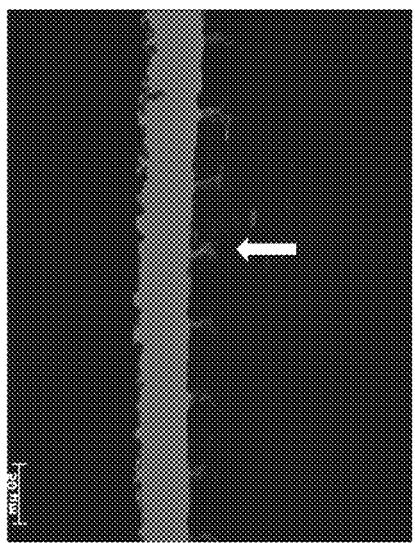
Figure 16C  Figure 16D
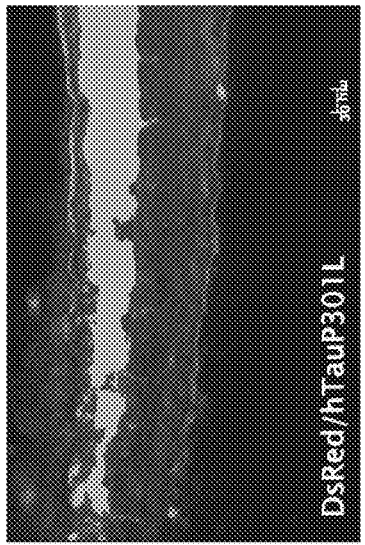 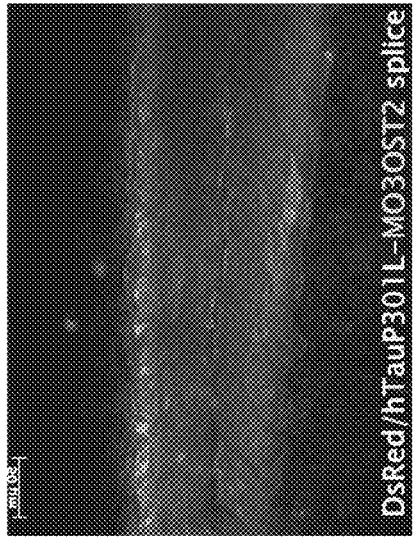 
Figure 16A  Figure 16B
DsRed/hTauP301L  DsRed/hTauP301L-MO3OST2 splice
Anterior

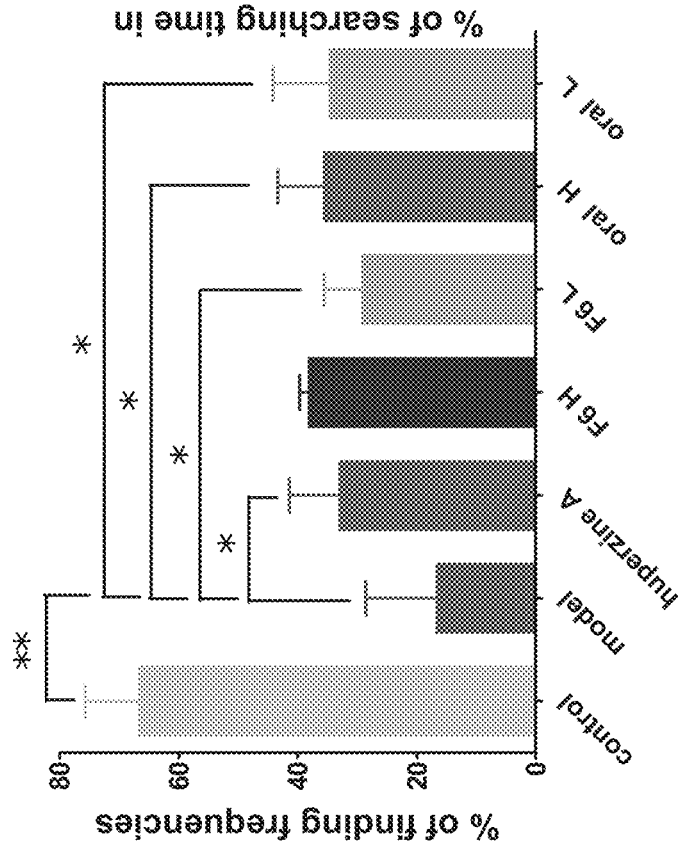
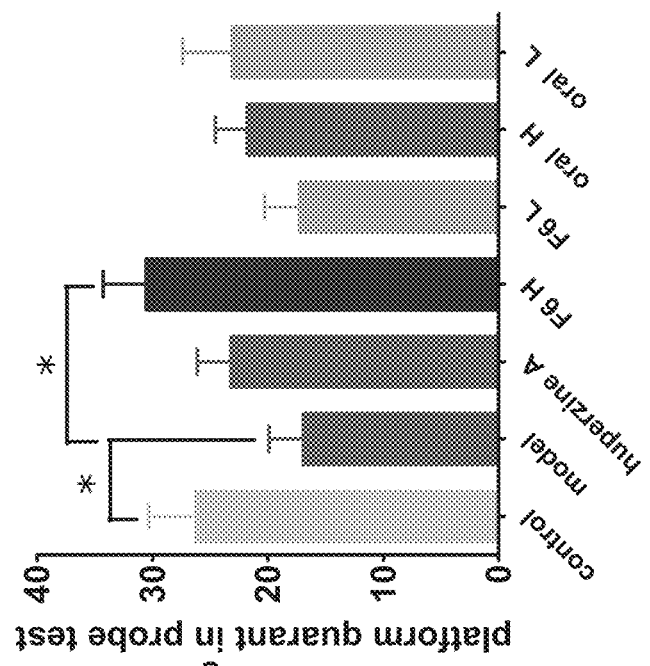
Figure 17A
Figure 17B

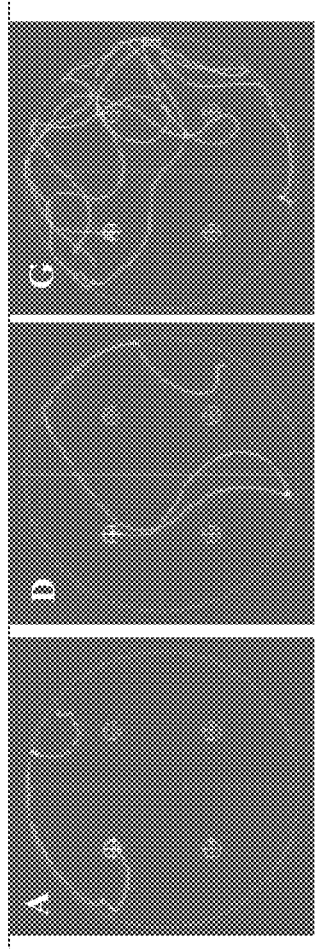
Figure 19A
Figure 19D
Figure 19G
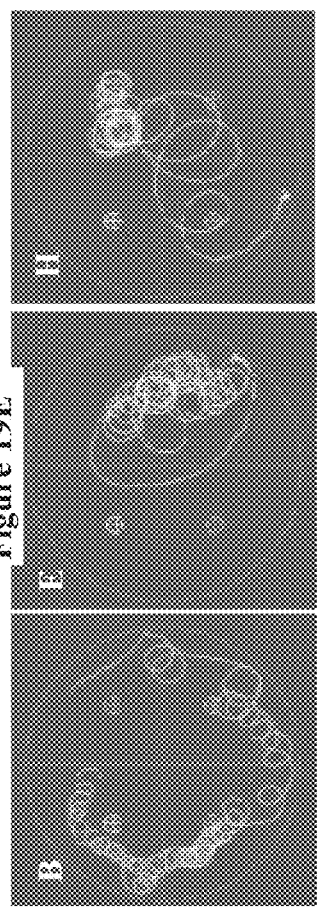
Figure 19B
Figure 19E
Figure 19H
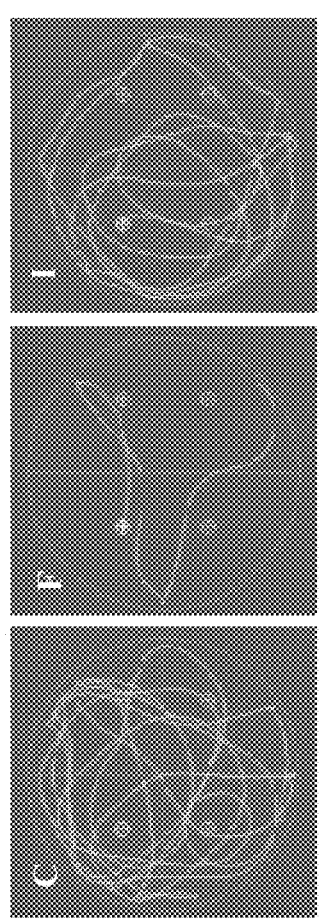
Figure 19C
Figure 19F
Figure 19I

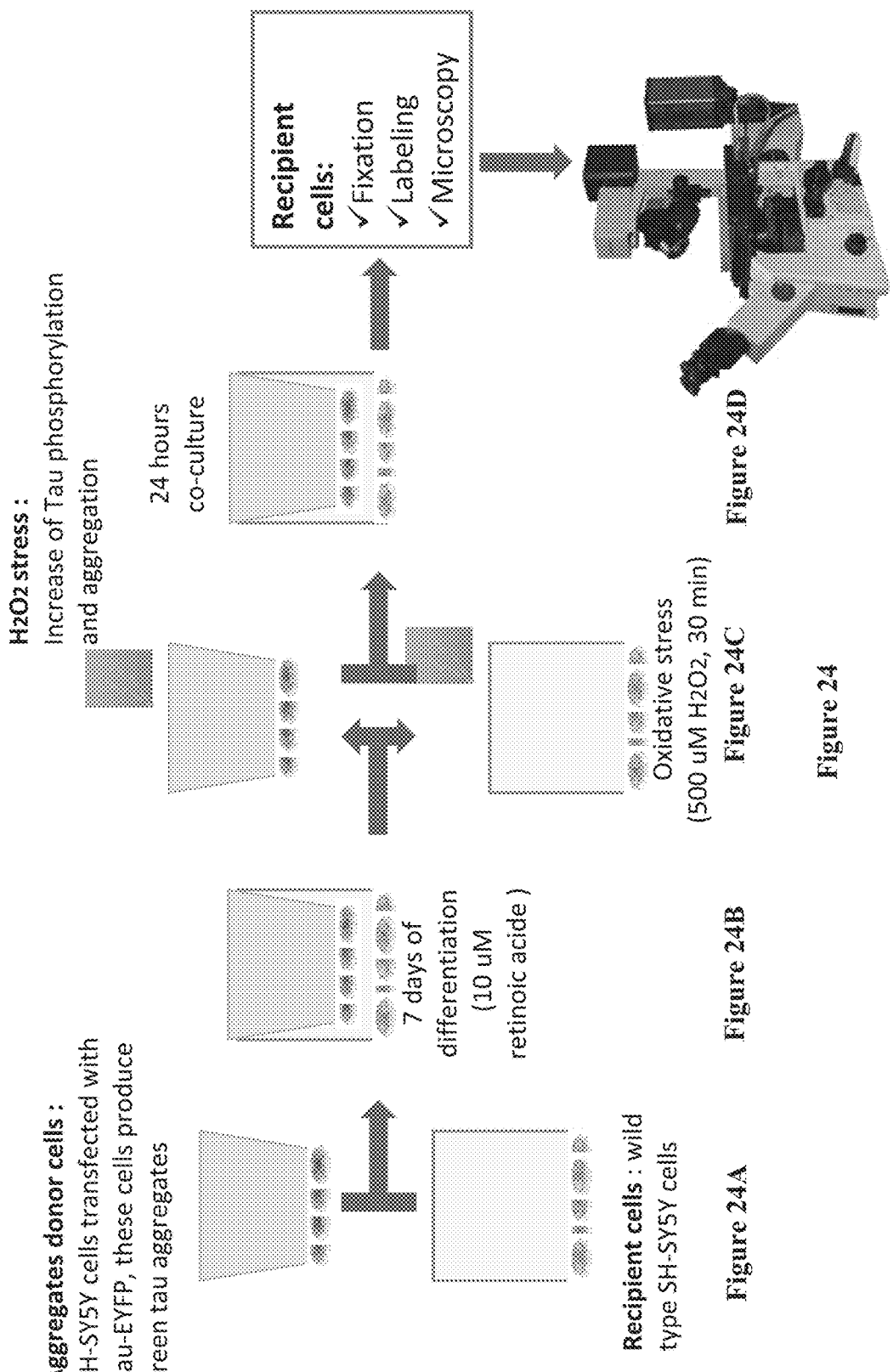

SEQUENCE LISTING

```
<160> NUMBER OF SEQ ID NOS: 78

<210> SEQ ID NO 1
<211> LENGTH: 1968
<212> TYPE: DNA
<213> ORGANISM: Homo sapiens
<220> FEATURE:
<221> NAME/KEY: gene
<222> LOCATION: (1)..(1968)

<400> SEQUENCE: 1
cgcagggcca cagcagctca gccgccggtg ccccctcgga aaccatgacc cccggcgcgg      60
gcccatggag ccatggccta tagggtcctg ggccgcgcgg ggccacctca gccgcggagg     120
gcgcgcaggc tgctcttcgc cttcacgctc tcgctctcct gcacttacct gtgttacagc     180
ttcctgtgct gctgcgacga cctgggtcgg agccgcctcc tcggcgcgcc tcgctgcctc     240
cgcggcccca gcgcgggcgg ccagaaactt ctccagaagt cccgccctg tgatccctcc       300 gggccgacgc ccagcgagcc cagcgctccc agcgcgcccg ccgccgccgt gcccgccct      360 cgcctctccg gttccaacca ctccggctca cccaagctgg gtaccaagcg gttgcccaa      420 gccctcattg tgggcgtgaa gaaggggggc acccgggccg tgctggagtt tatccgagta     480
```

```
cacccggacg tgcgggcctt gggcacggaa ccccacttct ttgacaggaa ctacggccgc    540
gggctggatt ggtacaggag cctgatgccc aggaccctcg agagccagat cacgctggag    600
aagacgccca gctactttgt cactcaagag gctcctcgac gcatcttcaa catgtcccga    660
gacaccaagc tgatcgtggt tgtgcggaac cctgtgaccc gtgccatctc tgattacacg    720
cagacactct ccaagaagcc cgacatcccg acctttgagg cctctcctt ccgcaaccgc     780 accctgggcc tggtggacgt gtcatggaac gccatccgca tcggcatgta cgtgctgcac    840
ctggagagct ggctgcagta cttcccgcta gctcagattc acttcgtcag tggcgagcga    900
ctcatcactg acccggccgg cgagatgggg cgagtccagg acttcctggg cattaagaga    960
ttcatcacgg acaagcactt ctatttcaac aagaccaaag gattcccttg cttgaaaaaa   1020
acagaatcga gctcctgcc tcgatgcttg ggcaaatcaa aagggagaac tcatgtacag    1080
attgatcctg aagtgataga ccagctccga gaatttttata gaccgtataa tatcaaattt   1140
tatgaaaccg ttgggcagga cttcaggtgg aataagccc acgaaaggaa agggctctca    1200
agggctcttc tgctcatctc ttccgtgaga tttgctccca gaccctctga tctccctcca   1260
acaaaccctg gctccagccc cctttcccaa cttgagttgc atcatcttgg aaccaggaag   1320
cccagctaaa gccaagagac cagagagtcc ctgccactag ttttcatcag tctgttcaag   1380
caaagttgat ctgctcctgg cacgtccagt aaattccaga atcattctcc tttctgccca   1440
taaagggcct tggagaattg ctttaagaag agtgaatgtt ccaatgatga tagatattat   1500
aagcgatgat ggttctgttg ctatgaacac agcagtcggt ccctgtcatt gtccacccag   1560
gagtggcctt gttaattcca agtggcatgt atcttccctc tgagcttcat ttcttcaaga   1620
tgctctgggt ggtgggatgg agaccatcc tcagccctcc tcagacctta tcaattcatt    1680
gagagattgc aaagctgaaa gcacctccgg ccactcctgg gagacagacc ctttggtgat   1740
gaaataaacc agtgacttca gagcctatgg tctcaactgt gcttgaaaaa cactgtctct   1800
gaaaacaact ttgtgattct ccctgctccc tgtggacaaa agcacataat tctgctgtta   1860
cgggtacttt gctcatacga gctttcatgt tcagcatgca atggaatcat gcttgtccat   1920
gtgaaataaa tatggctctc tcgtgtcctt aaaaaaaaaa aaaaaaaa              1968
```

<210> SEQ ID NO 2
<211> LENGTH: 367
<212> TYPE: PRT
<213> ORGANISM: Homo sapiens
<220> FEATURE:
<221> NAME/KEY: PEPTIDE
<222> LOCATION: (1)..(367)

<400> SEQUENCE: 2

```
Met Ala Tyr Arg Val Leu Gly Arg Ala Gly Pro Pro Gln Pro Arg Arg
1               5                   10                  15

Ala Arg Arg Leu Leu Phe Ala Phe Thr Leu Ser Leu Ser Cys Thr Tyr
            20                  25                  30

Leu Cys Tyr Ser Phe Leu Cys Cys Cys Asp Asp Leu Gly Arg Ser Arg
        35                  40                  45

Leu Leu Gly Ala Pro Arg Cys Leu Arg Gly Pro Ser Ala Gly Gly Gln
    50                  55                  60

Lys Leu Leu Gln Lys Ser Arg Pro Cys Asp Pro Ser Gly Pro Thr Pro
65                  70                  75                  80

Ser Glu Pro Ser Ala Pro Ser Ala Pro Ala Ala Val Pro Ala Pro
            85                  90                  95
```

```
Arg Leu Ser Gly Ser Asn His Ser Gly Ser Pro Lys Leu Gly Thr Lys
                100                 105                 110

Arg Leu Pro Gln Ala Leu Ile Val Gly Val Lys Lys Gly Gly Thr Arg
            115                 120                 125

Ala Val Leu Glu Phe Ile Arg Val His Pro Asp Val Arg Ala Leu Gly
        130                 135                 140

Thr Glu Pro His Phe Phe Asp Arg Asn Tyr Gly Arg Gly Leu Asp Trp
145                 150                 155                 160

Tyr Arg Ser Leu Met Pro Arg Thr Leu Glu Ser Gln Ile Thr Leu Glu
                165                 170                 175

Lys Thr Pro Ser Tyr Phe Val Thr Gln Glu Ala Pro Arg Arg Ile Phe
            180                 185                 190

Asn Met Ser Arg Asp Thr Lys Leu Ile Val Val Arg Asn Pro Val
        195                 200                 205

Thr Arg Ala Ile Ser Asp Tyr Thr Gln Thr Leu Ser Lys Lys Pro Asp
        210                 215                 220

Ile Pro Thr Phe Glu Gly Leu Ser Phe Arg Asn Arg Thr Leu Gly Leu
225                 230                 235                 240

Val Asp Val Ser Trp Asn Ala Ile Arg Ile Gly Met Tyr Val Leu His
                245                 250                 255

Leu Glu Ser Trp Leu Gln Tyr Phe Pro Leu Ala Gln Ile His Phe Val
            260                 265                 270

Ser Gly Glu Arg Leu Ile Thr Asp Pro Ala Gly Glu Met Gly Arg Val
        275                 280                 285

Gln Asp Phe Leu Gly Ile Lys Arg Phe Ile Thr Asp Lys His Phe Tyr
        290                 295                 300

Phe Asn Lys Thr Lys Gly Phe Pro Cys Leu Lys Lys Thr Glu Ser Ser
305                 310                 315                 320

Leu Leu Pro Arg Cys Leu Gly Lys Ser Lys Gly Arg Thr His Val Gln
                325                 330                 335

Ile Asp Pro Glu Val Ile Asp Gln Leu Arg Glu Phe Tyr Arg Pro Tyr
            340                 345                 350

Asn Ile Lys Phe Tyr Glu Thr Val Gly Gln Asp Phe Arg Trp Glu
        355                 360                 365

<210> SEQ ID NO 3
<211> LENGTH: 3203
<212> TYPE: DNA
<213> ORGANISM: Homo sapiens
<220> FEATURE:
<221> NAME/KEY: gene
<222> LOCATION: (1)..(3203)

<400> SEQUENCE: 3
cagcgcgcgg cggcggcggc agaggctgaa gcagaagccg cggcggagcc ggggaagcgg      60
gggcgctgca gacggagcag gtgccgccgg cgggtccgcg cgccccctc ggtcccttg      120 cctgaggctg agggggggc ggtggtgggg gggccacccg gactcggcgg gcagcgtggg    180 gcgggggcc atgcgccgg gctccccct ggcgcagcgg gacagcggcc agggccgggg    240
gcgcagcggg gtcgcttcat gcagccgggg cggctgggca gcggcggcgg cggcggcggc    300
ggcggcggcg gcggggggcgg cggctgaaac catgtccggg cagcgccggg ggctgccgcc    360
gccgccgccg ccgccgcgag ccgggagccg cgatggcccg gtggcccgca cctcctccgc    420
ctccgcctcc gcctccacct ctggccgcgc cgccgccgcc cggcgcctct gctaaggggc    480
```

```
cgccggcgcg caagctgctt tttatgtgca ccttgtccct gtctgtcacc tacctgtgct    540
acagcctcct gggcggctcg ggctccctgc aattccctct ggcgctgcag gagtcgccgg    600
gcgccgccgc cgagccccg ccgagcccgc cgccaccctc tctgctgcct accccgtgc     660 gcctcggcgc ccctcgcag ccgccgcgc cgccgccgct ggacaacgcg agccacgggg     720
agccgcccga gccccagag cagccagccg ccccgggac cgacggctgg gggctgccga     780
gcggcggcgg aggcgcccag gacgcctggc tccggacccc gctggccccc agcgagatga    840
tcacggctca gagcgcgctg ccggagaggg aagcgcagga gtccagcacc accgacgagg    900
atctcgcagg ccggagagcg gccaacggga gcagcgagag gggcggcgcc gtcagcaccc    960
ccgactatgg ggagaagaag ctgccacagg cgctcatcat cggggtcaag aaaggaggga   1020
cccgcgcgct gctggaggcg atccgcgtgc accggacgt gcgggcggtg ggcgtagagc   1080
cgcacttctt cgacaggaac tacgaaaagg ggttggagtg gtacagaaat gtgatgccca   1140
agactttgga tgggcaaata accatgagaa agactccaag ttactttgtg acaaatgagg   1200
ctcccaagcg cattcactcc atggccaagg acatcaaact gattgtggtg gtgagaaacc   1260
ccgtgaccag ggccatctct gactacacgc agacactgtc aaagaaaccc gagatcccca   1320
cctttgaggt gctggccttc aaaaaccgga ccctcgggct gatcgatgct tcctggagtg   1380
ccattcgaat agggatctat gcgctgcatc tggaaaactg gctccagtat ttccccctct   1440
cccagatcct ctttgtcagt ggtgagcgac tcattgtgga ccccgccggg gaaatggcca   1500
aagtacagga ttttctaggc ctcaaacgtg ttgtgactga gaagcatttc tatttcaaca   1560
aaaccaaggg gttcccttgc ctaagaagc cagaagacag cagtgccccg aggtgcttag   1620
gcaagagcaa aggtcggact catcctcgca ttgacccaga tgtcatccac agactgagga   1680
aattctacaa acccttcaac ttgatgtttt accaaatgac tggtcaagat tttcagtggg   1740
aacaggaaga gggtgataaa tgaggctaga gaggcagagg aaggctagtc aataagctaa   1800
ggaggctcct tgcctgagtc cttgaatacc ccagcttctg cagcttcact tgctggagtg   1860
ccaagtagat ctcctcctcc ttcatgcagc caggattgcc tccagtgctg ttagcttagg   1920
caaacaggtg gatcccatgg catccccatg gaggaaccag gcccatctgg gcagcagcat   1980
ctggttgacc agatggccac cagaacccac tgttcattct tatcttctgc tagttaatat   2040
agcctgaaga cagaggataa atagttgtca atgtcagaga cagtgctatt aatgtatatg   2100
tgagcgacaa aaaggtctg ctttataggg gttctcactc tagcttgggg agccagggtt    2160
ctagccctgt atctgtcatg ggcacctgct gtctaaacct ctgcttgggc ttctccccag   2220
aatgcacttt gtggctgagt gctccaggac tcctagggag caaggtcctc cctctaaggt   2280
gtttctagtc ttctctttaa aggtctcatc ccacaacccc tgacttcctc cctccccaca   2340
tcatgaaggc agaggcatgc acattcctca ctgaaaaaga aaacacacac ccacccacac   2400
acacacacac agaagaaaat gaaagctgac acacctcgaa gccttctttc caagagccct   2460
ctaaatgggg ttgggtctca ctcttcatga gtatcctggg ttgtgcagaa gcttagcata   2520
tgcccttgtg ttcggatcag gcccacaggg ctgctcaaag agtagagtaa ttgtaaccga   2580
ggtcagagct ctgggttgg cagagatgag tggccatatc tgggggtaaa agaagaaatc   2640
ctgtcctctt ggtgggaggt taccttacct gaagaccatc tctcccaagc actgtagttc   2700
tgagcatgtt tttggggtgg actctgtccc ctagggtccc tagaagggca aagaccagag   2760
agttgacaag tctgttatta ggaataatcc ttagccatgt aatggagaaa ggagcagtca   2820
gcattcttcc aatttgcccc accaccacct cctcgggctt cattttctct atttagagat   2880
```

```
ggcagagagt gaggtagtgg cgagaaagct gactccattc atcagatcca gtttatgagg   2940
gttgggggtg agcaagggct gtctgcagaa acccccatca agagctgctg aatgaagtgt   3000
cccttcccat cagtttgatt caattaaaat gcatcatttg acataaagca cttgttcaca   3060
gatctccaaa accaggaatt gttctagtaa aactggaaat tgtatgagt ggggggagtt    3120 aaatctgttc agctgttatt aaactgtcat ttctcccgct aaatgaaaac cgtgttgtta   3180
taaagcttaa tgcaacctga tta                                           3203
```

<210> SEQ ID NO 4
<211> LENGTH: 456
<212> TYPE: PRT
<213> ORGANISM: Homo sapiens

<400> SEQUENCE: 4

```
Met Ala Arg Trp Pro Ala Pro Pro Pro Pro Pro Pro Pro Pro Pro
1               5                   10                  15

Leu Ala Ala Pro Pro Pro Gly Ala Ser Ala Lys Gly Pro Pro Ala
            20                  25                  30

Arg Lys Leu Leu Phe Met Cys Thr Leu Ser Leu Ser Val Thr Tyr Leu
        35                  40                  45

Cys Tyr Ser Leu Leu Gly Gly Ser Gly Ser Leu Gln Phe Pro Leu Ala
    50                  55                  60

Leu Gln Glu Ser Pro Gly Ala Ala Ala Glu Pro Pro Ser Pro Pro
65                  70                  75                  80

Pro Pro Ser Leu Leu Pro Thr Pro Val Arg Leu Gly Ala Pro Ser Gln
                85                  90                  95

Pro Pro Ala Pro Pro Leu Asp Asn Ala Ser His Gly Glu Pro Pro
                100                 105                 110

Glu Pro Pro Glu Gln Pro Ala Ala Pro Gly Thr Asp Gly Trp Gly Leu
            115                 120                 125

Pro Ser Gly Gly Gly Gly Ala Gln Asp Ala Trp Leu Arg Thr Pro Leu
        130                 135                 140

Ala Pro Ser Glu Met Ile Thr Ala Gln Ser Ala Leu Pro Glu Arg Glu
145                 150                 155                 160

Ala Gln Glu Ser Ser Thr Thr Asp Glu Asp Leu Ala Gly Arg Arg Ala
                165                 170                 175

Ala Asn Gly Ser Ser Glu Arg Gly Gly Ala Val Ser Thr Pro Asp Tyr
            180                 185                 190

Gly Glu Lys Lys Leu Pro Gln Ala Leu Ile Ile Gly Val Lys Lys Gly
        195                 200                 205

Gly Thr Arg Ala Leu Leu Glu Ala Ile Arg Val His Pro Asp Val Arg
    210                 215                 220

Ala Val Gly Val Glu Pro His Phe Phe Asp Arg Asn Tyr Glu Lys Gly
225                 230                 235                 240

Leu Glu Trp Tyr Arg Asn Val Met Pro Lys Thr Leu Asp Gly Gln Ile
                245                 250                 255

Thr Met Glu Lys Thr Pro Ser Tyr Phe Val Thr Asn Glu Ala Pro Lys
            260                 265                 270

Arg Ile His Ser Met Ala Lys Asp Ile Lys Leu Ile Val Val Val Arg
        275                 280                 285

Asn Pro Val Thr Arg Ala Ile Ser Asp Tyr Thr Gln Thr Leu Ser Lys
    290                 295                 300

Lys Pro Glu Ile Pro Thr Phe Glu Val Leu Ala Phe Lys Asn Arg Thr
```

```
                305                 310                 315                 320
Leu Gly Leu Ile Asp Ala Ser Trp Ser Ala Ile Arg Ile Gly Ile Tyr
                325                 330                 335

Ala Leu His Leu Glu Asn Trp Leu Gln Tyr Phe Pro Leu Ser Gln Ile
                340                 345                 350

Leu Phe Val Ser Gly Glu Arg Leu Ile Val Asp Pro Ala Gly Glu Met
                355                 360                 365

Ala Lys Val Gln Asp Phe Leu Gly Leu Lys Arg Val Val Thr Glu Lys
            370                 375                 380

His Phe Tyr Phe Asn Lys Thr Lys Gly Phe Pro Cys Leu Lys Lys Pro
385                 390                 395                 400

Glu Asp Ser Ser Ala Pro Arg Cys Leu Gly Lys Ser Lys Gly Arg Thr
                405                 410                 415

His Pro Arg Ile Asp Pro Asp Val Ile His Arg Leu Arg Lys Phe Tyr
                420                 425                 430

Lys Pro Phe Asn Leu Met Phe Tyr Gln Met Thr Gly Gln Asp Phe Gln
                435                 440                 445

Trp Glu Gln Glu Glu Gly Asp Lys
450                 455

<210> SEQ ID NO 5
<211> LENGTH: 25
<212> TYPE: DNA
<213> ORGANISM: Artificial Sequence
<220> FEATURE:
<223> OTHER INFORMATION: Morpholino 3-OST2
<220> FEATURE:
<221> NAME/KEY: misc_feature
<222> LOCATION: (1)..(20)

<400> SEQUENCE: 5
ggcttgacag gaacctatat gccat                                               25

<210> SEQ ID NO 6
<211> LENGTH: 25
<212> TYPE: DNA
<213> ORGANISM: Artificial Sequence
<220> FEATURE:
<223> OTHER INFORMATION: Morpholino 3-OST4
<220> FEATURE:
<221> NAME/KEY: misc_feature
<222> LOCATION: (1)..(20)

<400> SEQUENCE: 6
taccgtaaaa ccaggtcgtg aagcc                                               25

<210> SEQ ID NO 7
<211> LENGTH: 20
<212> TYPE: DNA
<213> ORGANISM: Artificial Sequence
<220> FEATURE:
<223> OTHER INFORMATION: Primer Oligonucleotide sense (3-OST-2)
<220> FEATURE:
<221> NAME/KEY: misc_feature
<222> LOCATION: (1)..(20)

<400> SEQUENCE: 7
ggaaccccac ttctttgaca                                                     20

<210> SEQ ID NO 8
<211> LENGTH: 20
<212> TYPE: DNA
<213> ORGANISM: Artificial Sequence
```

```
<220> FEATURE:
<223> OTHER INFORMATION: Primer Oligonucleotide anti-sense (3-OST-2)

<400> SEQUENCE: 8
gtcgaggagc ctcttgagtg                                                 20

<210> SEQ ID NO 9
<211> LENGTH: 20
<212> TYPE: DNA
<213> ORGANISM: Artificial Sequence
<220> FEATURE:
<223> OTHER INFORMATION: Primer Oligonucleotide sense (3-OST-4)
<220> FEATURE:
<221> NAME/KEY: misc_feature
<222> LOCATION: (1)..(20)

<400> SEQUENCE: 9
aagagcaaag gtcggactca                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer Oligonucleotide anti-sense (3-OST-4)

<400> SEQUENCE: 10
accctcttcc tgttcccact                                                 20

<210> SEQ ID NO 11
<211> LENGTH: 19
<212> TYPE: DNA
<213> ORGANISM: Artificial Sequence
<220> FEATURE:
<223> OTHER INFORMATION: Primer Oligonucleotide sense NDST-1

<400> SEQUENCE: 11
ggaagtgtgt ccgtggttc                                                  19

<210> SEQ ID NO 12
<211> LENGTH: 20
<212> TYPE: DNA
<213> ORGANISM: Artificial Sequence
<220> FEATURE:
<223> OTHER INFORMATION: Primer Oligonucleotide anti-sense NDST-1

<400> SEQUENCE: 12
ccctggtaac tgtgctccat                                                 20

<210> SEQ ID NO 13
<211> LENGTH: 20
<212> TYPE: DNA
<213> ORGANISM: Artificial Sequence
<220> FEATURE:
<223> OTHER INFORMATION: Primer oligonucleotide sense NDST-2

<400> SEQUENCE: 13
ctccagttgt ggaaggtggt                                                 20

<210> SEQ ID NO 14
<211> LENGTH: 20
<212> TYPE: DNA
<213> ORGANISM: Artificial Sequence
<220> FEATURE:
<223> OTHER INFORMATION: Primer oligonucleotide anti-sense NDST-2

<400> SEQUENCE: 14
```
cttagggctg gtggacacat                                               20

<210> SEQ ID NO 15
<211> LENGTH: 20
<212> TYPE: DNA
<213> ORGANISM: Artificial Sequence
<220> FEATURE:
<223> OTHER INFORMATION: Primer oligonucleotide sense NDST-3

<400> SEQUENCE: 15
cgacctccaa cacctaccat                                               20

<210> SEQ ID NO 16
<211> LENGTH: 20
<212> TYPE: DNA
<213> ORGANISM: Artificial Sequence
<220> FEATURE:
<223> OTHER INFORMATION: Primer oligonucleotide anti-sense NDST-3

<400> SEQUENCE: 16
taggactgtg gggtctgtcc                                               20

<210> SEQ ID NO 17
<211> LENGTH: 20
<212> TYPE: DNA
<213> ORGANISM: Artificial Sequence
<220> FEATURE:
<223> OTHER INFORMATION: Primer oligonucleotide sense NDST-4

<400> SEQUENCE: 17
gcaacggtga ttcaggatct                                               20

<210> SEQ ID NO 18
<211> LENGTH: 20
<212> TYPE: DNA
<213> ORGANISM: Artificial Sequence
<220> FEATURE:
<223> OTHER INFORMATION: Primer oligonucleotide anti-sense NDST-4

<400> SEQUENCE: 18
tgtgcagcca aaagttcaag                                               20

<210> SEQ ID NO 19
<211> LENGTH: 20
<212> TYPE: DNA
<213> ORGANISM: Artificial Sequence
<220> FEATURE:
<223> OTHER INFORMATION: Primer oligonucleotide sense GLCE

<400> SEQUENCE: 19
ggaagtgtgt ccgtggttct                                               20

<210> SEQ ID NO 20
<211> LENGTH: 20
<212> TYPE: DNA
<213> ORGANISM: Artificial Sequence
<220> FEATURE:
<223> OTHER INFORMATION: Primer oligonucleotide anti-sense GLCE

<400> SEQUENCE: 20
ccctggtaac tgtgctccat                                               20

<210> SEQ ID NO 21
<211> LENGTH: 20
<212> TYPE: DNA

```
<213> ORGANISM: Artificial Sequence
<220> FEATURE:
<223> OTHER INFORMATION: Primer oligonucleotide sense HS2STVar1

<400> SEQUENCE: 21
cgaagtccga gaaattgagc                                                    20

<210> SEQ ID NO 22
<211> LENGTH: 20
<212> TYPE: DNA
<213> ORGANISM: Artificial Sequence
<220> FEATURE:
<223> OTHER INFORMATION: Primer oligonucleotide anti-sense HS2STVar1

<400> SEQUENCE: 22
aatgaagtgc ttgccgtttt                                                    20

<210> SEQ ID NO 23
<211> LENGTH: 20
<212> TYPE: DNA
<213> ORGANISM: Artificial Sequence
<220> FEATURE:
<223> OTHER INFORMATION: Primer oligonucleotide sense HS2STVar2

<400> SEQUENCE: 23
cgaagtccga gaaattgagc                                                    20

<210> SEQ ID NO 24
<211> LENGTH: 20
<212> TYPE: DNA
<213> ORGANISM: Artificial Sequence
<220> FEATURE:
<223> OTHER INFORMATION: Primer oligonucleotide anti-sense HS2STVar2

<400> SEQUENCE: 24
aatgaagtgc ttgccgtttt                                                    20

<210> SEQ ID NO 25
<211> LENGTH: 20
<212> TYPE: DNA
<213> ORGANISM: Artificial Sequence
<220> FEATURE:
<223> OTHER INFORMATION: Primer oligonucleotide sense HS6ST1

<400> SEQUENCE: 25
ggcccttcat gcagtacaat                                                    20

<210> SEQ ID NO 26
<211> LENGTH: 20
<212> TYPE: DNA
<213> ORGANISM: Artificial Sequence
<220> FEATURE:
<223> OTHER INFORMATION: Primer oligonucleotide anti-sense HS6ST1

<400> SEQUENCE: 26
tacagctgca tgtccaggtc                                                    20

<210> SEQ ID NO 27
<211> LENGTH: 20
<212> TYPE: DNA
<213> ORGANISM: Artificial Sequence
<220> FEATURE:
<223> OTHER INFORMATION: Primer oligonucleotide sense HS6STVarL

<400> SEQUENCE: 27
cggggttctc caaacactaa                                                    20
```

```
<210> SEQ ID NO 28
<211> LENGTH: 20
<212> TYPE: DNA
<213> ORGANISM: Artificial Sequence
<220> FEATURE:
<223> OTHER INFORMATION: Primer oligonucleotide anti-sense HS6STVarL

<400> SEQUENCE: 28
gtctcggagg atggtgatgt                                              20

<210> SEQ ID NO 29
<211> LENGTH: 20
<212> TYPE: DNA
<213> ORGANISM: Artificial Sequence
<220> FEATURE:
<223> OTHER INFORMATION: Primer oligonucleotide sense HS6STVarS

<400> SEQUENCE: 29
aggctccttc agacccattt                                              20

<210> SEQ ID NO 30
<211> LENGTH: 20
<212> TYPE: DNA
<213> ORGANISM: Artificial Sequence
<220> FEATURE:
<223> OTHER INFORMATION: Primer oligonucleotide anti-sense HS6STVarS

<400> SEQUENCE: 30
tcggatttgg gttctgactc                                              20

<210> SEQ ID NO 31
<211> LENGTH: 20
<212> TYPE: DNA
<213> ORGANISM: Artificial Sequence
<220> FEATURE:
<223> OTHER INFORMATION: Primer oligonucleotide sense HS6ST3

<400> SEQUENCE: 31
catctccccc ttcacacagt                                              20

<210> SEQ ID NO 32
<211> LENGTH: 20
<212> TYPE: DNA
<213> ORGANISM: Artificial Sequence
<220> FEATURE:
<223> OTHER INFORMATION: Primer oligonucleotide anti-sense HS6ST3

<400> SEQUENCE: 32
ctcgtaaagc tgcatgtcca                                              20

<210> SEQ ID NO 33
<211> LENGTH: 20
<212> TYPE: DNA
<213> ORGANISM: Artificial Sequence
<220> FEATURE:
<223> OTHER INFORMATION: Primer oligonucleotide sense HS3ST1

<400> SEQUENCE: 33
accacatgca gaagcacaag                                              20

<210> SEQ ID NO 34
<211> LENGTH: 20
<212> TYPE: DNA
<213> ORGANISM: Artificial Sequence
<220> FEATURE:
```

<223> OTHER INFORMATION: Primer oligonucleotide anti-sense HS3ST1

<400> SEQUENCE: 34
ttgagggcct tgtagtccac          20

<210> SEQ ID NO 35
<211> LENGTH: 20
<212> TYPE: DNA
<213> ORGANISM: Artificial Sequence
<220> FEATURE:
<223> OTHER INFORMATION: Primer Oligonuclotide sense HS3ST3A1

<400> SEQUENCE: 35
acgcccagtt acttcgtcac          20

<210> SEQ ID NO 36
<211> LENGTH: 20
<212> TYPE: DNA
<213> ORGANISM: Artificial Sequence
<220> FEATURE:
<223> OTHER INFORMATION: Primer Oligonuclotide anti-sense HS3ST3A1

<400> SEQUENCE: 36
gaacgtcaag ctctcgaagg          20

<210> SEQ ID NO 37
<211> LENGTH: 20
<212> TYPE: DNA
<213> ORGANISM: Artificial Sequence
<220> FEATURE:
<223> OTHER INFORMATION: Primer Oligonuclotide sense HS3ST3B1

<400> SEQUENCE: 37
acgcccagtt acttcgtcac          20

<210> SEQ ID NO 38
<211> LENGTH: 20
<212> TYPE: DNA
<213> ORGANISM: Artificial Sequence
<220> FEATURE:
<223> OTHER INFORMATION: Primer Oligonuclotide anti-sense HS3ST3B1

<400> SEQUENCE: 38
tctgcgtgta gtccgagatg          20

<210> SEQ ID NO 39
<211> LENGTH: 20
<212> TYPE: DNA
<213> ORGANISM: Artificial Sequence
<220> FEATURE:
<223> OTHER INFORMATION: Primer Oligonuclotide sense HS3ST5

<400> SEQUENCE: 39
gctagagggg aaggagagga          20

<210> SEQ ID NO 40
<211> LENGTH: 20
<212> TYPE: DNA
<213> ORGANISM: Artificial Sequence
<220> FEATURE:
<223> OTHER INFORMATION: Primer Oligonuclotide anti-sense HS3ST5

<400> SEQUENCE: 40
ccatcgacga catgaaattg          20

```
<210> SEQ ID NO 41
<211> LENGTH: 20
<212> TYPE: DNA
<213> ORGANISM: Artificial Sequence
<220> FEATURE:
<223> OTHER INFORMATION: Primer Oligonuclotide sense HS3ST6

<400> SEQUENCE: 41
ctgtcccact tcctgttcgt                                               20

<210> SEQ ID NO 42
<211> LENGTH: 20
<212> TYPE: DNA
<213> ORGANISM: Artificial Sequence
<220> FEATURE:
<223> OTHER INFORMATION: Primer Oligonuclotide anti-sense HS3ST6

<400> SEQUENCE: 42
ccttggtggc gttgaagtag                                               20

<210> SEQ ID NO 43
<211> LENGTH: 20
<212> TYPE: DNA
<213> ORGANISM: Artificial Sequence
<220> FEATURE:
<223> OTHER INFORMATION: Primer Oligonuclotide sense TUBA1A

<400> SEQUENCE: 43
gcaacaacct ctcctcttcg                                               20

<210> SEQ ID NO 44
<211> LENGTH: 20
<212> TYPE: DNA
<213> ORGANISM: Artificial Sequence
<220> FEATURE:
<223> OTHER INFORMATION: Primer Oligonuclotide anti-sense TUBA1A

<400> SEQUENCE: 44
gaatcatctc ctcccccaat                                               20

<210> SEQ ID NO 45
<211> LENGTH: 21
<212> TYPE: DNA
<213> ORGANISM: Artificial Sequence
<220> FEATURE:
<223> OTHER INFORMATION: Primer Oligonuclotide sense TBP

<400> SEQUENCE: 45
tgcacaggag ccaagagtga a                                             21

<210> SEQ ID NO 46
<211> LENGTH: 20
<212> TYPE: DNA
<213> ORGANISM: Artificial Sequence
<220> FEATURE:
<223> OTHER INFORMATION: Primer Oligonuclotide anti-sense TBP

<400> SEQUENCE: 46
cacatcacag ctccccacca                                               20

<210> SEQ ID NO 47
<211> LENGTH: 19
<212> TYPE: DNA
<213> ORGANISM: Artificial Sequence
<220> FEATURE:
<223> OTHER INFORMATION: Primer Oligonucleotide sense GAPDH
```

```
<400> SEQUENCE: 47
ccgtctagaa aaacctgcc                                                    19

<210> SEQ ID NO 48
<211> LENGTH: 20
<212> TYPE: DNA
<213> ORGANISM: Artificial Sequence
<220> FEATURE:
<223> OTHER INFORMATION: Primer Oligonucleotide anti-sense GAPDH

<400> SEQUENCE: 48
gccaaattcg ttgtcatacc                                                   20

<210> SEQ ID NO 49
<211> LENGTH: 20
<212> TYPE: DNA
<213> ORGANISM: Artificial Sequence
<220> FEATURE:
<223> OTHER INFORMATION: Primer Oligonucleotide sense 3-OST-1

<400> SEQUENCE: 49
cggtgtctgc acagctctaa                                                   20

<210> SEQ ID NO 50
<211> LENGTH: 20
<212> TYPE: DNA
<213> ORGANISM: Artificial Sequence
<220> FEATURE:
<223> OTHER INFORMATION: Primer Oligonucleotide anti-sense 3-OST-1

<400> SEQUENCE: 50
cgaccagctc aaagaacctc                                                   20

<210> SEQ ID NO 51
<211> LENGTH: 20
<212> TYPE: DNA
<213> ORGANISM: Artificial Sequence
<220> FEATURE:
<223> OTHER INFORMATION: Primer Oligonucleotide sense 3-OST-2

<400> SEQUENCE: 51
ctccagtact tccggctgtc                                                   20

<210> SEQ ID NO 52
<211> LENGTH: 20
<212> TYPE: DNA
<213> ORGANISM: Artificial Sequence
<220> FEATURE:
<223> OTHER INFORMATION: Primer Oligonucleotide anti-sense 3-OST-2

<400> SEQUENCE: 52
ctgctgctct ctggcttctt                                                   20

<210> SEQ ID NO 53
<211> LENGTH: 20
<212> TYPE: DNA
<213> ORGANISM: Artificial Sequence
<220> FEATURE:
<223> OTHER INFORMATION: Primer Oligonucleotide sense 3-OST-3X

<400> SEQUENCE: 53
cagggaacta atgcccaaaa                                                   20

<210> SEQ ID NO 54
<211> LENGTH: 20
```

-continued

```
<212> TYPE: DNA
<213> ORGANISM: Artificial Sequence
<220> FEATURE:
<223> OTHER INFORMATION: Primer Oligonucleotide anti-ense 3-OST-3X

<400> SEQUENCE: 54
tctcgcacca cgactatcag                                              20

<210> SEQ ID NO 55
<211> LENGTH: 20
<212> TYPE: DNA
<213> ORGANISM: Artificial Sequence
<220> FEATURE:
<223> OTHER INFORMATION: Primer Oligonucleotide sense 3-OST-3Z

<400> SEQUENCE: 55
gaagaaactc gggctcctct                                              20

<210> SEQ ID NO 56
<211> LENGTH: 20
<212> TYPE: DNA
<213> ORGANISM: Artificial Sequence
<220> FEATURE:
<223> OTHER INFORMATION: Primer Oligonucleotide anti-sense 3-OST-3Z

<400> SEQUENCE: 56
cgtctccttc gctcgattac                                              20

<210> SEQ ID NO 57
<211> LENGTH: 20
<212> TYPE: DNA
<213> ORGANISM: Artificial Sequence
<220> FEATURE:
<223> OTHER INFORMATION: Primer Oligonucleotide sense 3-OST-4

<400> SEQUENCE: 57
gctcttcacc tggaaagctg                                              20

<210> SEQ ID NO 58
<211> LENGTH: 20
<212> TYPE: DNA
<213> ORGANISM: Artificial Sequence
<220> FEATURE:
<223> OTHER INFORMATION: Primer Oligonucleotide anti-sense 3-OST-4

<400> SEQUENCE: 58
aatcctgcac ttttgccatc                                              20

<210> SEQ ID NO 59
<211> LENGTH: 20
<212> TYPE: DNA
<213> ORGANISM: Artificial Sequence
<220> FEATURE:
<223> OTHER INFORMATION: Primer Oligonucleotide sense 3-OST-5

<400> SEQUENCE: 59
actttcggaa gggtctggat                                              20

<210> SEQ ID NO 60
<211> LENGTH: 20
<212> TYPE: DNA
<213> ORGANISM: Artificial Sequence
<220> FEATURE:
<223> OTHER INFORMATION: Primer Oligonucleotide anti-sense 3-OST-5

<400> SEQUENCE: 60
```

```
ggtggagctg tgaagtagcc                                                 20

<210> SEQ ID NO 61
<211> LENGTH: 20
<212> TYPE: DNA
<213> ORGANISM: Artificial Sequence
<220> FEATURE:
<223> OTHER INFORMATION: Primer Oligonucleotide sense 3-OST-6

<400> SEQUENCE: 61
cacctgcatc tccatcctct                                                 20

<210> SEQ ID NO 62
<211> LENGTH: 20
<212> TYPE: DNA
<213> ORGANISM: Artificial Sequence
<220> FEATURE:
<223> OTHER INFORMATION: Primer Oligonucleotide anti-sense 3-OST-6

<400> SEQUENCE: 62
ctctcggcct gaactattgc                                                 20

<210> SEQ ID NO 63
<211> LENGTH: 20
<212> TYPE: DNA
<213> ORGANISM: Artificial Sequence
<220> FEATURE:
<223> OTHER INFORMATION: Primer Oligonucleotide sense 3-OST-7

<400> SEQUENCE: 63
aaacaccggg gtatttcaca                                                 20

<210> SEQ ID NO 64
<211> LENGTH: 20
<212> TYPE: DNA
<213> ORGANISM: Artificial Sequence
<220> FEATURE:
<223> OTHER INFORMATION: Primer Oligonucleotide anti-sense 3-OST-7

<400> SEQUENCE: 64
tcttcaccag catgttctcg                                                 20

<210> SEQ ID NO 65
<211> LENGTH: 20
<212> TYPE: DNA
<213> ORGANISM: Artificial Sequence
<220> FEATURE:
<223> OTHER INFORMATION: Primer Oligonucleotide sense GAPDH

<400> SEQUENCE: 65
gatacacgga gcaccaggtt                                                 20

<210> SEQ ID NO 66
<211> LENGTH: 20
<212> TYPE: DNA
<213> ORGANISM: Artificial Sequence
<220> FEATURE:
<223> OTHER INFORMATION: Primer Oligonucleotide anti-sense GAPDH

<400> SEQUENCE: 66
gccatcaggt cacatacacg                                                 20

<210> SEQ ID NO 67
<211> LENGTH: 20
<212> TYPE: DNA
<213> ORGANISM: Artificial Sequence
```

```
<220> FEATURE:
<223> OTHER INFORMATION: Primer Oligonucleotide sense bactin1

<400> SEQUENCE: 67
ctcttccagc cttccttcct                                              20

<210> SEQ ID NO 68
<211> LENGTH: 20
<212> TYPE: DNA
<213> ORGANISM: Artificial Sequence
<220> FEATURE:
<223> OTHER INFORMATION: Primer Oligonucleotide anti-sense bactin1

<400> SEQUENCE: 68
cttctgcata cggtcagcaa                                              20

<210> SEQ ID NO 69
<211> LENGTH: 20
<212> TYPE: DNA
<213> ORGANISM: Artificial Sequence
<220> FEATURE:
<223> OTHER INFORMATION: Primer Oligonucleotide sense TBP

<400> SEQUENCE: 69
gagcaacaga ggcaacaaca                                              20

<210> SEQ ID NO 70
<211> LENGTH: 20
<212> TYPE: DNA
<213> ORGANISM: Artificial Sequence
<220> FEATURE:
<223> OTHER INFORMATION: Primer Oligonucleotide anti-sense TBP

<400> SEQUENCE: 70
gataggcgtc atagggtga                                               20

<210> SEQ ID NO 71
<211> LENGTH: 21
<212> TYPE: DNA
<213> ORGANISM: Artificial Sequence
<220> FEATURE:
<223> OTHER INFORMATION: Si RNA OST-2 sense

<400> SEQUENCE: 71
gggcuggauu gguacaggat t                                            21

<210> SEQ ID NO 72
<211> LENGTH: 21
<212> TYPE: DNA
<213> ORGANISM: Artificial Sequence
<220> FEATURE:
<223> OTHER INFORMATION: Si RNA OST-2 antisense

<400> SEQUENCE: 72
uccuguacca auccagcccg c                                            21

<210> SEQ ID NO 73
<211> LENGTH: 21
<212> TYPE: DNA
<213> ORGANISM: Artificial Sequence
<220> FEATURE:
<223> OTHER INFORMATION: SiRNA OST-2 sense

<400> SEQUENCE: 73
aaucaaaagg gagaacucat t                                            21
```

```
<210> SEQ ID NO 74
<211> LENGTH: 21
<212> TYPE: DNA
<213> ORGANISM: Artificial Sequence
<220> FEATURE:
<223> OTHER INFORMATION: SiRNA OST-2 antisense

<400> SEQUENCE: 74
ugaguucucc cuuuugauut g                                              21

<210> SEQ ID NO 75
<211> LENGTH: 21
<212> TYPE: DNA
<213> ORGANISM: Artificial Sequence
<220> FEATURE:
<223> OTHER INFORMATION: Si RNA OST-4 sense

<400> SEQUENCE: 75
guuacuuugu gacaaaugat t                                              21

<210> SEQ ID NO 76
<211> LENGTH: 21
<212> TYPE: DNA
<213> ORGANISM: Artificial Sequence
<220> FEATURE:
<223> OTHER INFORMATION: Si RNA OST-4 antisense

<400> SEQUENCE: 76
ucauuuguca caaaguaact t                                              21

<210> SEQ ID NO 77
<211> LENGTH: 21
<212> TYPE: DNA
<213> ORGANISM: Artificial Sequence
<220> FEATURE:
<223> OTHER INFORMATION: Si RNA OST-4 sense

<400> SEQUENCE: 77
ccaaaugacu ggucaagaut t                                              21

<210> SEQ ID NO 78
<211> LENGTH: 21
<212> TYPE: DNA
<213> ORGANISM: Artificial Sequence
<220> FEATURE:
<223> OTHER INFORMATION: Si RNA OST-4 antisense

<400> SEQUENCE: 78
aucuugacca gucauuuggt a                                              21
```

METHOD OF DIAGNOSIS, PROGNOSTIC OR TREATMENT OF NEURODEGENERATIVE DISEASE

The present invention relates to a method of diagnosis, prognostic or treatment of neurodegenerative diseases, in particular Alzheimer's disease.

Neurodegenerative diseases, in particular Alzheimer's disease (AD), have a strongly debilitating impact on patient's life. Furthermore, these diseases constitute an enormous health, social, and economic burden. AD is the most widespread neurodegenerative disease globally and is estimated to afflict more than 27 million people worldwide. AD accounts for at least 50-70% of all dementia diagnosed clinically and it is probably the most devastating age-related neurodegenerative condition affecting about 10% of the population aver 65 years of age and up to 50% over age 85. The age of onset of AD may vary within a range of 50 years, with early-onset AD occurring in people younger than 65 years of age, and late-onset of AD occurring in those older than 65 years. About 10% of all cases suffer from early-onset AD, with only 1-2% being familial, mutant based, inherited cases, the remaining 98-99% are sporadic in where non mutations are associated to the disease. Clinically, AD is a progressive disease that is associated with early deficits in memory formation and ultimately leads to the complete erosion of higher cognitive function. The cognitive disturbance includes, among other things, memory impairment, aphasia, agnosis and the loss of executive functioning. A characteristic feature of the pathogenesis of AD is the selective vulnerability of particular brain regions and subpopulations of nerve cells to the degenerative process. Specifically, the cortex temporal lobe region and the hippocampus are affected early and more severely during the progression of the disease. On the other hand, neurons within other brain regions, as the cerebellum, remain largely intact and are protected from neurodegeneration Annals of Neurology 1981, 10:184-192). Currently, there is no cure for AD, nor is there an effective treatment to halt its progression. AD ante-mortem diagnosis is still non possible in blood or plasma samples and unfortunately none of the biomarkers presently available in cerebrospinal fluid (CSF) are able to accomplish a differential AD diagnosis from other Tauopathies and in a single-handedly.

Pathologically, AD is characterized by two brain lesions, called senile plaques and neurofibrillary tangles (NFT), which accumulate respectively Aβ peptides and the microtubule-associated Tau protein (MAPT). These neuropathological hallmarks have given origin to two corresponding hypothesis of the neurodegenerative process, the 'Aβ/amyloid cascade hypothesis' and the 'Tau-phosphorylation/NFT hypothesis'. In the 'Aβ/amyloid cascade hypothesis', the Aβ peptide evolves from the cleavage of the amyloid precursor protein (APP) by β/γ-secretases complexes, which associate presenilins-1 or -2 (PS-1 or PS-2), leading typically to the formation of a 42 amino acid peptide (Aβ42), which rapidly aggregates outside the cells forming the characteristic amyloid plaques. There are rare examples of early-onset AD which have been attributed to genetic defects in the genes for APP, PS-1, and PS-2.

The second hallmark of AD involves Tau protein, which after been abnormally phosphorylated, aggregates in the brain of Alzheimer's patients to form paired helical filaments (PHFs) and neurofibrillary tangles (NFT) (Iqbal K, Liu F, Gong C X, Grundke-Iqbal I. Tau in Alzheimer disease and related tauopathies. Curr Alzheimer Res December; 7(8):656-664). The Tau protein abnormal phosphorylation and NFTs formation and accumulation in brain has shown to directly correlate with the pathological, biochemical and clinical evolution of the disease. Prognostic and specific markers characteristics of AD remain to be found because of their big interest on prognosis, early diagnosis, and differential diagnosis of AD from related tauopathies (CSF, plasma, saliva or other easily obtainable body fluids).

One of the first characteristic of in vivo NFTs formation in the brain of patients suffering Alzheimer's disease (AD), or other tauopathies, is the abnormal phosphorylation of Tau at specific amino acid residues that are not phosphorylated under physiological conditions (Iqbal, Liu et al; Acta Neuropathol; 118(1):53-69; Gong and Iqbal, 2008; Curr Med Chem 15(23): 2321-8). It has been suggested that the first consequence of Tau abnormal phosphorylation is its detachment from microtubules, which might result in synapses impairment and cognition decline. Once Tau is detached, phosphorylation can continue at the newly accessible microtubule binding domains, the resulting over-phosphorylated Tau aggregates to then oligomerize and form NFT. This Tau oligomerization and subsequent aggregation in to NFTs inside cells is the second consequence of Tau hyperphosphorylation. This can then possibly affect a number of cell processes to finally kill cells and form ghost NFTs (ghost tangles) largely detected in AD's brains. Abnormal phosphorylation of Tau also induces the aggregation of normal Tau, which is effectively found in NFT together with the hyperphosphorylated protein, but in minor proportion (Biochem Soc Trans 38(4): 962-6). Interestingly, the phosphorylated-Tau aggregation kinetics, the aggregates architecture, and the aggregates localization in brains regions differ between the different tauopathies, possibly as the result of a Tau differential mutations effect in different brain regions, or of other factors that remain to be elucidated. Importantly, non Tau mutations are implicated in AD.

Although the aggregation of phosphorylated Tau into NFTs has been considered central to the disease, different studies in animal models involving Tau mutations have suggested the importance of Tau phosphorylation over NFT formation and truncation (Garcia-Sierra, Mondragon-Rodriguez et al. 2008, J Alzheimers Dis 14:401-409.). For instance, in transgenic *drosophila*, neural accumulation of the abnormally phosphorylated Tau leaded to neurodegeneration in the absence of NFT formation (Wittmann, Wszolek et al. 2001; Science 293:711-714). In an inducible P301L-Tau mutation in a transgenic mouse model, cognitive improvement was observed when abnormally hyperphosphorylated Tau was suppressed though NFT continued to form (Santacruz, Lewis et al. 2005; Science 309:476-481). In 3×TgAD mice, reduction of soluble Aβ and soluble abnormally phosphorylated Tau, but not of soluble aβ alone, ameliorated cognitive decline (Oddo, Vasilevko et al. 2006; J Biol Chem 281:39413-39423). These data suggest that the hyperphosphorylated Tau protein is involved in behavioral impairment and neuronal loss. Importantly, although in most animal models abnormal Tau phosphorylation is associated to mutations in the Tau gene MAPT (Vandrovcova, Anaya et al.; Curr Alzheimer Res 7:726-734), these mutations are absent in AD, allowing the assumption that hyperphosphorylation may also result from Tau mutational independent factors, which remain to be clarified.

In AD patients, the several kinases responsible of Tau abnormal phosphorylation are expressed at same levels than in healthy individuals and non mutations of any of these proteins have been reported in the disease. Thus, it has been assumed that hyperphosphorylation might be induced by conformational changes in the Tau protein with resultant exposition of the amino acid residues involved in its phosphorylation. These 'pathologic' conformational changes seem to be a requisite for the kinases action (Hiraoka et al., 2004, Biochem Biophys Res Commun 315:659-663; Biochem Biophys Res Commun 2004 Mar. 12; 315(3):659-663). Among the neural kinases that directly phosphorylate Tau and are therefore considered as important therapeutic targets, are neuronal cyclin-dependent kinase 5 (cdk5 or NCLK), glycogen synthase kinase-3β (GSK-3β), and microtubule affinity regulating kinase (MARK). (Mazanetz and Fischer, 2007, Nat Rev Drug Discov 6:464-479; Hanger et al., 2009, Trends Mol Med 15:112-119). Interesting, in brain of non-AD people, these kinases are not able to abnormally phosphorylate Tau suggesting that Tau conformational changes do not occur, or if they exist is in very lower and not pathologic levels. Regardless of their significance in disease, to date, kinase inhibitors, phosphatase activators and NFT dissociation agents have not given real positive results to stop or to regress the disease suggesting that abnormal phosphorylation of Tau is the point of non-return on the pathology. Thus, one of the priorities in the AD field is to clarify the mechanism of the MAPT gene mutation-independent abnormal phosphorylation of Tau protein (Gong and Iqbal, 2008; Curr Med Chem 15:2321-2328).

It has been demonstrated, in vitro, that heparin enables Tau to acquire a conformation in which abnormal phosphorylation sites are exposed (Paudel and Li, 1999, J Biol Chem 274:8029-8038). Moreover, NMR spectroscopy experiments have demonstrated that heparin induces conformational changes exposing the Thr231 residue to kinases responsible to its abnormal phosphorylation (Sibille et al., 2006, Biochemistry 45:12560-12572). The Thr231 residue is among the first residues in the protein been abnormally phosphorylated during the AD disease evolution. Heparin and other anionic macromolecules have also been shown to promote phosphorylation of Tau by a number of protein kinases (J Protein Chem. 1995 February; 14(2):95-105. Song J S, Yang S D; Yang S D, Yu J S, Shiah S G, Huang J J. J Neurochem. 1994 October; 63(4):1416-25).

Heparin and heparan sulfates (HS) belong to the family of polyanionic sulfated glycans named glycosaminoglycans (GAGs). HS chains are formed of a repeating disaccharide unit composed of an uronic acid linked to an N-acetyl glucosamine (GlcNAc). During biosynthesis, the elongating disaccharide chain follows several modifications including epimerization by a C5-epimerase transforming the uronic acid (GlcA) into iduronic acid (IdoA), and various regioselective sulfations assured by different sulfotransferases (Sandwall et al., 2010; Glycobiology; 20(5):533-41) including NDSTs (N-deacetyl-O-sulfotransferases), HS2ST (2-OST), HS6ST (6-OST) and HS3ST (3-OST), which respectively introduce sulfates groups at the 2-O-position of the IdoA, at the 6-O-position of GlcN or at the 3-O-position of the GlcN. A well orchestrated expression of the various sulfotransferases results in a well cell controlled diversity of HS sequences. HS are well recognized to play important biological roles as regulators of the functions of a family of proteins known as heparin binding proteins (HBP), which include several growth factors, matrix proteins, cytokines, etc. The structures and regulatory activities of HS are basically exerted through specific sulfation of the HS chains at positions N-2-O, and 6-O. The 3-O-position has only been directly related to anticoagulation and virus infection. Interestingly, these HS structures are highly constant in tissues but vary from one tissue to another to appropriately fit each tissue function. However, HS structures and functions have shown to considerably change with aging (Huynh M B et al., Neurobiol Aging. 2011 Oct. 27), with pathology or after tissue injury (Huynh M B et al., J Biol Chem. 2012). Compared to other sulfated positions, very low 3-O-sulfation levels can be sufficient to exert targeted biological activities as anticoagulation. 3-O-sulfation is not necessary for any recognized growth factor or cytokine activity regulation, not important for any mechanical function of HS in the extracellular matrix, thus not necessary for any trophic activity or HS.

Among the HS sulfotransferases, NDST, 2-OST, and 6-OST are the most commonly expressed and their activity results in the production of HS sulfated structures that regulate the activities of growth factors. 3-OST (HS3ST) accounts for about 0.5% of the total sulfate in an HS chain. The large number of genes in the vertebrate 3-OST family suggests functional heterogeneity, such that the ability of a cell type to generate specific fine structures HS, and thus to modulate pathological events. This might depend on the expression of specific isoformes which produces different sulfated disaccharides. 3-OST-1 produces the trisulfated GlcA-GlcNS3S±6S unit essential to the antithrombin (AT)-binding domain. 3-OST-2 forms trisulfated GlcA2S/IdoA2S-GlcNS3S (TriS unit) and the—tetrasulfated GlcA2S/IdoA2S-GlcNS3S6S unit (TetraS unit). 3-OST-3A and -3B, having identical catalytic domains, form trisulfated IdoA2S-GlcNH$_2$3 S±6S units. 3-OST-5 produces trisulfated HexA-GlcNS3S6S, TriS unit, and/or the TetraS unit.

The biomarker research for AD has significantly advanced in recent years. The body fluids such as cerebrospinal fluid (CSF), plasma, and urine are considered as important sources for the AD biomarker development. However, to date, only CSF can reflect biochemical changes that occur inside the brain because of its direct contact with the brain extracellular space. Thus far, three CSF biomarkers, Aβ42, total Tau (t-Tau), and phosphorylated-Tau (p-Tau), have been found to have the highest diagnostic potential (de Souza L C et al.; J Neurol Neurosurg Psychiatry; 82(3):240-6). In case of disease, hyper-phosphorylated Tau is found outside the cell, and in cerebrospinal fluid (CSF), even if Tau is normally considered to be an intracellular protein. Biomarkers of inflammation and oxidative stress are among the other sources. Unfortunately, none of the biomarkers presently available are able to accomplish the disease diagnosis single-handedly and monitoring more than one biomarker at the same time is suggested to be suitable for detecting the disease progression (Anoop et al, International Journal of Alzheimer's Disease 2010).

SH-SY5Y cells are a cell line of human neuroblastomes largely used in research. Differentiation of SH-SY5Y with retinoic acid allows accessibility to cells with neural-like phenotype with long neurites suitable as an in vitro model of AD (Datki Z et al.; Neurobiol Dis 2004; 17(3):507-15). The abnormal phosphorylation of Tau can be induced in these cells by two different approaches: (i) by a Tau-mutational-dependent approach using cells stably transfected with the human Tau protein containing the P301L mutation characteristic of frontotemporal dementia (FTDP-17) (Hutton et al., 1998, Nature 393:702-705), one of the most common tauopathies characterized by the P301L mutations in the Tau-encoding gene MAPT; and (ii) by a mutational-independent-approach based in $H_2O_2$ stressed cells which also generates Tau hyperphosphorylation as result of oxidative stress (Reynolds C H et al.; J Neurochem. 2000 April; 74(4):1587-95). The $H_2O_2$ induced phosphorylation has been reported to be possibly induced by stress-activated kinases as c-Jun N-terminal kinase (JNK) and p38, which are members of the mitogen-activated protein (MAP) kinase family and take part in signaling cascades initiated by various forms of stress. These kinases targets include the microtubule-associated protein Tau (Reynolds C H J Neurochem. 2000 April; 74(4):1587-95).

To assist in the elucidation of pathogenic mechanisms of AD and related disorders, genetically modified mice, flies, fish and worms have been developed, which reproduce aspects of the human histopathology, such as tauopathy with characteristic Tau abnormal phosphorylation and NFT formation. Recently, Paquet et al. introduced a zebrafish model of taupathy with genetic tractability in combination with a translucent embryo allowing imaging of disease progression at cellular and subcellular levels in the living animal. These features of the zebrafish model system make it useful for drug screening and other types of applied research (Paquet et al., 2009, J Clin Invest 119:1382-1395).

The Paquet's model of tauopathy reproduces the Tau-P301L mutation in the Tau-encoding gene MAPT found in patients with FTD with Parkinsonism linked to chromosome 17 (FTDP-17), a tauopathy characterized by the production of high levels of abnormally phosphorylated Tau in brain. Paquet optimized the transgenic expression of the human protein in zebrafish neurons by a newly designed Gal4-upstream activating sequence-based (Gal4/UAS-based) vector system, which also greatly facilitates identification of the transgenic fish by a simultaneously expressed fluorescent reporter.

Most Tau-directed drug discovery programs are in early research stages and are considerably less advanced than Aβ-focused programs. However, recent notable failures in pivotal clinical trials with agents aimed to reduce the Aβ burden in the brains of patients with Alzheimer's disease, underline the need to pursue other therapeutic approaches, including those that reduce the levels of pathological Tau.

One of the aims of the invention is to provide a composition for its use in the treatment or the prevention of neurodegenerative diseases.

Another aim of the invention is to provide a method of diagnosis or prognostic a neurodegenerative disease, in particular Alzheimer's disease, by means of 3-O-sulfotransferase 2 or 4 gene or protein or glycanic product in tissue, CSF or blood.

Another aim of the invention is to provide a kit for the implementation of said method of diagnosis or prognostic of a neurodegenerative disease, in particular Alzheimer's disease.

Another aim of the invention is to provide a method of treating or preventing a neurodegenerative disease, in particular Alzheimer's by means of a compound decreasing the expression level of 3-OST-2 and/or -4 genes or inhibiting said genes or the activity of their products.

Still another aim of the invention is to provide a method of treating or preventing a neurodegenerative disease, in particular Alzheimer's disease, by means of a compound decreasing the level of heparan sulfate, in particular 3-O-sulfated heparan sulfate, notably 3-O-sulfated heparan sulfate disaccharides.

Still another aim of the invention is to provide a method of treating or preventing a neurodegenerative disease, in particular Alzheimer's disease, by means of a compound decreasing the level of heparan sulfate with sulfation in position 3 of glucosamine residues.

Still another aim of the invention is to provide a method of treating or preventing a neurodegenerative disease, in particular Alzheimer's disease, by means of a compound decreasing the level of the phosphorylation of protein Tau.

Still another aim of the invention is to provide a method for in vitro screening for a modulator of a neurodegenerative disease, in particular Alzheimer's disease.

Still another aim of the invention is to provide a method for in vivo screening for a modulator of a neurodegenerative disease, in particular Alzheimer's disease.

Still another aim of the invention is to provide a composition liable to be used in the treatment or prevention of a neurodegenerative disease, in particular Alzheimer's disease.

The present invention relates to a composition comprising at least one agent which directly or indirectly affects an activity and/or a level of:
  a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  b) at least one transcription product of a gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  c) at least one translation product of said genes, said products being set forth respectively by SEQ ID NO: 2 and 4, and/or
  d) a fragment or derivative or variant of said gene or said transcription or translation product, and/or
  e) heparan sulfate, in particular 3-O-sulfated heparan sulfate, notably 3-O-sulfated heparan sulfate disaccharides, and/or
  f) abnormal phosphorylation of the Tau protein and/or total Tau protein, compared to a reference value,
for its use in the treatment or the prevention of a neurodegenerative disease, advantageously a Tauopathy, in particular Alzheimer's disease, provided that said neurodegenerative disease is different from a prion disease.

By the expression "at least one agent which directly or indirectly affects an activity and/or a level of" it must be understood a unique agent liable to affect said activity and/or level of said gene and/or of said transcription product and/or of said translation product and/or of heparan sulfate, in particular of 3-O-sulfated heparan sulfate and/or of the abnormal phosphorylation of the Tau protein and/or total Tau protein.

It must also be understood two or more different agents liable to affect said activity and/or level of at least one of the target defined above, i.e. said gene and/or of said transcription product and/or of said translation product and/or of heparan sulfate, in particular of 3-O-sulfated heparans, notably 3-O-sulfated heparan sulfate disaccharide, and/or of the abnormal phosphorylation of the Tau protein and/or total Tau protein.

In all the description:

The terms heparin sulphate (or sulfate) or heparan sulphate (or sulfate) or HS can be used and have the same meaning.

3-O-sulfated heparan sulfate disaccharides are obtained after heparinases I-III digestion of heparan sulfate.

The terms heparin-glucosamine 3-O-sulfotransferase (2 or 4) or heparan sulfate (glucosamine) 3-O-sulfotransferase (2 or 4) have the same meaning. Both enzymes can also be named 3-OST-2 and 3-OST-4 or 3OST2 and 3OST4, HS3ST2 and HS3ST4, h3-OST-2 and h3-OST-4; heparan sulfate 3-O-sulfotransferase 2; heparan sulfate 3-O-sulfotransferase 4; heparan sulfate D-glucosaminyl 3-O-sulfotransferase 2; heparan sulfate D-glucosaminyl 3-O-sulfotransferase 4;

heparan sulfate glucosamine 3-O-sulfotransferase 2; heparan sulfate glucosamine 3-O-sulfotransferase 4.

The singular forms "a", "an", and "the" as used herein and in the claims include plural reference unless the context dictates otherwise. For example, "a cell" means as well a plurality of cells, and so forth. The term "and/or" as used in the present specification and in the claims implies that the phrases before and after this term are to be considered either as alternatives or in combination. For instance, the wording "determination of a level and/or an activity" means that either only a level, or only an activity, or both a level and an activity are determined. The term "level" as used herein is mean to comprise a gage of, or a measure of the amount of, or a concentration of a transcription product, for instance an mRNA, or a translation product, for instance a protein or polypeptide, or the product of the activity of an enzyme, for instance a glycanic structure with specific sulfation. The term "activity" as used herein shall be understood as a measure for the ability of a transcription product or a translation product, or the capacity of an enzyme, to produce a biological effect or a measure for a level of biologically active molecules, or a measure of a level of specifically sulfated sequences or disaccharides obtained from a glycan. The term "activity" also refers to enzymatic activity or the biological activity and/or pharmacological activity which refer to binding, antagonization, repression, blocking or neutralization. The term "level" and/or "activity" as used herein further refer to gene expression levels or gene activity, or an enzyme activity levels measured by the amount of product that it produces. Gene expression as used herein further refers to gene expression levels or gene activity. Gene expression can be defined as the utilization of the information contained in a gene by transcription and translation leading to the production of a gene product, protein, peptide, or glycan. Enzyme activity as used herein further refers to the measure of the enzyme product. "Dysregulation" shall comprise either upregulation or downregulation of gene expression. A gene product comprises either RNA or protein and is the result of expression of a gene. A gene product in a glycanic molecule comprises either the level of a particular glycosidic substitution, as sulfation, introduced from the protein activity. The amount of a gene product can be used to measure how active a gene is. The amount of an enzyme product can be used to measure how active the enzyme is. The term "gene" as used in the present specification and in the claims comprises both coding regions (exons) as well as non-coding regions (e.g. non-coding regulatory elements such as promoters or enhancers, introns, leader and trailer sequences). A gene product comprises either RNA or protein and is the results of expression of a gene. The enzyme activity can be used to measure how the enzyme is present. The term "ORF" is an acronym for "open reading frame" and refers to a nucleic acid sequence that does not possess a stop codon in at least one reading frame and therefore can potentially be translated into a sequence of amino-acids. "Regulatory elements" shall comprise inducible and non-inducible promoters, enhancers, operators, and other elements that drive and regulate gene expression. The term "fragment" as used herein is meant to comprise e.g. an alternatively spliced, or truncated, or otherwise cleaved transcription product or translation product. For a glycanic molecule, the term fragment as used herein is meant to comprise e.g. glycan of any size produced in vivo or in vitro by the action of endogenous or exogenous enzymes that can digest it to produce oligosaccharides or shorter fragments going until disaccharides. The term "derivative" as used herein refers to a mutant, or an RNA-edited, or an enzymatic digestion product or a chemically modified or otherwise altered translation product. For the purpose of clarity, a derivative transcript, for instance, refers to a transcript having alterations in the nucleic acid sequence such as single or multiple nucleotide deletions, insertions, or exchange such as single or multiple nucleotide deletions, insertions, or exchanges. A "derivative" may be generated by processes such as altered phosphorylation, or glycosylation, or acetylation, or lipidation, or altered signal peptide cleavage or the other types of maturation cleavage. These processes may occur post-translationally. The term "modulator" as used in the present invention and in the claims refers to a molecule capable of changing or altering the level and/or the activity of a gene, or a transcription product of a gene, or a translation product of a gene, or the product of an enzyme. Preferably, a "modulator" is capable of changing or altering the biological activity of a transcription product or a translation product of a gene. Said modulation, for instance, may be an increase or a decrease in the biological activity and/or pharmacological activity, and/or enzymatic activity, a change in binding characteristics, or any other change or alteration in the biological functional or immunological properties of said translation product of a gene. A "modulator" refers to a molecule which has the capacity to either enhance or inhibit, thus to "modulate", a functional property of an enzyme, and/or ion channel subunit or an ion channel, to "modulate" binding, antagonization, repression, blocking, neutralization or sequestration of an ion channel subunit and to "modulate" activation, agonization and upregulation. "Modulation" will be also used to refer to the capacity to affect the biological activity of a cell. The term "modulator", "agent", "reagent", or "compound" refer to any substance, chemical, composition or extract that have a positive of negative biological effect on a cell, tissue, body fluid, or within the context of any biological system, or any assay system examined. They can be agonist, antagonist, partial agonist or inverse agonist of a target. They may be nucleic acids, natural or synthetic peptides or protein complexes, or fusion proteins, natural or synthetic glycans, or glycan mimetics, as heparan sulfate mimetics. They may also be antibodies, organic or inorganic molecules or compositions, small molecules, drugs and any combinations of any of said agents above. They may be used for testing, for diagnostic or for therapeutic purposes. Such modulators, agents, reagents or compounds can be factors present in cell culture media. The term "oligonucleotide primer" or "primer" refer to short nuclei acid sequences which can anneal to give a target polynucleotide by hybridization of the complementary base pairs and can be extended by a polymerase. They may be chosen to be specific to a particular sequence or they may be randomly selected, e.g. they will prime all possible sequences in a mix. The length of primers used herein may vary from 10 nucleotides to 300 nucleotides. "Probes" are short nucleic acid sequences of the nucleic acid sequence described and disclosed herein or sequences complementary therewith. They may comprise full length sequences, or fragments, derivatives, isoforms, or variants of a given sequence. The identification of hybridization complexes between a "probe" and an assayed sample allows the detection of the presence of the other similar sequences within that sample. As used herein, "homolog or homology" is a term used in the art to describe the relatedness of a nucleotide or peptide sequence to another nucleotide or peptide sequence, which is determined by the degree of identity and/or similarity between sequences compared. In the art, the term "identity" and "similarity" mean the degree of polypeptide or polynucleotide sequence relatedness which are determined by matching a query sequence and other sequences of preferably the dame type (nucleic acid or protein sequence) with each other. Preferred computer program methods to calculate and determine "identity" and "similarity" include, but are not limited to GCC BLAST (Basic Local Alignment Search Tool), BLASTN 2.0 (Gixh W., http://blast.wustl.edu), FASTA, and GCG GelMerge which determines and aligns a pair of contings with the longest overlap. The term "variant" as used herein refers to any polypeptide or protein, in reference to polypeptides and proteins disclosed in the present invention, in which one or more amino acids are added and/or within the native amino acid sequences of the native polypeptides or proteins of the present invention. Furthermore, the term "variant" shall include any shorter or longer version of a polypeptide or protein. "variants" shall also comprise a sequence that has at least 80% sequence identity, more preferably at least 90% sequence identity, more preferably at least 95% sequence identity with the amino acid sequence of HS3ST2 and HS3ST4, of SEQ ID NO. 2 and SEQ ID NO. 4. "Variants" of a protein molecule include, for example, proteins with conservative amino acids substitutions in highly conservative regions. "Proteins and polypeptides" of the present invention includes variants, fragments and chemicals derivatives of the protein comprising the amino acid sequence of HS3ST2 and/or HS3ST4, of SEQ ID NO. 2 and SEQ ID NO. 4. Sequences variations shall be included wherein a codon is replaced with another codon due to alternative base sequences, but the amino acid sequence translated by the DNA sequence remains unchanged. This known in the art phenomenon is called redundancy of the set of codons which translate specific amino acids. Included shall be such exchange of amino acids which would have no effect on the functionality, such as arginine for lysine, valine for leucine, asparagine for glutamine. Proteins and polypeptides can be included which can be isolated from nature or be produced by recombinant and/or synthetic means. Native proteins or polypeptides refer to naturally-occurring truncated or secreted forms, naturally occurring forms (e.g. splice-variants and naturally occurring allelic variants). The term "isolated" as used herein is considered to refer to molecules or substances which have been changed and/or that are removed from their natural environment, i.e. isolated from a tissue, from a cell or from a living organism in which they normally occur, and that are separated or essentially purified from the coexisting components with which they are found to be associated in nature, it is also said that they are "non-native". This notion further means that the sequences encoding such molecules can be linked in the natural state and such molecules can be produced by recombinant and/or synthetic means (non-native). Even of for said purposes those sequences may be introduced into living or non-living organisms by methods known to those skilled in the art, and even if those sequences are still present in said organisms, they are still considered to be isolated, to be non-native. In the present invention, the terms "risk", "susceptibility", and "predisposition" are tantamount and are used with respect to the probability of developing a neurodegenerative disease, preferably Alzheimer's disease.

The term "AD" shall mean Alzheimer's disease. "AD-type neuropathology" as used herein refers to neuropathological, neurophysiological, histopathological and clinical hallmarks as described in the instant invention and as commonly known from state-of-the-art literature (Ballard C et al., Lancet 2011; 377(9770):1019-1031). The term "Braak stage" or "Braak staging" refers to the classification of brains according to the criteria proposed by Braak and Braak (Braak H, Neurosci Lett. 1986; 65:351-355). On the basis of the distribution of neurofibrillary tangles and neuropil threads, the neuropathologic progression of AD is divided into six stages (stage 0 to 6). In the present invention Braak stages 0 to 2 represent healthy control persons ("control"), and Braak stages 4 to 6 represent persons suffering from AD ("AD-patients"). The value obtained from said "controls" are the "reference values" representing a "known health status" and the values obtained from said "AD patients" are the "reference values" representing a "known disease status". Braak stage 2 may represent either a healthy control persons or an AD patient. The higher the Braak stage the more likely is the possibility to display the symptoms of AD. For a neuropathological assessment, i.e. an estimation of the probability that pathological changes of AD are the underlying cause of dementia, a recommendation is given by Braak H (www.alzforum.org).

Neurodegenerative diseases or disorders according to the present invention comprises AD, Parkinson disease, Huntington's disease, amylotrophic lateral sclerosis, Pick's disease, frontotemporal dementia, progressive nuclear palsy, corticobasal degeneration, cerebro-vascular taupathies, and mild cognitive impairment. Conditions involving neurodegenerative processes are, for instance, aged-related macular degeneration, narcolepsy, motor neuron diseases, and traumatic nerve injury and repair, and multiple sclerosis.

Prion diseases are excluded from the scope of the invention.

The expression "heparan sulfate" refers to total heparan sulfate comprising heparan sulfate liable to bind to Tau protein and heparan sulfate that do not bind to Tau protein.

In particular heparan sulfate liable to bind to Tau protein consists in 3-O-sulfated heparan sulfate.

By total Tau protein is meant phosphorylated Tau protein, aggregated or not, and non phosphorylated Tau protein.

The inventors have thus found that the modulation of the activity and/or the level of one or two enzymes (3-OST-2 and/or 3-OST-4) and/or of 3-O-sulfated heparan sulfate and/or of the abnormal phosphorylation of the Tau protein and/or total Tau protein, was liable to treat or prevent a neurodegenerative disease.

The present invention relates to a composition comprising at least one agent which directly or indirectly affects an activity and/or a level of:
  a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  b) at least one transcription product of a gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  c) at least one translation product of said genes, said products being set forth respectively by SEQ ID NO: 2 and 4, and/or
  d) a fragment or derivative or variant of said gene or said transcription or translation product, and/or
  e) heparan sulfate, in particular 3-O-sulfated heparan sulfate, notably 3-O-sulfated heparan sulfate disaccharides, and/or
  f) abnormal phosphorylation of the Tau protein and/or total Tau protein, compared to a reference value,
for its use in the treatment or the prevention of a neurodegenerative disease, advantageously a Tauopathy, in particular Alzheimer's disease, provided that said neurodegenerative disease is different from a prion disease, and provided that when said agent directly or indirectly affects the activity and/or the level:
- of heparan sulfate, or
- of abnormal phosphorylation of the Tau protein and/or total Tau protein, therefore, both activities and/or levels of heparan sulfate and of abnormal phosphorylation of the Tau protein and/or total Tau protein are affected by said agent, or the activity and/or the level of at least one other element chosen among said gene, said transcription product of said genes, said translation product of said genes, or said fragment or derivative or variant of said gene or said transcription or translation product is also affected.

Thus in this embodiment, several cases listed below can be encountered, i.e. said agent affects the activity and/or the level of:
- only one element chosen among: a), b), c) or d); that means that the activity and/or level of only e) or only f) is therefore excluded;
- two elements chosen among the following couples: a-b, a-c, a-d, a-e, a-f, b-c, b-d, b-e, b-f, c-d, c-e, c-f, d-e, d-f, or e-f;
- three elements chosen among the following: a-b-c, a-b-d, a-b-e, a-b-f, a-c-d, a-c-e, a-c-f, a-d-e, a-d-f, a-e-f, b-c-d, b-c-e, b-c-f, b-d-e, b-d-f, b-e-f, c-d-e, c-d-f or d-e-f;
- four elements chosen among the following: a-b-c-d, a-b-c-e, a-b-c-f, a-c-d-e, a-c-d-f, a-d-e-f, b-c-d-e, b-c-d-f, c-d-e-f;
- five elements chosen among the following: a-b-c-d-e, a-b-c-d-f, a-b-d-e-f, a-c-d-e-f;
- six elements chosen among the following: a-b-c-d-e-f.

In an advantageous embodiment, the present invention relates to a composition for its use in the treatment or the prevention of a neurodegenerative disease as defined above, comprising at least one agent which directly or indirectly affects an activity and/or a level of:
- a) at least one gene selected from the group consisting of the nucleotidic sequences set forth by SEQ ID NO: 1 and SEQ ID NO: 3 and coding for an heparin-glucosamine 3-O-sulfotransferase-2 and -4 respectively, and/or
- b) at least one transcription product of a gene selected from the group consisting of the nucleotidic sequences set forth by SEQ ID NO: 1 and SEQ ID NO: 3 and coding for an heparin-glucosamine 3-O-sulfotransferase-2 and -4 respectively, and/or
- c) at least one translation product of said genes, said products being set forth respectively by SEQ ID NO: 2 and 4, and
- d) abnormal phosphorylation of the Tau protein and/or total Tau protein, and wherein the neurodegenerative disease is an Alzheimer's disease.

The inventors have further found that the modulation of the activity and/or the level of one or two enzymes (3-OST-2 and/or 3-OST-4) and/or of 3-O-sulfated heparan sulfate and of the abnormal phosphorylation of the Tau protein and/or total Tau protein, was liable to treat or prevent an Alzheimer's disease.

In an advantageous embodiment, the present invention relates to a composition for its use in the treatment or the prevention of a neurodegenerative disease as defined above, comprising at least one agent which directly or indirectly affects an activity and/or a level of:
- a) at least one gene selected from the group consisting of the nucleotidic sequences set forth by SEQ ID NO: 1 and SEQ ID NO: 3 and coding for an heparin-glucosamine 3-O-sulfotransferase-2 and -4 respectively, and/or
- b) at least one transcription product of a gene selected from the group consisting of the nucleotidic sequences set forth by SEQ ID NO: 1 and SEQ ID NO: 3 and coding for an heparin-glucosamine 3-O-sulfotransferase-2 and -4 respectively, and/or
- c) at least one translation product of said genes, said products being set forth respectively by SEQ ID NO: 2 and 4, and
- d) heparan sulfate, in particular 3-O-sulfated heparan sulfate, notably 3-O-sulfated heparan sulfate disaccharides, and
- e) abnormal phosphorylation of the Tau protein and/or total Tau protein.

and wherein the neurodegenerative disease is an Alzheimer's disease.

In an advantageous embodiment, the present invention relates to a composition for its use in the treatment or the prevention of a neurodegenerative disease as defined above, comprising at least one agent which directly or indirectly affects an activity and/or a level of:
- a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
- b) at least one transcription product of a gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
- c) at least one translation product of said genes, said products being set forth respectively by SEQ ID NO: 2 and 4, and
- d) heparan sulfate, in particular 3-O-sulfated heparan sulfate, notably 3-O-sulfated heparan sulfate disaccharides, and wherein the neurodegenerative disease is an Alzheimer's disease.

In an advantageous embodiment, the present invention relates to a composition for its use in the treatment or the prevention of a neurodegenerative disease as defined above, comprising one agent which directly or indirectly affects an activity and/or a level of abnormal phosphorylation of the Tau protein and/or total Tau protein, and wherein the neurodegenerative disease is a Tauopathy.

In Taupathy, the abnormal phophorylation of Tau protein is the result of mutations or deletions in the Tau protein gene without changing the expression of 3-OST-2 and -4 gene(s).

The inventors have further found that the modulation of the activity and/or the level of the abnormal phosphorylation of the Tau protein and/or total Tau protein by an agent that do modulate or affect the level of the abnormal phosphorylation of Tau protein was liable to treat or prevent a Tauopathy including Alzheimer's disease.

In an advantageous embodiment, the present invention relates to a composition for its use in the treatment or the prevention of a neurodegenerative disease as defined above, comprising at least one agent which directly or indirectly affects an activity and/or a level of:
- a) heparan sulfate, in particular 3-O-sulfated heparan sulfate, notably 3-O-sulfated heparan sulfate disaccharides, and,
- b) abnormal phosphorylation of the Tau protein and/or total Tau protein, and wherein the neurodegenerative disease is a Tauopathy, in particular an Alzheimer's disease.

In an advantageous embodiment, said heparan sulfate, the activity and/or level of which is affected by said at least one agent that also affects the activity and/or level of abnormal phosphorylation of the Tau protein and/or total Tau protein, refers to heparan sulfate liable to bind to Tau protein.

The Inventors have still further found that an agent liable to compete with the binding of heparan sulfate to Tau protein, was liable to modulate or affect the activity and/or level of heparan sulfate and abnormal phosphorylation of the Tau protein and/or total Tau protein and therefore liable to treat Tauopathy, in particular Alzheimer's disease, by preventing the release of phosphorylated Tau protein outside the cell and thus the spreading of phosphorylated Tau from a cell to another one.

In an advantageous embodiment, the present invention relates to a composition for its use in the treatment or the prevention of a neurodegenerative disease as defined above, comprising at least one agent which directly or indirectly affects an activity and/or a level of:
  a) at least one translation product of said genes, said products being set forth respectively by SEQ ID NO: 2 and 4, and,
  b) heparan sulfate, in particular 3-O-sulfated heparan sulfate, notably 3-O-sulfated heparan sulfate disaccharides, and,
  c) abnormal phosphorylation of the Tau protein and/or total Tau protein
and wherein the neurodegenerative disease is a Tauopathy, in particular an Alzheimer's disease.

In an advantageous embodiment, the present invention relates to a composition for its use in the treatment or the prevention of a neurodegenerative disease as defined above, comprising at least one agent which directly or indirectly affects an activity and/or a level of:
  a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and,
  b) heparan sulfate, in particular 3-O-sulfated heparan sulfate, notably 3-O-sulfated heparan sulfate disaccharides, and,
  c) abnormal phosphorylation of the Tau protein and/or total Tau protein
and wherein the neurodegenerative disease is a Tauopathy, in particular an Alzheimer's disease.

In an advantageous embodiment, the present invention relates to a composition for its use in the treatment or the prevention of a neurodegenerative disease as defined above, comprising at least one agent which directly or indirectly affects an activity and/or a level of:
  a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  b) at least one transcription product of a gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  c) at least one translation product of said genes, said products being set forth respectively by SEQ ID NO: 2 and 4, and d) heparan sulfate, in particular 3-O-sulfated heparan sulfate, notably 3-O-sulfated heparan sulfate disaccharides,
and wherein the neurodegenerative disease is an Alzheimer's disease.

In an advantageous embodiment, the present invention relates to a composition for its use in the treatment or the prevention of a neurodegenerative disease as defined above, wherein said at least one agent is selected from the group consisting of:
  a) a polysaccharide or an oligosaccharide having a molecular weight from about 2000 Daltons to about 20 000 Daltons, preferably of about 20 000 Daltons, in particular an heparan sulfate mimetic, such as F6 molecule, D6, D4, E5, CR36, HM 100 or HM 2602, or fucoidan or pentosan polysulfate, or in particular a pentasaccharide, such as Arixtra® (fondaparinux), fucoidan, or pentosan polysulfate, and/or low molecular weight heparins as enoxaparin (Lovenox®), and/or ultralow molecular weight heparins, and/or
  b) an oligonucleotide, in particular a siRNA such as a siRNA selected from the list consisting of: sense siRNA set forth by SEQ ID NO: 71 and antisense siRNA set forth by SEQ ID NO: 72, sense siRNA set forth by SEQ ID NO: 73 and antisense siRNA set forth by SEQ ID NO: 74, sense siRNA set forth by SEQ ID NO: 75 and antisense siRNA set forth by SEQ ID NO: 76, sense siRNA set forth by SEQ ID NO: 77 and antisense siRNA set forth by SEQ ID NO: 78, or a morpholino antisense oligonucleotide, in particular selected from the group consisting of SEQ ID NO: 5 and SEQ ID NO: 6, and/or
  c) a small molecule, inhibitor of heparin and heparan sulfate actions, such as protamine or protamine sulfate.

Said at least one agent can be polysaccharide or an oligosaccharide and these terms refer to the application of oligosaccharides or polysaccharides competitors of the product of the genes by oral, intravenous, sublingual and/or nasal administration. In general, glycan therapy is based in the use of HS analogues as dextran derivatives or different sizes and substitutions as those cited in (WO00/05270), or fucoidan derivates of different sizes, in where carboxylates and/or sulfates and/or hydrophobic moieties have been introduced, and still pentosan polysulfate and other natural glycosaminoglycans as heparan sulfate, chondroitin sulfates (-A, -B, -C, -D, -E), keratan sulfate (Masato Hasegawa et al., J Biol. Chem. Vol. 272, No. 52, pp. 33118-33124, 1997). Such glycans should act as: molecular replacement of the product of the target gene and/or as modulators of endogenous protein activity, and/or as competitors of the product of the target gene.

Such glycans can be administered alone or preferably in association with other therapy as gene therapy. Production of biologically active sulfated polysaccharides or oligosaccharides derivatives that can mimic and/or compete and/or replace endogenous polysaccharides or oligosaccharides product of the target genes has been reported (WO00/05270). Such production methods include the introduction of carboxylates and/or sulfates and/or hydrophobic moieties in dextran, cellulose, or other glycans or polyalcohols of different sizes (WO00/05270).

Polysaccharides or oligosaccharides can also be heparin of low molecular weight, such as enoxaparin (Lovenox®) or an ultralow molecular weight heparins.

The term heparan sulfate mimetic (HM) refers to fragments of glycosaminoglycan (GAG) mimicking molecule of the general structure (I) defined below:

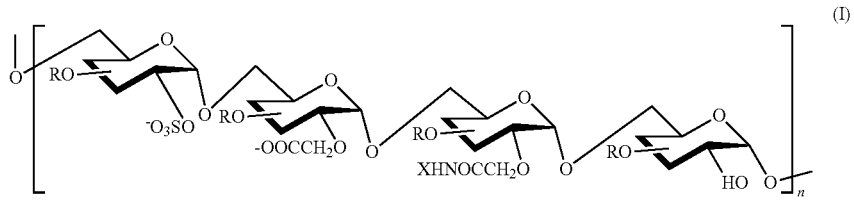

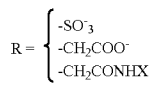

Wherein:

n represents an integer comprised from 1 to 10 000, in particular 1 to 200.

R represents $SO_3^-$, $CH_2CO_2$ or $-CH_2CONHX$ in which NHX represents:

a linear or branched $C_1$-$C_{10}$ alkylamine, in particular a n-octylamine or t-octylamine, a benzylamine, an amino-acid (L, D or racemic), esterified or not on the carboxylic moiety by an alkyl or a benzyl, in particular L-phenylalanine methyl ester (L-Phe(OMe)) or a L-tyrosine methyl ester or a L-histidine methyl ester or their corresponding D-analogues.

HM can be prepared as described in Papy-Garcia et al. (Papy-Garcia D et al., Macromolecules, 2005, 38, 4647-4654) from dextran molecules having different molecular weight, in particular from dextran T40, T10 or T5 (MW=40000, 10000 or 5000 respectively).

In particular, heparan sulfate mimetic refers to the above formula (I), wherein:

n represents an integer comprised from 1 to 50, in particular 1 to 40, in particular 1 to 30, in particular 1 to 20, in particular 1 to 10

R is as defined above wherein NHX is benzylamine or an amino acid such as L-Phe(OMe), and the degree of substitution is the following:

0.2-1.5 CM, 0-0.5 (benzylamine or AA), 0.2-1.5 S wherein CM corresponds to the carboxymethyl groups (possible 20 to 150% contents), S corresponds to the sulfate groups (possible 20-150% contents); benzylamine or AA (corresponds to said amino-acid): possible 0-50% substitutions).

In particular, the HM corresponds to:

F6 molecule (prepared from T5, NHX=L-Phe(OMe)) having the following degree of substitution:

0.61 CM, 0.15 L-Phe(OMe), 0.7 S,

D4 molecule (prepared from T10) having the following degree of substitution:

0.75 CM, 0.2 S;

wherein CM corresponds to the carboxymethyl groups (75% from possible 20 to 150% contents), S corresponds to the sulfate groups (20% from possible 20-150% contents); L-Phe(OMe) is present at 0% from possible 0-50% substitutions.

E5 molecule (prepared from T10) having the following degree of substitution:

0.5 CM, 1.0S wherein CM corresponds to the carboxymethyl groups (50% from possible 20 to 150% contents), S corresponds to the sulfate groups (100% from possible 20-150% contents); L-Phe(OMe) is present at 0% from possible 0-50% substitutions.

D6 molecule (prepared from T0.5, NHX=L-Phe(OMe)) having the following degree of substitution:

0.60 CM, 0.2 L-Phe(OMe), 1.2 S wherein CM corresponds to the carboxymethyl groups (60% from possible 20 to 150% contents), S corresponds to the sulfate groups (120% from possible 20-150% contents); L-Phe(OMe) is present at 20% from possible 0-50% substitutions.

wherein CM corresponds to the carboxymethyl groups (61% from possible 20 to 150% contents), S corresponds to the sulfate groups (70% from possible 20-150% contents); L-Phe(OMe) is present at 15% from possible 0-50% substitutions.

CR 36 molecule (prepared from T10, NHX=L-Phe(OMe)) having the following degree of substitution:

0.59 CM, 0.22 L-Phe(OMe), 0.83 S wherein CM corresponds to the carboxymethyl groups (59% from possible 20 to 150% contents), S corresponds to the sulfate groups (83% from possible 20-150% contents); L-Phe(OMe) is present at 22% from possible 0-50% substitutions.

HM100 (fucoidan) 0.50 CM, 0.20 Ac, 1 S (Ac=acetate group)

wherein CM corresponds to the carboxymethyl groups (50% from possible 20 to 150% contents), S corresponds to the sulfate groups (100% from possible 20-150% contents); acetate group is present at 10% from possible 0-50% substitutions.

HM 2602 (prepared from T40, NHX=benzylamine) having the following degree of substitution 0.88 CM, 0.20 benzylamine, 0.66 S.

wherein CM corresponds to the carboxymethyl groups (88% from possible 20 to 150% contents), S corresponds to the sulfate groups (66% from possible 20-150% contents); benzylamide group is present at 20% from possible 0-50% substitutions.

The term pentasaccharide refers to a synthetic heparin mimetic constituted of five glycosidic units and being sulfated, such as a part of heparin being liable to bind to antithrombin.

In particular, said pentasaccharide is Arixtra® (fondaparinux) of the following formula:

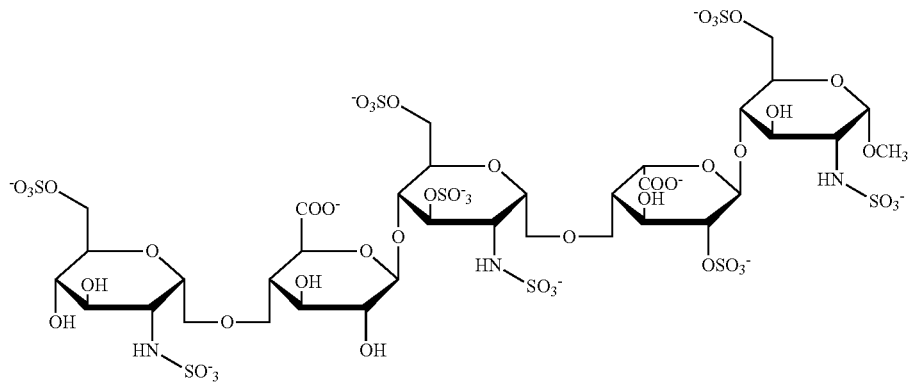

Said polysaccharide, oligosaccharide or pentasaccharide are liable to compete with heparin sulfate or 3-O-sulfated heparin sulfate and to bind to the Tau protein with a better affinity than endogen brain GAG allowing reducing the abnormal phosphorylation of Tau protein.

Thus, said polysaccharide, oligosaccharide or pentasaccharide is liable to treat Tauopathies as well as Alzheimer's disease.

Said polysaccharide, oligosaccharide or pentasaccharide can be administered at a dose comprised from about 1.5 mg/Kg to about 50 mg/Kg by intravenous route or by another route as oral at about 50 mg/kg to about 500 mg/kg, in particular 100 to 200 mg/kg or i.v. at an appropriate dosage for said routes.

In an advantageous embodiment, said polysaccharide, oligosaccharide or pentasaccharide can be administered at a daily dose comprised from about 100 mg to about 3.5 g by intravenous route or by another route as oral at about 3.5 g to about 50 g, in particular 7.5 to 15 g or i.p . . . at an appropriate dosage for said routes.

Said at least one agent can also be an oligonucleotide and this term designates a siRNA liable to interfer with the expression of the genes set forth by SEQ ID NO:1 and 3, such as those defined above, at least one miRNA, at least one shRNA comprising one sense sequence and one antisense of a siRNA as defined above, a morpholino antisense oligonucleotide, or a combination of the above, liable to silencing the 3-OST-2 or -4 gene and thus to modify or block said gene expression.

Thus the transcription of said gene is decreased by at least 50% of the original value or totally blocked as well as the translation leading thus to a decrease of 3-OST-2 and -4 level and thus to a decrease of the abnormal phosphorylated Tau protein.

Small hairpin RiboNucleic Acid (shRNA) are double-stranded molecules comprising both the sense and the antisense strand of a siRNA, said sense and antisense strands being linked by a linker. These molecules form a hairpin, and the linker is eliminated to allow the liberation of a siRNA.

In an advantageous embodiment, said shRNA is comprised in a vector, said vector comprising nucleic acid sequences allowing the expression of said shRNA.

In advantageous embodiments, the method comprises the application of per se known methods of gene therapy and/or antisense nucleic acid technology to administer said agent or agents. In general, gene therapy includes several approaches: molecular replacement of a mutated gene, edition of a new gene resulting in the synthesis of a therapeutic protein, and modulation of endogenous cellular gene expression by recombinant expression methods or by drugs. Gene-transfert techniques are described in detail (see e.g. Behr Acc Chem Res 1993, 26: 274-278 and Mulligan, Science 1993, 260: 926-931) and include direct gene-transfer techniques employing biological vectors (like recombinant viruses, especially retroviruses and lentivirus) or model liposomes, or techniques based on transfection with DNA coprecipitation with polycations, cell membrane perturbation by chemical (solvents, detergents, polymers, enzymes) or physical means (mechanic, osmotic, thermic, electric shocks) or cell membrane penetrating peptides. The postnatal gene transfer into the central nervous system has been described in detail (see e.g. Wolff, Curr opin neurobiol 1993, 3:743-748).

In particular, the invention features a methods of rating or preventing a neurodegenerative disease by means of antisense nucleic acid therapy, i.e. the down-regulation of an inappropriately expressed or defective gene by the introduction of antisense nucleic acids or derivatives thereof into certain critical cells (see e.g. Gillespie, DN&P 1992, 5: 389-395; Agrawal and Akhtar, Trends Biotechnol 1995, 13: 197-199; Crooke, Biotechnology 1992, 10: 882-6). Apart from hybridization strategies, the application of ribozymes, i.e. RNA molecules that act as enzymes, destroying RNA that carries the message of disease has also been described (see e.g. Barinaga, Science 1993, 262: 1512-1514). In preferred embodiments, therapeutic antisense nucleic acids or derivatives thereof are directed against transcripts of a gene coding for HS3ST2 and/or HS3ST4. It is preferred that cells of the central nervous system, preferably the brain, of a subject treated in such a way. Cell penetration can be performed by known strategies such as coupling of antisense nucleic acids and derivatives thereof to carrier particles, or the above described techniques. Strategies for administering targeted therapeutic oligo-deoxynucleotides are known to those of skill in the art (see e.g. Wickstrom, Trends Biotechnol 1992, 10:281-287). In some cases, delivery can be performed by mere intracranial (intra-ventricular) application. Further approaches are directed to intracellular expression of antisense RNA. In this strategy, cells are transformed ex vivo with a recombinant gene that directs the synthesis of an RNA that is complementary to a region of target nucleic acid. Therapeutic use of intracellularly expressed antisense RNA is procedurally similar to gene therapy. A recent developed method of regulating the intracellular expression of genes by the use of double-stranded RNA, known variously as RNA interference (RNAi), can be another effective approach for nucleic acid therapy (Hannon, Nature 418: 244-251).

The treatment of a neurodegenerative disease such as Alzheimer's disease or Tauopathy different from an Alzheimer's disease, can thus be carried out by gene therapy by administering said oligonucleotide by means of a vector or an exosome (van den Boom J G et al., Nat Biotechnol. 2011 April; 29(4):325-6).

The treatment of Alzheimer's disease can also been carried out by a double therapy comprising as first therapy the gene therapy and as second therapy the protection of the extracellular medium inducing cell recovery by means of an heparin mimetic.

Said oligonucleotide can be administered at a dose comprised from 0.1 to 1 mM, in particular 0.5 mM by intraveinous or by intraventricular routes.

Said oligonucleotide can also be administered by another route as oral, i.p . . . at appropriate dosage for said routes.

Said at least one agent can be also a small molecule, and by this expression it must be understood, a molecule liable to inhibit heparin and heparan sulfate actions that inhibit the heparin capacity to induce conformational change in Tau protein leading to the abnormal phosphorylation of Tau protein.

Protamine or protamine sulfate are small nuclear protein rich in arginine and are antagonists of heparin with an immediate action after intravenous administration.

Other inhibitors of 3-O-sulfatation or inhibitors of sulfotransferases of heparan sulfate can be used in this embodiment, in particular those described in Razi, N et al. (J Biol Chem 1995, 270, 11267-75); in Rath, V. L. et al. (Drug Discov Today 2004, 9, 1003-11) or in Seko, A. et al. (J Inorg Biochem 2009, 103, 1061-6).

Inhibitors of heparan sulfate and heparan sulfate sulfotransferases described in US20100048638 can also be used.

In an advantageous embodiment, the present invention relates to a composition for its use in the treatment or the prevention of a neurodegenerative disease as defined above, wherein said at least one agent is selected from the group consisting of:
  a) an heparan sulfate mimetic of formula (I) above defined, in particular an heparan sulfate mimetic of formula (II), in particular F6 molecule, CR36, HM 100 or HM 2602, or fucoidan or pentosan polysulfate, or a pentasaccharide, such as Arixtra® (fondaparinux), fucoidan, or pentosan polysulfate, and/or low molecular weight heparins as enoxaparin (Lovenox®), and/or ultralow molecular weight heparins, and/or
  b) a siRNA such as a siRNA selected from the list consisting of: sense siRNA set forth by SEQ ID NO: 71 and antisense siRNA set forth by SEQ ID NO: 72, sense siRNA set forth by SEQ ID NO: 73 and antisense siRNA set forth by SEQ ID NO: 74, sense siRNA set forth by SEQ ID NO: 75 and antisense siRNA set forth by SEQ ID NO: 76, sense siRNA set forth by SEQ ID NO: 77 and antisense siRNA set forth by SEQ ID NO: 78, or a morpholino antisense oligonucleotide, in particular selected from the group consisting of SEQ ID NO: 5 and SEQ ID NO: 6, and/or
  c) a small molecule, inhibitor of heparin and heparan sulfate actions, selected from the group consisting of protamine or protamine sulfate.

In another aspect, the present invention relates to an in vitro method of diagnosis or prognostic or follow-up of a neurodegenerative disease in a subject, or determining whether a subject is at increased risk of developing said neurodegenerative disease, comprising determining a level and/or an activity of:
  a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  b) at least one transcription product of a gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  c) at least one translation product of said genes, said products being set forth respectively by SEQ ID NO: 2 and 4, and/or
  d) a fragment or derivative or variant of said gene or said transcription or translation product, and/or
  e) heparan sulfate, in particular 3-O-sulfated heparan sulfate, notably 3-O-sulfated heparan sulfate disaccharides, and/or
  f) abnormal phosphorylation of the Tau protein and/or total Tau protein,
  in a sample of a biological fluid previously obtained from said subject and comparing said level and/or said activity to a respective reference value representing a known disease or health status,
  an increased level and/or activity of at least one of said gene and/or said transcription product and/or said translation product and/or said heparan sulfate, in particular said 3-O-sulfated heparan sulfate and/or said abnormal phosphorylation of the Tau protein and/or total Tau protein in the subject sample being indicative of a neurodegenerative disease or a risk of developing said neurodegenerative disease, advantageously a Tauopathy, in particular Alzheimer's disease, provided that said neurodegenerative disease is different from a prion disease.

The Inventors have thus found that the level of expression of the 3-OST-2 (HS3ST2) and/or 3-OST-4 (HS3ST4) gene was highly increased in neurodegenerative diseases, in particular in Alzheimer's disease leading thus to higher 3-O-sulfated HS or with heparin-like HS structures.

Thus the level and/or the activity of one or both gene(s) as set forth by SEQ ID NO: 1 and 3 are increased but also one of or both transcription product(s) of said genes are increased as well as one or both translation product(s) of said genes, that is proteins as set forth by SEQ ID NO: 2 and 4.

3-OST-2 and 4 being responsive of the 3-O-sulfation of heparan sulfate, the level of said 3-O-sulfated heparan sulfate is also highly increased, inducing conformational changes in Tau protein leading to the abnormal phosphorylation of Tau protein.

Thus the detection in a biological fluid of an increased level and/or activity compared to a reference value of at least one of these constituents will lead to the diagnostic or prognostic of a neurodegenerative disease, in particular an Alzheimer's disease or a Tauopathy different from Alzheimer's disease.

In an advantageous embodiment, the biological fluid is the extracellular medium of any cell culture, in particular neurons in primary culture but also the blood, the plasma, the serum, urine or the cerebrospinal fluid (CSF).

In preferred embodiments, measurement of the level of transcription products of a gene coding for HS3ST2 and/or HS3ST4 is performed in a sample obtained from a subject using a quantitative PCR-analysis with primer combinations to amplify said genes specific sequences from cDNA obtained by reverse transcription of RNA extracted from a sample of a subject. Primer combinations are given in "Examples" of the instant invention, but also other primers generated from the sequences as disclosed in the instant invention can be used. A Northern blot with probes specific for said genes can also be applied. It might further be preferred to measure transcription products by means of chip-based micro-array technologies. These techniques are known to those of ordinary skill in the art (see Sambrook and Russell, *Molecular Cloning: A Laboratory Manual*, Cold Spring Harbor Laboratory Press, Cold Spring Harbor, N.Y., 2001; Schena M., *Microarray Biochip technology*, Eaton Publishing, Natick, Mass., 2000).

Furthermore, a level and/or an activity of a translation product or a glycanic product of the translation product, of a gene coding for HS3ST2 and/or HS3ST4 and/or of a fragment, or derivative, or variant of said translation product, and/or a level of activity of said translation product and/or of a fragment, or derivative, or variant of said translation product, and/or a level of activity of said glycanic product, can be detected using an immunoassay, an activity assay, a chromatographic assay, a spectrometric assay as mass spectroscopy, and/or a binding assay. These assays can measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, *Using Antibodies: A Laboratory Manual*, Cold Spring Harbor Laboratory Press, Cold Spring Harbor, N.Y., 1999 and Edwards R, *Immunodiagnostics: A Practical Approach*, Oxford University Press, Oxford; England, 1999). All these detection techniques may also be employed in the format of microarrays, protein-arrays, antibody microarrays, tissue microarrays, electronic biochip or protein-chip based technologies (see Schena M., *Microarray Biochip Technology*, Eaton Publishing, M A, 2000).

In an advantageous embodiment, the level, or the activity, or both said level and said activity of (i) a transcription product of a gene coding for HS3ST2 and/or HS3ST4, and/or of (ii) a translation product of a gene coding for HS3ST2 and/or HS3ST4, and/or of (iii) a fragment, or derivative, or variant of said transcription or translation product, and/or of (iv) a glycanic product, or a fragment of this glycanic product, issue from the translation product of the gene coding for HS3ST2 and/or SH3ST4, in a series of samples taken from said subject over a period of time is compared, in order to monitor the progression of said disease. In further preferred embodiments, said subjects receive a treatment prior to one or more of said sample gatherings. In yet another preferred embodiment, said level and/or activity is determined before and after said treatment of said subject.

In an advantageous embodiment, the present invention relates to an in vitro method as defined above, wherein said neurodegenerative disease is a Tauopathy including Alzheimer disease.

In an advantageous embodiment, the present invention relates to an in vitro method wherein said neurodegenerative disease is a Tauopathy as defined above, and wherein the level of the abnormal phosphorylation of Tau protein and/or total Tau protein is increased by at least 10% compared to a respective reference value.

The reference value is given by a value obtained with patients that are not afflicted by a Tauopathy or another neurodegenerative disease or a disease affecting the level of abnormal phosphorylation of Tau protein.

The reference value can take a variety of forms. It can be single cut-off value, such as for instance a median or mean or the 75th, 90th, 95th or 99th percentile of a population. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quartiles, the lowest quartile being individuals with the lowest risk and the highest quartile being individuals with the highest risk.

The predetermined value can vary among particular populations selected, depending on their habits, ethnicity, genetics etc.

In an advantageous embodiment, the abnormal phosphorylation of Tau protein is increased by at least 20% compared to said reference value.

In an advantageous embodiment, the abnormal phosphorylation of Tau protein is increased by at least 30% compared to said reference value.

In an advantageous embodiment, the abnormal phosphorylation of Tau protein is increased by at least 40% compared to said reference value.

In an advantageous embodiment, the abnormal phosphorylation of Tau protein is increased by at least 50% compared to said reference value.

In an advantageous embodiment, the abnormal phosphorylation of Tau protein is increased by at least 60% compared to said reference value.

In an advantageous embodiment, the abnormal phosphorylation of Tau protein is increased by at least 70% compared to said reference value.

In an advantageous embodiment, the abnormal phosphorylation of Tau protein is increased by at least 80% compared to said reference value.

In an advantageous embodiment, the abnormal phosphorylation of Tau protein is increased by at least 90% compared to said reference value.

In an advantageous embodiment, the abnormal phosphorylation of Tau protein is increased by at least 100% compared to said reference value.

In an advantageous embodiment, the level and/or activity of abnormal phosphorylation of Tau protein compared to said reference value is increased by at least 10%, 20%, 30%, 40%, 50%, 60%, 70%, 80%, 90% or 100% and the level and/or activity of total Tau protein compared to said respective reference value is increased by at least 10%, 20%, 30%, 40%, 50%, 60%, 70%, 80%, 90% or 100%.

In an advantageous embodiment, the present invention relates to an in vitro method of diagnosis or prognostic or follow-up of a neurodegenerative disease in a subject, or determining whether a subject is at increased risk of developing said neurodegenerative disease, comprising determining a level and/or an activity of:
  a) at least one gene selected from the group consisting of the nucleotidic sequences set forth by SEQ ID NO: 1 and SEQ ID NO: 3 and coding for an heparan sulfate glucosamine 3-O-sulfotransferase 2 and 4 respectively, and/or
  b) at least one transcription product of a gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or c) at least one translation product of said genes, said products being set forth respectively by SEQ ID NO: 2 and 4, and/or d) a fragment or derivative or variant of said gene or said transcription or translation product, and/or e) heparan sulfate, in particular 3-O-sulfated heparan sulfate, notably 3-O-sulfated heparan sulfate disaccharide, and/or f) abnormal phosphorylation of the Tau protein and/or total Tau protein, in a sample of a biological fluid previously obtained from said subject and comparing said level and/or said activity to a respective reference value representing a known disease or health status, an increased level and/or activity of at least one of said gene and/or said transcription product and/or said translation product and/or said heparan sulfate, in particular said 3-O-sulfated heparan sulfate and/or said abnormal phosphorylation of the Tau protein and/or total Tau protein in the subject sample being indicative of a neurodegenerative disease or a risk of developing said neurodegenerative disease, advantageously a tauopathy, in particular Alzheimer's disease, provided that said neurodegenerative disease is different from a prion disease, and provided that when said activity and/or the level determined is the one of:

heparan sulfate, or of abnormal phosphorylation of the Tau protein and/or total Tau protein, therefore, the activities and/or levels heparan sulfate and abnormal phosphorylation of the Tau protein and/or total Tau protein are both determined, or the activity and/or the level of at least one other element chosen among said gene, said transcription product of said genes, said translation product of said genes, or said fragment or derivative or variant of said gene or said transcription or translation product is also determined.

Thus in this embodiment, several cases listed below can be encountered, i.e. said determination of the activity and/or the level consists of:

only one element chosen among: a), b), c) or d); that means that the activity and/or level of only e) or only f) is therefore excluded;

two elements chosen among the following couples: a-b, a-c, a-d, a-e, a-f, b-c, b-d, b-e, b-f, c-d, c-e, c-f, d-e, d-f, or e-f;

three elements chosen among the following: a-b-c, a-b-d, a-b-e, a-b-f, a-c-d, a-c-e, a-c-f, a-d-e, a-d-f, a-e-f, b-c-d, b-c-e, b-c-f, b-d-e, b-d-f, b-e-f, c-d-e, c-d-f or d-e-f;

four elements chosen among the following: a-b-c-d, a-b-c-e, a-b-c-f, a-c-d-e, a-c-d-f, a-d-e-f, b-c-d-e, b-c-d-f, c-d-e-f;

five elements chosen among the following: a-b-c-d-e, a-b-c-d-f, a-b-d-e-f, a-c-d-e-f;

six elements chosen among the following: a-b-c-d-e-f.

In an advantageous embodiment, the present invention relates to an in vitro method wherein said neurodegenerative disease is a Tauopathy as defined above, wherein said biological fluid is the CSF and said activity and/or level of:

a) said gene selected from the group consisting of the nucleotidic sequences set forth by SEQ ID NO: 1 and SEQ ID NO: 3 and coding for an heparin-glucosamine 3-O-sulfotransferase 2 and 4 respectively, and b) said transcription product of a gene selected from the group consisting of the nucleotidic sequences set forth by SEQ ID NO: 1 and SEQ ID NO: 3 and coding for an heparin-glucosamine 3-O-sulfotransferase, and c) said translation product of said genes, said products being set forth respectively by SEQ ID NO: 2 and 4, and d) a fragment or derivative or variant of said gene or said transcription or translation product, and e) heparan sulfate, in particular 3-O-sulfated heparan sulfate, notably 3-O-sulfated heparan sulfate disaccharides, in a subject are substantially the same as the respective reference value and, said activity and/or level of abnormal phosphorylation of the Tau protein and/or total Tau protein is increased in said subject compared to said respective reference value, in particular by at least 10%.

In Taupathies other than Alzheimer disease, abnormal Tau phosphorylation results from mutations or deletions in the MAPT gene, this induces the abnormal phosphorylation of Tau protein, in this case no increase of 3-OSTs is observed. In sporadic Alzheimer disease there is not mutations or deletions in the Tau protein, increase of 3-OST is observed. Thus, detection of 3-OSTs allows making a differential diagnostic and/or prognostic between dementias including genetic Taupathies and sporadic Alzheimer disease.

The detection of only the abnormal phosphorylation of Tau protein and/or total Tau protein without detecting any other increased level and/or activity of the other constituents cited above allows thus the differential diagnostic and/or prognostic of a Tauopathy other than Alzheimer's disease.

The expression "substantially the same" means that the measured level can vary with respect to the reference value because of the individual variation among particular populations selected, depending on their habits, ethnicity, genetics etc. Therefore, the measured level can be plus/minus 10%, plus/minus 5% or plus/minus 2.5% of the reference value.

In an advantageous embodiment, the present invention relates to an in vitro method as defined above, wherein said neurodegenerative disease is an Alzheimer's disease.

In an advantageous embodiment, the present invention relates to an in vitro method wherein said neurodegenerative disease is an Alzheimer's disease as defined above, and wherein said level of the transcription product of the gene set forth by SEQ ID NO: 1 is increased by at least 100% as determined by real time PCR.

In this embodiment, only the 3-OST-2 gene is implicated in the disease, the level of the 3-OST-4 gene is substantially unchanged.

In an advantageous embodiment, said level of the transcription product of the gene set forth by SEQ ID NO: 1 is increased by at least 200% as determined by real time PCR.

In an advantageous embodiment, said level of the transcription product of the gene set forth by SEQ ID NO: 1 is increased by at least 300% as determined by real time PCR.

In an advantageous embodiment, said level of the transcription product of the gene set forth by SEQ ID NO: 1 is increased by at least 400% as determined by real time PCR.

In an advantageous embodiment, the present invention relates to an in vitro method as defined above, wherein said neurodegenerative disease is an Alzheimer's disease and wherein said level of the transcription product of the gene set forth by SEQ ID NO: 3 is increased by at least 100% as determined by real time PCR.

In this embodiment, only the 3-OST-4 gene is implicated in the disease, the level of the 3-OST-2 gene is substantially unchanged.

In an advantageous embodiment, said level of the transcription product of the gene set forth by SEQ ID NO: 3 is increased by at least 200% as determined by real time PCR.

In an advantageous embodiment, said level of the transcription product of the gene set forth by SEQ ID NO: 3 is increased by at least 300% as determined by real time PCR.

In an advantageous embodiment, said level of the transcription product of the gene set forth by SEQ ID NO: 3 is increased by at least 400% as determined by real time PCR.

In an advantageous embodiment, the present invention relates to an in vitro method wherein said neurodegenerative disease is an Alzheimer's disease as defined above, and wherein said level of the transcription product of the gene set forth by SEQ ID NO: 1 is increased by at least 100% and said level of the transcription product of the gene set forth by SEQ ID NO: 3 is increased by at least 100% as determined by real time PCR.

In this embodiment, both 3-OST-2 and 3-OST-4 genes are implicated in the disease.

In an advantageous embodiment, said level of the transcription product of the gene set forth by SEQ ID NO: 1 is increased by at least 100% as determined by real time PCR and said level of the transcription product of the gene set forth by SEQ ID NO: 3 is increased by at least 200% as determined by real time PCR.

In an advantageous embodiment, said level of the transcription product of the gene set forth by SEQ ID NO: 1 is increased by at least 100% as determined by real time PCR and said level of the transcription product of the gene set forth by SEQ ID NO: 3 is increased by at least 300% as determined by real time PCR.

In an advantageous embodiment, said level of the transcription product of the gene set forth by SEQ ID NO: 1 is increased by at least 100% as determined by real time PCR and said level of the transcription product of the gene set forth by SEQ ID NO: 3 is increased by at least 400% as determined by real time PCR.

In an advantageous embodiment, said level of the transcription product of the gene set forth by SEQ ID NO: 1 is increased by at least 200% as determined by real time PCR and said level of the transcription product of the gene set forth by SEQ ID NO: 3 is increased by at least 100% as determined by real time PCR.

In an advantageous embodiment, said level of the transcription product of the gene set forth by SEQ ID NO: 1 is increased by at least 200% as determined by real time PCR and said level of the transcription product of the gene set forth by SEQ ID NO: 3 is increased by at least 200% as determined by real time PCR.

In an advantageous embodiment, said level of the transcription product of the gene set forth by SEQ ID NO: 1 is increased by at least 200% as determined by real time PCR and said level of the transcription product of the gene set forth by SEQ ID NO: 3 is increased by at least 300% as determined by real time PCR.

In an advantageous embodiment, said level of the transcription product of the gene set forth by SEQ ID NO: 1 is increased by at least 200% as determined by real time PCR and said level of the transcription product of the gene set forth by SEQ ID NO: 3 is increased by at least 400% as determined by real time PCR.

In an advantageous embodiment, said level of the transcription product of the gene set forth by SEQ ID NO: 1 is increased by at least 300% as determined by real time PCR and said level of the transcription product of the gene set forth by SEQ ID NO: 3 is increased by at least 100% as determined by real time PCR.

In an advantageous embodiment, said level of the transcription product of the gene set forth by SEQ ID NO: 1 is increased by at least 300% as determined by real time PCR and said level of the transcription product of the gene set forth by SEQ ID NO: 3 is increased by at least 200% as determined by real time PCR.

In an advantageous embodiment, said level of the transcription product of the gene set forth by SEQ ID NO: 1 is increased by at least 300% as determined by real time PCR and said level of the transcription product of the gene set forth by SEQ ID NO: 3 is increased by at least 300% as determined by real time PCR.

In an advantageous embodiment, said level of the transcription product of the gene set forth by SEQ ID NO: 1 is increased by at least 300% as determined by real time PCR and said level of the transcription product of the gene set forth by SEQ ID NO: 3 is increased by at least 400% as determined by real time PCR.

In an advantageous embodiment, said level of the transcription product of the gene set forth by SEQ ID NO: 1 is increased by at least 400% as determined by real time PCR and said level of the transcription product of the gene set forth by SEQ ID NO: 3 is increased by at least 100% as determined by real time PCR.

In an advantageous embodiment, said level of the transcription product of the gene set forth by SEQ ID NO: 1 is increased by at least 400% as determined by real time PCR and said level of the transcription product of the gene set forth by SEQ ID NO: 3 is increased by at least 200% as determined by real time PCR.

In an advantageous embodiment, said level of the transcription product of the gene set forth by SEQ ID NO: 1 is increased by at least 400% as determined by real time PCR and said level of the transcription product of the gene set forth by SEQ ID NO: 3 is increased by at least 300% as determined by real time PCR.

In an advantageous embodiment, said level of the transcription product of the gene set forth by SEQ ID NO: 1 is increased by at least 400% as determined by real time PCR and said level of the transcription product of the gene set forth by SEQ ID NO: 3 is increased by at least 400% as determined by real time PCR.

In an advantageous embodiment, the present invention relates to an in vitro method wherein said neurodegenerative disease is an Alzheimer's disease as defined above, and wherein said level of the translation product of the gene and set forth by SEQ ID NO: 2 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 and compared to a reference value is increased by at least 70% as determined by Western Blot, ELISA, mass spectrometry or immunohistochemistry methods.

In an advantageous embodiment, said level of the translation product of the gene set forth by SEQ ID NO: 2 and compared to a reference value is increased by at least 80% as determined by Western Blot, ELISA, mass spectrometry or immunohistochemistry methods.

In an advantageous embodiment, said level of the translation product of the gene set forth by SEQ ID NO: 2 and compared to a reference value is increased by at least 90% as determined by Western Blot, ELISA, mass spectrometry or immunohistochemistry methods.

In an advantageous embodiment, said level of the translation product of the gene set forth by SEQ ID NO: 2 and compared to a reference value is increased by at least 100% as determined by Western Blot, ELISA, mass spectrometry or immunohistochemistry methods.

The basal value in human CSF for 3-OST-2 is 60 pg/ml.

In an advantageous embodiment, said level of the translation product of the gene set forth by SEQ ID NO: 2 compared to said basal level is increased by at least 60% as determined by Western Blot, ELISA, mass spectrometry or immunohistochemistry methods in CSF.

In an advantageous embodiment, said level of the translation product of the gene set forth by SEQ ID NO: 2 compared to said basal level is increased by at least 70% as determined by Western Blot, ELISA, mass spectrometry or immunohistochemistry methods in CSF.

In an advantageous embodiment, said level of the translation product of the gene set forth by SEQ ID NO: 2 compared to said basal level is increased by at least 80% as determined by Western Blot, ELISA, mass spectrometry or immunohistochemistry methods in CSF.

In an advantageous embodiment, said level of the translation product of the gene set forth by SEQ ID NO: 2 compared to said basal level is increased by at least 90% as determined by Western Blot, ELISA, mass spectrometry or immunohistochemistry methods in CSF.

In an advantageous embodiment, said level of the translation product of the gene set forth by SEQ ID NO: 2 compared to said basal level is increased by at least 100% as determined by Western Blot, ELISA, mass spectrometry or immunohistochemistry methods in CSF.

In an advantageous embodiment, the present invention relates to an in vitro method wherein said neurodegenerative disease is an Alzheimer's disease as defined above, and wherein said level of the translation product of the gene and set forth by SEQ ID NO: 4 is increased by at least 50% as determined by Western Blot, ELISA, mass spectrometry or immunohistochemistry methods.

In an advantageous embodiment, said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 4 compared to a reference value is increased by at least 100% as determined by Western Blot, ELISA, mass spectrometry or immunohistochemistry methods.

The basal value in human CSF for 3-OST-4 is 60 pg/ml.

In an advantageous embodiment, said level of the translation product of the gene set forth by SEQ ID NO: 4 compared to said basal level is increased by at least 60% as determined by Western Blot, ELISA, mass spectrometry or immunohistochemistry methods in CSF.

In an advantageous embodiment, said level of the translation product of the gene set forth by SEQ ID NO: 4 compared to said basal level is increased by at least 70% as determined by Western Blot, ELISA, mass spectrometry or immunohistochemistry methods in CSF.

In an advantageous embodiment, said level of the translation product of the gene set forth by SEQ ID NO: 4 compared to said basal level is increased by at least 80% as determined by Western Blot, ELISA, mass spectrometry or immunohistochemistry methods in CSF.

In an advantageous embodiment, said level of the translation product of the gene set forth by SEQ ID NO: 4 compared to said basal level is increased by at least 90% as determined by Western Blot, ELISA, mass spectrometry or immunohistochemistry methods in CSF.

In an advantageous embodiment, said level of the translation product of the gene set forth by SEQ ID NO: 4 compared to said basal level is increased by at least 100% as determined by Western Blot, ELISA, mass spectrometry or immunohistochemistry methods in CSF.

In an advantageous embodiment, the present invention relates to an in vitro method wherein said neurodegenerative disease is an Alzheimer's disease as defined above, and wherein said level of the translation product of the gene and set forth by SEQ ID NO: 2 is increased by at least 50% as determined by ELISA or Western Blot and wherein said level of the translation product of the gene and set forth by SEQ ID NO: 4 is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said reference value for 3-OST-2 is the basal value for 3-OST-2 in human CSF and is 60 pg/ml and said reference value for 3-OST-4 is the basal value for 3-OST-2 in human CSF and is 60 pg/ml.

In an advantageous embodiment, the present invention relates to an in vitro method wherein said neurodegenerative disease is an Alzheimer's disease, wherein
said level of the transcription product of the gene set forth by SEQ ID NO: 1 is increased by at least 100% as determined by real time PCR and/or
said level of the transcription product of the gene set forth by SEQ ID NO: 3 is increased by at least 100% as determined by real time PCR and/or
said level of the translation product of the gene and set forth by SEQ ID NO: 2 is increased by at least 50% and/or
said level of the translation product of the gene and set forth by SEQ ID NO: 4 is increased by at least 50% as determined by Western Blot, ELISA, mass spectrometry or immunohistochemistry methods as defined above,
comprising further determining the level and/or activity of heparan sulfate, an increase of at least 50% of said level and/or activity compared to a reference value being indicative of Alzheimer's disease.

In an advantageous embodiment, said level and/or activity of heparan sulfate is further increased by 60% compared to said reference value.

In an advantageous embodiment, said level and/or activity of heparan sulfate is further increased by 70% compared to said reference value.

In an advantageous embodiment, said level and/or activity of heparan sulfate is further increased by 80% compared to said reference value.

In an advantageous embodiment, said level and/or activity of heparan sulfate is further increased by 90% compared to said reference value.

In an advantageous embodiment, said level and/or activity of heparan sulfate is further increased by 100% compared to said reference value.

The basal level of heparan sulfate in a control human hippocampus is about 0.5 µg/mg of wet tissue as determined by the dimethylmethylene blue (DMMB) assay (Huynh et al. Neurobiol Aging. 2012 33(5):1005.e11-22).

Considering that said reference value is said basal level, thus said level in Alzheimer's disease is increased by at least 50% in the hippocampus and the cortex.

In an advantageous embodiment, the level and/or activity of heparan sulfate is further increased by 60% compared to the basal level and/or activity in the hippocampus and the cortex.

In an advantageous embodiment, the level and/or activity of heparan sulfate is further increased by 70% compared to the basal level and/or activity in the hippocampus and the cortex.

In an advantageous embodiment, the level and/or activity of heparan sulfate is further increased by 80% compared to the basal level and/or activity in the hippocampus and the cortex.

In an advantageous embodiment, the level and/or activity of heparan sulfate is further increased by 90% compared to the basal level and/or activity in the hippocampus and the cortex.

In an advantageous embodiment, the level and/or activity of heparan sulfate is further increased by 100% compared to the basal level and/or activity in the hippocampus and the cortex.

In an advantageous embodiment, the present invention relates to an in vitro method wherein said neurodegenerative disease is an Alzheimer's disease, wherein
said level of the transcription product of the gene set forth by SEQ ID NO: 1 is increased by at least 100% as determined by real time PCR and/or
said level of the transcription product of the gene set forth by SEQ ID NO: 3 is increased by at least 100% as determined by real time PCR and/or
said level of the translation product of the gene and set forth by SEQ ID NO: 2 is increased by at least 50% and/or
said level of the translation product of the gene and set forth by SEQ ID NO: 4 is increased by at least 50% as determined by Western Blot, ELISA, mass spectrometry or immunohistochemistry methods as defined above,
comprising further determining the level and/or activity of heparan sulfate liable to bind to Tau protein, an increase of at least 50% of said level and/or activity compared to a reference value being indicative of Alzheimer's disease.

Several sulfated glycosaminoglycans and mimetics can bing Tau, this includes heparans sulfates, chondroitin sulfate, keratan sulfate and other sulfated polysaccharides from chemical synthesis as dextran sulfate and pentosan sulfates.

In an advantageous embodiment, the level and/or activity of heparan sulfate is further increased by 60% compared to said reference value.

In an advantageous embodiment, the level and/or activity of heparan sulfate is further increased by 70% compared to said reference value.

In an advantageous embodiment, the level and/or activity of heparan sulfate is further increased by 80% compared to said reference value.

In an advantageous embodiment, the level and/or activity of heparan sulfate is further increased by 90% compared to said reference value.

In an advantageous embodiment, the level and/or activity of heparan sulfate is further increased by 100% compared to said reference value.

In an advantageous embodiment, the level and/or activity of heparan sulfate is further increased by 110% compared to said reference value.

In an advantageous embodiment, the level and/or activity of heparan sulfate is further increased by 120% compared to said reference value.

In an advantageous embodiment, the level and/or activity of heparan sulfate is further increased by 130% compared to said reference value.

In an advantageous embodiment, the level and/or activity of heparan sulfate is further increased by 140% compared to said reference value.

In an advantageous embodiment, the level and/or activity of heparan sulfate is further increased by 150% or more compared to said reference value.

In an advantageous embodiment, said level and/or activity of heparan sulfate is determined in human hippocampus, cortex, CSF or blood.

The basal level of heparan sulfate in a control human hippocampus is about 0.5 µg/mg of wet tissue as determined by the dimethylmethylene blue (DMMB) assay described by Huynh et al. (Neurobiol Aging. 2012 33(5):1005.e11-22).

Considering that said reference value is said basal level, thus said level and/or activity of heparan sulfate is increased in Alzheimer's disease by 50% in the hippocampus.

In an advantageous embodiment, said level and/or activity of heparan sulfate is further increased by 60% compared to the basal level and/or activity in the hippocampus.

In an advantageous embodiment, said level and/or activity of heparan sulfate is further increased by 70% compared to the basal level and/or activity in the hippocampus.

In an advantageous embodiment, said level and/or activity of heparan sulfate is further increased by 80% compared to the basal level and/or activity in the hippocampus.

In an advantageous embodiment, said level and/or activity of heparan sulfate is further increased by 90% compared to the basal level and/or activity in the hippocampus.

In an advantageous embodiment, said level and/or activity of heparan sulfate is further increased by 100% compared to the basal level and/or activity in the hippocampus.

In an advantageous embodiment, said level and/or activity of heparan sulfate is further increased by 110% compared to the basal level and/or activity in the hippocampus.

In an advantageous embodiment, said level and/or activity of heparan sulfate is further increased by 120% compared to the basal level and/or activity in the hippocampus.

In an advantageous embodiment, said level and/or activity of heparan sulfate is further increased by 130% compared to the basal level and/or activity in the hippocampus.

In an advantageous embodiment, said level and/or activity of heparan sulfate is further increased by 140% compared to the basal level and/or activity in the hippocampus.

In an advantageous embodiment, said level and/or activity of heparan sulfate is further increased by 150% or more compared to the basal level and/or activity in the hippocampus.

In an advantageous embodiment, the present invention relates to an in vitro method wherein said neurodegenerative disease is an Alzheimer's disease, wherein
said level of the transcription product of the gene set forth by SEQ ID NO: 1 is increased by at least 100% as determined by real time PCR and/or
said level of the transcription product of the gene set forth by SEQ ID NO: 3 is increased by at least 100% as determined by real time PCR and/or
said level of the translation product of the gene and set forth by SEQ ID NO: 2 is increased by at least 50% and/or
said level of the translation product of the gene and set forth by SEQ ID NO: 4 is increased by at least 50% as determined by Western Blot, ELISA, mass spectrometry or immunohistochemistry methods as defined above,
comprising further determining the level and/or activity of 3-O-sulfated heparan sulfate, an increase of at least 50% of said level compared to a reference value being indicative of Alzheimer's disease.

The inventors have found that among the heparan sulfate, in particular the heparan sulfate liable to bind to Tau protein, the 3-O-sulfated-heparan sulfate are highly increased allowing thus to diagnose an Alzheimer's disease.

Said increase in Alzheimer's disease is observed in the hippocampus, cortex, CSF and blood.

In an advantageous embodiment, said level and/or activity of 3-O-sulfated heparan sulfate is further increased by 60% compared to said reference value.

In an advantageous embodiment, said level and/or activity of 3-O-sulfated heparan sulfate is further increased by 70% compared to said reference value.

In an advantageous embodiment, said level and/or activity of 3-O-sulfated heparan sulfate is further increased by 80% compared to said reference value.

In an advantageous embodiment, said level and/or activity of 3-O-sulfated heparan sulfate is further increased by 90% compared to said reference value.

In an advantageous embodiment, said level and/or activity of 3-O-sulfated heparan sulfate is further increased by 100% compared to said reference value.

In an advantageous embodiment, said level and/or activity of 3-O-sulfated heparan sulfate is further increased by 110% compared to said reference value.

In an advantageous embodiment, said level and/or activity of 3-O-sulfated heparan sulfate is further increased by 120% compared to said reference value.

In an advantageous embodiment, said level and/or activity of 3-O-sulfated heparan sulfate is further increased by 130% compared to said reference value.

In an advantageous embodiment, said level and/or activity of 3-O-sulfated heparan sulfate is further increased by 140% compared to said reference value.

In an advantageous embodiment, said level and/or activity of 3-O-sulfated heparan sulfate is further increased by 150% or more compared to said reference value.

The basal level of 3-O-sulfated heparan sulfate in a control human hippocampus is about 1 ng/mg of wet tissue as determined by the dimethylmethylene blue (DMMB) assay.

In an advantageous embodiment, the level and/or activity of 3-O-sulfated heparan sulfate is further increased by 60% compared to the basal level and/or activity in the hippocampus.

In an advantageous embodiment, the level and/or activity of 3-O-sulfated heparan sulfate is further increased by 100% compared to the basal level and/or activity in the hippocampus.

In an advantageous embodiment, the level and/or activity of 3-O-sulfated heparan sulfate is further increased by 110% compared to the basal level and/or activity in the hippocampus.

In an advantageous embodiment, the level and/or activity of 3-O-sulfated heparan sulfate is further increased by 120% compared to the basal level and/or activity in the hippocampus.

In an advantageous embodiment, the level and/or activity of 3-O-sulfated heparan sulfate is further increased by 130% compared to the basal level and/or activity in the hippocampus.

In an advantageous embodiment, the level and/or activity of 3-O-sulfated heparan sulfate is further increased by 140% compared to the basal level and/or activity in the hippocampus.

In an advantageous embodiment, the level and/or activity of 3-O-sulfated heparan sulfate is further increased by 150% or more compared to the basal level and/or activity in the hippocampus.

In an advantageous embodiment, said 3-O-sulfated heparan sulfate is selected from the trisulfated GlcA2S/IdoA2S-GlcNS3S and the tetrasulfated GlcA2S/IdoA2S-GlcNS3S6S unit forms that correspond to ΔUA2S-GlcNS3S and ΔUA2S-GlcNS3S6S obtained after digestion of heparan sulfates by heparinases I, II, and III, and the biological fluid is CSF. Chemical methods as nitrous acid treatment (Huynh et al. Neurobiol Aging. 2012 33(5):1005.e11-22) can also be used to produce HS disaccharides.

A representative structure of 3-O-sulfated heparan sulfate is the following:

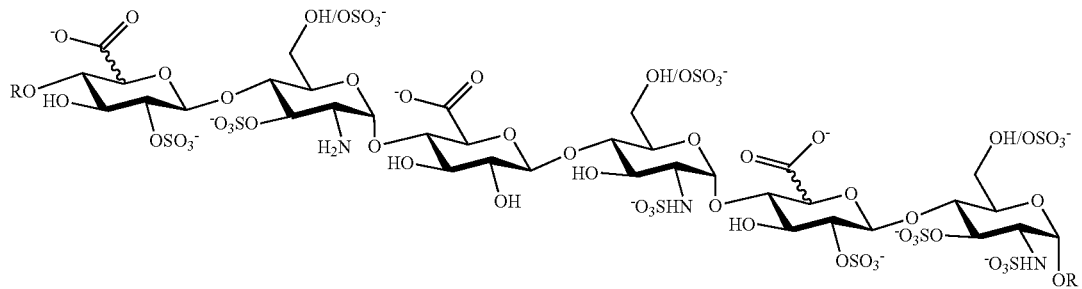

-OR: represents HS chain
-OH/OSO$_3^-$ means either a -OH or a -OSO$_3^-$ group
-NH$_2$/SO$_3^-$ means either a -NH$_2$ or a -NHSO$_3^-$ group In an advantageous embodiment, the level and/or activity of 3-O-sulfated heparan sulfate is further increased by 70% compared to the basal level and/or activity in the hippocampus.

In an advantageous embodiment, the level and/or activity of 3-O-sulfated heparan sulfate is further increased by 80% compared to the basal level and/or activity in the hippocampus.

In an advantageous embodiment, the level and/or activity of 3-O-sulfated heparan sulfate is further increased by 90% compared to the basal level and/or activity in the hippocampus The abnormal phosphorylation of Tau protein occurs after conformational changes induced by 3-O-sulfated HS, and the formation of the HS GlcA2S/IdoA2S-GlcNS3S6S (tetraS unit) and of the GlcA2S/IdoA2S-GlcNS3S (triS unit) in AD patients brains precede the phosphorylation event and thus these species are found in CSF from AD patients.

They should be absent, or present in lower levels than in AD, in other tauopathies in where abnormal phosphorylation is the result of mutations in the Tau protein gene. Detection of the TetraS and TriS disaccharides can thus be used for differential diagnosis and/or prognosis between tauopathies and AD, including those with mutation dependent Tau phosphorylation.

In an advantageous embodiment, the present invention relates to an in vitro method wherein said neurodegenerative disease is an Alzheimer's disease, wherein
said level of the transcription product of the gene set forth by SEQ ID NO: 1 is increased by at least 100% as determined by real time PCR, and/or
said level of the transcription product of the gene set forth by SEQ ID NO: 3 is increased by at least 100% as determined by real time PCR, and/or
said level of the translation product of the gene and set forth by SEQ ID NO: 2 is increased by at least 50% and/or said level of the translation product of the gene and set forth by SEQ ID NO: 4 is increased by at least 50% as determined by Western Blot, ELISA, mass spectrometry or immunohistochemistry methods and/or the level and/or activity of heparan sulfate is increased by at least 50% of said level compared to a reference value, as defined above, comprising further determining the level and/or activity of abnormal phosphorylation of Tau protein and/or total Tau protein, an increase of at least 10% compared to a respective reference value being indicative of Alzheimer's disease.

In Alzheimer's disease, the level of abnormal phosphorylation of Tau protein is increased as well as the level of total Tau protein.

Therefore, determining the level of abnormal phosphorylation of Tau protein or total Tau protein or both allows the diagnosis or prognostic or follow-up of Alzheimer's disease.

In an advantageous embodiment, said level and/or activity of abnormal phosphorylation of Tau protein is increased by at least 20% compared to said reference value.

In an advantageous embodiment, said level and/or activity of abnormal phosphorylation of Tau protein is increased by at least 30% compared to said reference value.

In an advantageous embodiment, said level and/or activity of abnormal phosphorylation of Tau protein is increased by at least 40% compared to said reference value.

In an advantageous embodiment, said level and/or activity of abnormal phosphorylation of Tau protein is increased by at least 50% compared to said reference value.

In an advantageous embodiment, said level and/or activity of abnormal phosphorylation of Tau protein is increased by at least 60% compared to said reference value.

In an advantageous embodiment, said level and/or activity of abnormal phosphorylation of Tau protein is increased by at least 70% compared to said reference value.

In an advantageous embodiment, said level and/or activity of abnormal phosphorylation of Tau protein is increased by at least 80% compared to said reference value.

In an advantageous embodiment, said level and/or activity of abnormal phosphorylation of Tau protein is increased by at least 90% compared to said reference value.

In an advantageous embodiment, said level and/or activity of total Tau protein is increased by at least 20% compared to said reference value.

In an advantageous embodiment, said level and/or activity of total Tau protein is increased by at least 30% compared to said reference value.

In an advantageous embodiment, said level and/or activity of total Tau protein is increased by at least 40% compared to said reference value.

In an advantageous embodiment, said level and/or activity of total Tau protein is increased by at least 50% compared to said reference value.

In an advantageous embodiment, said level and/or activity of total Tau protein is increased by at least 60% compared to said reference value.

In an advantageous embodiment, said level and/or activity of total Tau protein is increased by at least 70% compared to said reference value.

In an advantageous embodiment, said level and/or activity of total Tau protein is increased by at least 80% compared to said reference value.

In an advantageous embodiment, said level and/or activity of total Tau protein is increased by at least 90% compared to said reference value.

In an advantageous embodiment, said level and/or activity of total Tau protein is increased by at least 100% compared to said reference value.

In an advantageous embodiment, said level and/or activity of abnormal phosphorylation of Tau protein is increased by at least 10%, 20%, 30%, 40%, 50%, 60%, 70%, 80%, 90% or 100% compared to said reference value and said level and/or activity of total Tau protein is increased by at least 10%, 20%, 30%, 40%, 50%, 60%, 70%, 80%, 90% or 100% compared to said reference value.

The present invention shows results in where 3-OST-2 enzyme is present in CSF in AD patients and that the levels of the protein correlate with levels of hyperphosphorylated Tau in the same CSF samples. This demonstrates that the enzyme can, as Tau protein, be found in the extracellular space and thus pass to CSF and confirm that measure of its levels, or the measure of its activity, can be used as a diagnostic, and/or prognostic marker of AD disease.

In an advantageous embodiment, the present invention relates to an in vitro method wherein said neurodegenerative disease is an Alzheimer's disease, as defined above, wherein said biological fluid is the CSF and said activity and/or level of:
a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and
b) at least one transcription product of a gene selected from the group consisting of the nucleotidic sequences set forth by SEQ ID NO: 1 and SEQ ID NO: 3 and coding for an heparin-glucosamine 3-O-sulfotransferase, and
c) translation product of said genes, said products being set forth respectively by SEQ ID NO: 2 and 4, and
d) heparan sulfate, in particular 3-O-sulfated heparan sulfate, notably 3-O-sulfated heparan sulfate disaccharides, and
e) said activity and/or level of abnormal phosphorylation of the Tau protein and/or total Tau protein,
are increased in said subject compared to said respective reference value.

It must be noted that the increase of the level and/or activity of said gene and said transcription product of said gene and said translation product of said gene and HS could be increased before the increase of the abnormal phosphorylation of the Tau protein and/or total Tau protein.

In Alzheimer's disease, not only the abnormal phosphorylation of Tau protein is involved but also the 3-OST-2 and/or 3-OST-4 gene, at least one of the transcription products of said gene, at least one of the translation products of said genes, heparan sulfate and in particular heparan sulfate liable to bind to Tau protein notably 3-O-sulfated heparan sulfate.

This allows making a differential diagnostic and/or prognostic between Taupathies.

The detection of the abnormal phosphorylation of Tau protein and at least one of the other increased level and/or activity of the other constituents cited above allows thus the diagnostic and/or prognostic of an Alzheimer's disease.

Examples of the invention demonstrate that enzymes responsible of specific sulfation of HS (3-OST-2 and 4) are increased in AD brains and CSF and that the HS derived from these enzymes activities are involved in Tau abnormal phosphorylation in vitro and in vivo. Examples also show that the 3-O-sulfated groups in heparin are able to induce abnormal Tau phosphorylation in vitro.

Examples show particularly that the phosphorylation of Tau protein by GSK-3β is dependent of the presence of 3-O-sulfates groups in the polysaccharides or oligosaccharides used in the kinase reaction medium. Moreover, this invention shows that it is not the GSK-3β enzyme that binds to any of the used heparinoids but the Tau protein itself, suggesting the existence of conformational changes allowing exposition of the phosphorylated sites to the kinase activity. Thus, 3-O-sulfated HS interact with Tau protein regulating its phosphorylation in the presence of kinase.

It must be noted that said activity and/or level can also be a fragment or derivative or variant of said gene or said transcription or translation product.

The basal value in human CSF for pTau is about or less than 60 pg/ml and for total Tau is about or less than 450 pg/ml).

In an advantageous embodiment, said level and/or activity of abnormal phosphorylation of Tau protein is increased by at least 20% compared to said basal value.

In an advantageous embodiment, level and/or activity of abnormal phosphorylation of Tau protein is increased by at least 30% compared to said basal value.

In an advantageous embodiment, level and/or activity of abnormal phosphorylation of Tau protein is increased by at least 40% compared to said basal value.

In an advantageous embodiment, said level and/or activity of abnormal phosphorylation of Tau protein is increased by at least 50% compared to said basal value.

In an advantageous embodiment, said level and/or activity of abnormal phosphorylation of Tau protein is increased by at least 60% compared to said basal value.

In an advantageous embodiment, said level and/or activity of abnormal phosphorylation of Tau protein is increased by at least 70% compared said basal value.

In an advantageous embodiment, said level and/or activity of abnormal phosphorylation of Tau protein is increased by at least 80% compared to said basal value.

In an advantageous embodiment, said level and/or activity of abnormal phosphorylation of Tau protein is increased by at least 90% compared to said basal value.

In an advantageous embodiment, said level and/or activity of abnormal phosphorylation of Tau protein is increased by at least 100% compared to said basal value.

In an advantageous embodiment, said level and/or activity of total Tau protein is increased by at least 10% compared to said basal value.

In an advantageous embodiment, said level and/or activity of total Tau protein is increased by at least 20% compared to said basal value.

In an advantageous embodiment, said level and/or activity of abnormal phosphorylation of Tau protein is increased by at least 30% compared to said basal value.

In an advantageous embodiment, said level and/or activity of total Tau protein is increased by at least 40% compared to said basal value.

In an advantageous embodiment, said level and/or activity of total Tau protein is increased by at least 50% compared to said basal value.

In an advantageous embodiment said level and/or activity of total Tau protein is increased by at least 60% compared to said basal value.

In an advantageous embodiment, said level and/or activity of total Tau protein is increased by at least 70% compared said basal value.

In an advantageous embodiment, said level and/or activity of total Tau protein is increased by at least 80% compared to said basal value.

In an advantageous embodiment, said level and/or activity of total Tau protein is increased by at least 90% compared to said basal value.

In an advantageous embodiment, said level and/or activity of total Tau protein is increased by at least 100% compared to said basal value.

In an advantageous embodiment, said level and/or activity of abnormal phosphorylation of Tau protein is increased by at least 10%, 20%, 30%, 40%, 50%, 60%, 70%, 80%, 90% or 100% compared to said basal value and said level and/or activity of total Tau protein is increased by at least 10%, 20%, 30%, 40%, 50%, 60%, 70%, 80%, 90% or 100% compared to said basal value.

In an advantageous embodiment, the present invention relates to an in vitro method wherein said neurodegenerative disease is a Tauopathy, in particular an Alzheimer's disease, as defined above, wherein said biological fluid is the CSF and said activity and/or level of:
   a) heparan sulfate, in particular 3-O-sulfated heparan sulfate, notably 3-O-sulfated heparan sulfate disaccharides, and,
   b) abnormal phosphorylation of the Tau protein and/or total Tau protein, are increased in said subject compared to said respective reference value, in particular by at least 10% and said heparan sulfate are liable to bind to said phosphorylated Tau protein and/or total Tau in a ratio of at least 10%.

The Inventors have still further found that in Tauopathies, in particular Alzheimer's disease, the activity and/or level of heparan sulfate, in particular 3-O-sulfated heparan sulfate, notably 3-O-sulfated heparan sulfate disaccharides, and the one of abnormal phosphorylation of the Tau protein and/or total Tau protein are not only increased in CSF but also that the HS present in CSF has the highest capacity to bind to total Tau, being thus representative of said Tauopathies, in particular Alzheimer's disease.

In an advantageous embodiment,
   said level and/or activity of abnormal phosphorylation of Tau protein is increased by at least 10%, 20%, 30%, 40%, 50%, 60%, 70%, 80%, 90% or 100% compared to said basal value and said level and/or activity of total Tau protein is increased by at least 10%, 20%, 30%, 40%, 50%, 60%, 70%, 80%, 90% or 100% compared to said basal value, and
   said activity and/or level of heparan sulfate, in particular 3-O-sulfated heparan sulfate, notably 3-O-sulfated heparan sulfate disaccharides is increased by at least 10%, 20%, 30%, 40%, 50%, 60%, 70%, 80%, 90% or 100% compared to said basal value, and
   said the ratio of HS liable to bind to phosphorylated Tau protein and/or total Tau is comprised from 10% to 100%, in particular at least 20%, 30%, 40%, 50%, 60%, 70%, 80%, 90% or 100%.

In an advantageous embodiment, the present invention relates to an in vitro method wherein said neurodegenerative disease is an Alzheimer's disease, as defined above, wherein said biological fluid is plasma and wherein the heparane sulfate is a 3-O-sulfated heparan sulfate disaccharide of the glucosamine obtained after heparinase I, II and III (I-III) digestion of heparan sulfate.

Said 3-O-sulfated heparan sulfate disaccharides obtained by heparinases I, II and III digestion correspond, for example, to the following compounds, without being limited to them:

Tetrasulfated Disaccharide

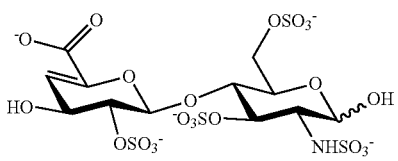

Trisulfated Disaccharides

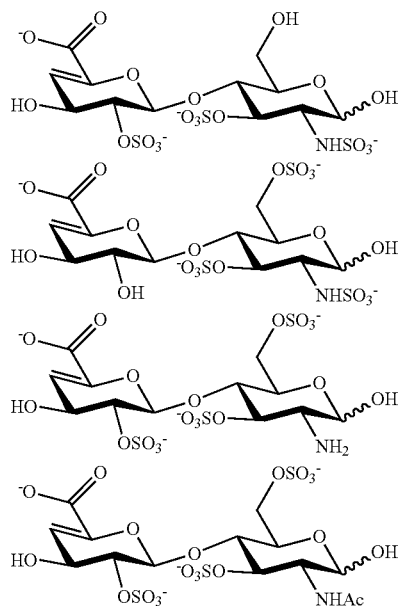

Disulfated Disaccharides

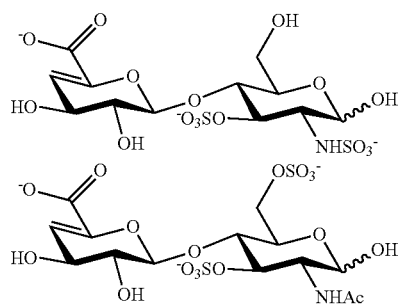

-continued

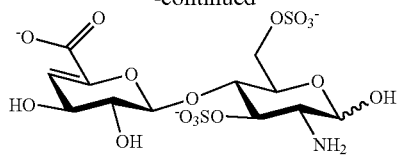

Another advantage of the invention is to provide an in vitro method of diagnosis or prognostic or follow-up of a neurodegenerative disease in a subject, or determining whether a subject is at increased risk of developing said neurodegenerative disease, that can be implemented very easily on a plasma sample that is easier to collect than a CSF sample.

In an advantageous embodiment, at least one of the disaccharides selected from the list above defined is present in the plasma of patient having Alzheimer's disease; in particular at least one of the two disaccharides selected below is present in said plasma.

Tetrasulfated Disaccharide

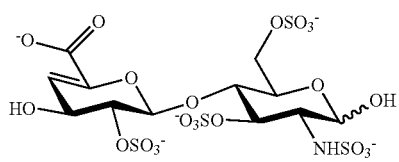

Trisulfated Disaccharide

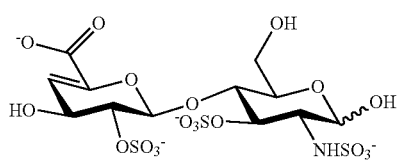

In an advantageous embodiment, the present invention relates to an in vitro method wherein said neurodegenerative disease is an Alzheimer's disease, as defined above, wherein said biological fluid is plasma, said derivative of translation product is a degradation product of heparan sulfate (glucosamine) 3-O-sulfotransferase 2 and/or 4, and and said heparane sulfate is a 3-O-sulfated heparan sulfate disaccharide obtained after heparinase I-III digestion of heparan sulfate, both level of said derivative of translation product and said level and/or activity of 3-O-sulfated heparan sulfate disaccharide being increased compared to a reference value or a basal value and indicative of an Alzheimer's disease.

In another aspect, the present invention relates to a kit of diagnosing or prognosticating or following-up of a neurodegenerative disease, advantageously a Tauopathy, in particular Alzheimer's disease, in a subject, or determining the propensity or predisposition of a subject to develop such a disease, provided that said neurodegenerative disease is different from a prion disease, consisting of means for recognizing and detecting in a sample of a biological fluid obtained from said subject, a level and/or an activity of:

at least one transcription product of a gene selected from the group consisting of the nucleotidic sequences set forth by SEQ ID NO: 1 and SEQ ID NO: 3 and coding for an heparin-glucosamine 3-O-sulfotransferase, and/or at least one translation product of said genes, said products being set forth respectively by SEQ ID NO: 2 and 4, and comparing said level and/or activity obtained in said sample with the one obtained with a control representing a known disease or health status.

Means for recognizing said at least one transcription product of a gene or said at least one translation product of said genes can be for example antibodies allowing carrying out an Elisa assay.

The present invention features an antibody which is especially immunoreactive with an immunogen, where said immunogen is a translation product of a gene coding for HS3ST2 and/or HS3ST4, or the glycanic products of the enzymatic activity of such proteins, or a fragment, or derivative, or variant thereof. The immunogen may comprise immunogenic or antigenic epitopes or portions of a translation product of said gene, wherein said immunogenic or antigenic portion of a translation product is a polypeptide, and wherein said polypeptide elicits an antibody response in an animal, and wherein said polypeptide is immunospecifically bound by said antibody. Methods for generating antibodies are well known in the art (Harlow et al., Antibodies, *A Laboratory Manual*, Vold Spring Harbor Laboratory Press, Cold Spring Harbor, new York, 1988). The term "antibody", as employed in the present invention, encompasses all forms of antibodies known in the art, such as polyclonal, monoclonal, chimeric, recombinatorial, anti-idiotypic, humanized, or single chain antibodies, as well as fragments thereof (Dubel and Breitling, *Recombinant Antibodies*, Wiley-Liss, New York, N.Y., 1999). Antibodies prepared by phage display technology are also comprised. Antibodies of the present invention are useful, for instance, in a variety of diagnostic and therapeutic methods based on state-in-the-art techniques (Harlow and Lane, Using Antibodies: A laboratory Manual, Cold Spring Harbor Laboratory Press, Cold Spring harbor, New York, 1999 and Edwards R, Immunodiagnostics: A practical Approach, Oxford University Press, Oxford, England, A999) such as enzyme-immuno assays (e.g. enzyme-linked immunosorbent assay, ELISA), radioimmuno assays, chemoluminescence-immuno assays, Western-blot, immunoprecipitation and antibody microarrays. These methods involve the detection of translation products of a gene coding for HS3ST2 and/or HS3ST4, or the glycanic products of the enzymatic activity of such proteins or fragment, or derivatives, or variants thereof.

An increased level of at least one transcription product of a gene selected from the group consisting of the nucleotidic sequences set forth by SEQ ID NO: 1 and SEQ ID NO: 3 and coding for an heparin-glucosamine 3-O-sulfotransferase, and/or at least one translation product of said genes, said products being set forth respectively by SEQ ID NO: 2 and 4, compared to a control representing an health status being indicative of a neurodegenerative disease, in particular an Alzheimer's disease.

In an advantageous embodiment, the present invention relates to a kit defined above, consisting further of means for recognizing and detecting heparan and/or a heparan sulfate disaccharide sulfated en position 3 of the glucosamine obtained after heparinases I-III digestion of heparan sulfate.

An increased level of at least one transcription product of a gene selected from the group consisting of the nucleotidic sequences set forth by SEQ ID NO: 1 and SEQ ID NO: 3 and coding for an heparin-glucosamine 3-O-sulfotransferase, and/or at least one translation product of said genes, said products being set forth respectively by SEQ ID NO: 2 and 4, and of heparan and/or a heparan sulfate disaccharide sulfated en position 3 of the glucosamine obtained after heparinases I-III digestion of heparan sulfate, compared to a control representing an health status being indicative of a neurodegenerative disease, in particular an Alzheimer's disease.

In an advantageous embodiment, the present invention relates to a kit consisting of means for recognizing and detecting in a sample of a biological fluid obtained from said subject, a level and/or an activity of:

at least one transcription product of a gene selected from the group consisting of the nucleotidic sequences set forth by SEQ ID NO: 1 and SEQ ID NO: 3 and coding for an heparin-glucosamine 3-O-sulfotransferase, and/or at least one translation product of said genes, said products being set forth respectively by SEQ ID NO: 2 and 4, and optionally means for recognizing and detecting heparan sulfate and/or a heparan sulfate disaccharide sulfated en position 3 of the glucosamine obtained after heparinases I-III digestion of heparan sulfate, consisting further of means for determining the level of phosphorylation of Tau protein in a sample obtained from said subject, and comparing said level obtained with said sample with the one obtained with a control representing a known disease or health status, and comparing the abnormal phosphorylation Tau level and/or total Tau levels, and the levels of the SEQ ID NO: 2 and SEQ ID NO: 4 translation products with a control representing a known disease or health status.

An increased level of at least one transcription product of a gene selected from the group consisting of the nucleotidic sequences set forth by SEQ ID NO: 1 and SEQ ID NO: 3 and coding for an heparin-glucosamine 3-O-sulfotransferase, and/or at least one translation product of said genes, said products being set forth respectively by SEQ ID NO: 2 and 4, and optionally of heparan and/or a heparan sulfate disaccharide sulfated en position 3 of the glucosamine obtained after heparinases I-III digestion of heparan sulfate, and of the abnormal phosphorylation Tau level, compared to a control representing an health status being indicative of a neurodegenerative disease, in particular an Alzheimer's disease.

A method for an in vitro screening for a modulator of neurodegenerative diseases, in particular Alzheimer's disease, provided that said neurodegenerative disease is different from a prion disease, comprising:

a) contacting a sample of a biological fluid previously collected from a mammal or a fish, in particular a mammal being subject to a neurodegenerative disease, with a compound to test, b) determining the activity and/or a level of:

i. at least one gene selected from the group consisting of the nucleotidic sequences set forth by SEQ ID NO: 1 and SEQ ID NO: 3 and coding for an heparin-glucosamine 3-O-sulfotransferase, and/or ii. at least one transcription product of a gene selected from the group consisting of the nucleotidic sequences set forth by SEQ ID NO: 1 and SEQ ID
NO: 3 and coding for an heparin-glucosamine 3-O-
sulfotransferase, and/or iii. at least one translation product of said genes, said products being set forth respectively by SEQ ID NO: 2 and 4, and/or iv. a fragment or derivative or variant of said gene or transcription or translation product, and/or v. the level of heparan sulfate, in particular the level of 3-O-sulfated heparan sulfate, notably the level of 3-O-sulfated heparan sulfate disaccharide and/or vi. the level of abnormal phosphorylation of the Tau protein and/or total Tau protein, c) determining said activity and/or a level in a control sample of a biological fluid previously collected from a mammal with a neurodegenerative disease not contacted with said compound, d) comparing the difference of said activity and/or a level in the contacted sample of a biological fluid with the one in the non contacted sample of a biological fluid, wherein an alteration in said activity and/or level of the contacted cell indicates that the test compound is a modulator of said disease.

Thus a compound liable to decrease only the level of abnormal phosphorylation of the Tau protein and/or total Tau protein is a modulator of a Tauopathy.

A compound liable to decrease:

the level of abnormal phosphorylation of the Tau protein and/or total Tau protein is a modulator of a Tauopathy, and, 3-OST-2 and/or 4 gene and/or its transcription product and/or its translation product and/or heparan sulfate, in particular 3-O-sulfated heparan sulfate, notably 3-O-sulfated heparan sulfate disaccharide, is a modulator of Alzheimer's disease.

In an advantageous embodiment, said heparan sulfate is a 3-O-sulfated heparan sulfate disaccharide of the glucosamine obtained after heparinases I-III digestion of heparan sulfate.

Said biological fluid can be the extracellular medium of any cell culture, in particular neurons in primary culture but also the blood, the plasma, the serum, urine, saliva, or the cerebrospinal fluid (CSF).

In an advantageous embodiment, A method for an in vitro screening for a modulator of neurodegenerative diseases, in particular Alzheimer's disease, provided that said neurodegenerative disease is different from a prion disease, as defined above, wherein said mammal is a human or a mouse such as a SAMP8 mouse and/or the 3×Tg-AD mice model of AD.

In an advantageous embodiment, a method for an in vitro screening for a modulator of neurodegenerative diseases, in particular Alzheimer's disease, provided that said neurodegenerative disease is different from a prion disease, as defined above, wherein said fish is Zebra fish.

In another aspect, the present invention relates to a method of diagnosis or prognostic or follow-up of a neurodegenerative disease in a subject, or determining whether a subject is at increased risk of developing said neurodegenerative disease, comprising determining a level and/or an activity of:

a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or b) at least one transcription product of a gene selected from the group consisting of the nucleotidic sequences set forth by SEQ ID NO: 1 and SEQ ID NO: 3 and coding for isoformes of heparan sulfate (glucosamine) 3-O-sulfotransferase 2 and 4 respectively, and/or c) at least one translation product of said genes, said products being set forth respectively by SEQ ID NO: 2 and 4, and/or d) fragments or derivatives or variant of said transcription or translation product, and/or e) heparan sulfate, in particular 3-O-sulfated heparan sulfate, notably 3-O-sulfated heparan sulfate disaccharides, and/or f) abnormal phosphorylated Tau protein and/or total Tau protein, in a sample obtained from said subject and comparing said level and/or said activity to a respective reference value representing a known disease or health status, an increased level and/or activity of at least one of said transcription product or said translation product heparan sulfate, in particular 3-O-sulfated heparan sulfate, notably 3-O-sulfated heparan sulfate disaccharides, or abnormal phosphorylated Tau protein in the subject sample, being indicative of a neurodegenerative disease or a risk of developing said neurodegenerative disease, advantageously a Tauopathy, in particular an Alzheimer's disease, provided that said neurodegenerative disease is different from a prion disease.

In this embodiment, the levels and/or activities are determined in vivo.

The subject can be a mammal such as a human or a mouse, or a fish.

The Inventors have thus found that the level of expression of the 3-OST-2 and/or 3-OST-4 gene was highly increased in neurodegenerative diseases, in particular in Alzheimer's disease leading thus to higher 3-O-sulfation of HS chains or leading to heparin-like HS structures.

Thus the level and/or the activity of one or both gene(s) as set forth by SEQ ID NO: 1 and 3 are increased but also one of or both transcription product(s) of said genes are increased as well as one or both translation product(s) of said genes, that is proteins as set forth by SEQ ID NO: 2 and 4.

3-OST-2 and -4 being responsive of the 3-O-sulfation of heparan sulfate, the level of said 3-O-sulfated heparan sulfate is then also highly increased, inducing conformational changes in Tau protein leading to the abnormal phosphorylation of Tau protein.

Thus the detection in a subject of an increased level and/or activity of at least one of these constituents will lead to the diagnostic or prognostic of a neurodegenerative disease, in particular an Alzheimer's disease or a Tauopathy.

In an advantageous embodiment, the present invention relates to a method of diagnosis or prognostic or follow-up of a neurodegenerative disease in a subject, or determining whether a subject is at increased risk of developing said neurodegenerative disease as defined above, wherein said neurodegenerative disease is a Tauopathy.

In an advantageous embodiment, the present invention relates to a method of diagnosis or prognostic or follow-up of a neurodegenerative disease in a subject, or determining whether a subject is at increased risk of developing said neurodegenerative disease in a subject as defined above, wherein the level of phosphorylation of Tau protein and/or total Tau protein is increased by at least 10% compared to a reference value.

The reference value can take a variety of forms. It can be single cut-off value, such as for instance a median or mean or the 75th, 90th, 95th or 99th percentile of a population. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quartiles, the lowest quartile being individuals with the lowest risk and the highest quartile being individuals with the highest risk.

The predetermined value can vary among particular populations selected, depending on their habits, ethnicity, genetics etc.

In an advantageous embodiment, said level and/or activity of abnormal phosphorylation of Tau protein is increased by at least 20% compared to said reference value.

In an advantageous embodiment, said level and/or activity of abnormal phosphorylation of Tau protein is increased by at least 30% compared to said reference value.

In an advantageous embodiment, said level and/or activity of abnormal phosphorylation of Tau protein is increased by at least 40% compared to said reference value.

In an advantageous embodiment, said level and/or activity of abnormal phosphorylation of Tau protein is increased by at least 50% compared to said reference value.

In an advantageous embodiment, said level and/or activity of abnormal phosphorylation of Tau protein is increased by at least 60% compared to said reference value.

In an advantageous embodiment, said level and/or activity of abnormal phosphorylation of Tau protein is increased by at least 70% compared to said reference value.

In an advantageous embodiment, said level and/or activity of abnormal phosphorylation of Tau protein is increased by at least 80% compared to said reference value.

In an advantageous embodiment, said level and/or activity of abnormal phosphorylation of Tau protein is increased by at least 90% compared to said reference value.

In an advantageous embodiment, said level and/or activity of total Tau protein is increased by at least 20% compared to said reference value.

In an advantageous embodiment, said level and/or activity of total Tau protein is increased by at least 30% compared to said reference value.

In an advantageous embodiment, said level and/or activity of total Tau protein is increased by at least 40% compared to said reference value.

In an advantageous embodiment, said level and/or activity of total Tau protein is increased by at least 50% compared to said reference value.

In an advantageous embodiment, said level and/or activity of total Tau protein is increased by at least 60% compared to said reference value.

In an advantageous embodiment, said level and/or activity of total Tau protein is increased by at least 70% compared to said reference value.

In an advantageous embodiment, said level and/or activity of total Tau protein is increased by at least 80% compared to said reference value.

In an advantageous embodiment, said level and/or activity of total Tau protein is increased by at least 90% compared to said reference value.

In an advantageous embodiment, said level and/or activity of total Tau protein is increased by at least 100% compared to said reference value.

In an advantageous embodiment, said level and/or activity of abnormal phosphorylation of Tau protein is increased by at least 10%, 20%, 30%, 40%, 50%, 60%, 70%, 80%, 90% or 100% compared to said reference value and said level and/or activity of total Tau protein is increased by at least 10%, 20%, 30%, 40%, 50%, 60%, 70%, 80%, 90% or 100% compared to said reference value.

In another aspect the present invention relates to a method of diagnosis or prognostic or follow-up of a neurodegenerative disease in a subject, or determining whether a subject is at increased risk of developing said neurodegenerative disease, comprising determining a level and/or an activity of:
  a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  b) at least one transcription product of a gene selected from the group consisting of the nucleotidic sequences set forth by SEQ ID NO: 1 and SEQ ID NO: 3 and coding for isoformes of heparan sulfate (glucosamine) 3-O-sulfotransferase 2 and 4 respectively, and/or
  c) at least one translation product of said genes, said products being set forth respectively by SEQ ID NO: 2 and 4, and/or
  d) fragments or derivatives or variant of said transcription or translation product, and/or
  e) heparan sulfate, in particular 3-O-sulfated heparan sulfate, notably 3-O-sulfated heparan sulfate disaccharides, and/or
  f) abnormal phosphorylated Tau protein and/or total Tau protein,
in a sample obtained from said subject and comparing said level and/or said activity to a respective reference value representing a known disease or health status,
an increased level and/or activity of at least one of said transcription product or said translation product heparan sulfate, in particular 3-O-sulfated heparan sulfate, notably 3-O-sulfated heparan sulfate disaccharides, or abnormal phosphorylated Tau protein in the subject sample, being indicative of a neurodegenerative disease or a risk of developing said neurodegenerative disease, advantageously a Tauopathy, in particular an Alzheimer's disease, provided that said neurodegenerative disease is different from a prion disease, and provided that when said activity and/or the level determined is the one of:
  heparan sulfate, or
  of abnormal phosphorylation of the Tau protein and/or total Tau protein,
therefore, the activities and/or levels heparan sulfate and abnormal phosphorylation of the Tau protein and/or total Tau protein are both determined, or
the activity and/or the level of at least one other element chosen among said gene, said transcription product of said genes, said translation product of said genes, or said fragment or derivative or variant of said gene or said transcription or translation product is also determined.

In an advantageous embodiment, the present invention relates to a method of diagnosis or prognostic or follow-up of a neurodegenerative disease in a subject, or determining whether a subject is at increased risk of developing said neurodegenerative disease in a subject as defined above, wherein said biological fluid is the CSF and said activity and/or level of:
  a) said gene selected from the group consisting of the nucleotidic sequences set forth by SEQ ID NO: 1 and SEQ ID NO: 3 and coding for an heparin-glucosamine 3-O-sulfotransferase 2 and 4 respectively, and
  b) said transcription product of a gene selected from the group consisting of the nucleotidic sequences set forth by SEQ ID NO: 1 and SEQ ID NO: 3 and coding for an heparin-glucosamine 3-O-sulfotransferase, and c) said translation product of said genes, said products being set forth respectively by SEQ ID NO: 2 and 4, and d) a fragment or derivative or variant of said gene or said transcription or translation product, and e) heparan sulfate, in particular 3-O-sulfated heparan sulfate, notably 3-O-sulfated heparan sulfate disaccharides, in a subject are substantially the same as the respective reference value and, said activity and/or level of abnormal phosphorylation of the Tau protein and/or total Tau protein is increased in said subject compared to said reference value, in particular by at least 100%.

In Tauopathy other than Alzheimer's disease, only the abnormal phosphorylation of Tau protein is involved and thus, this allows making a differential diagnostic and/or prognostic between Tauopathies.

The detection of only the abnormal phosphorylation of Tau protein without detecting any other increased level and/or activity of the other constituents cited above allows thus the diagnostic and/or prognostic of a Tauopathy other than Alzheimer's disease.

The expression "substantially the same" means that the measured level can vary with respect to the reference value because of the individual variation among particular populations selected, depending on their habits, ethnicity, genetics etc. therefore, Therefore, the measured level can be plus/minus 10%, plus/minus 5% or plus/minus 2.5% of the reference value.

The basal value in human CSF for pTau is about or less than 60 pg/ml and for total Tau is about or less than 450 pg/ml).

In an advantageous embodiment, said level and/or activity of abnormal phosphorylation of Tau protein is increased by at least 20% compared to said basal value.

In an advantageous embodiment, level and/or activity of abnormal phosphorylation of Tau protein is increased by at least 30% compared to said basal value.

In an advantageous embodiment, level and/or activity of abnormal phosphorylation of Tau protein is increased by at least 40% compared to said basal value.

In an advantageous embodiment, said level and/or activity of abnormal phosphorylation of Tau protein is increased by at least 50% compared to said basal value.

In an advantageous embodiment, said level and/or activity of abnormal phosphorylation of Tau protein is increased by at least 60% compared to said basal value.

In an advantageous embodiment, said level and/or activity of abnormal phosphorylation of Tau protein is increased by at least 70% compared said basal value.

In an advantageous embodiment, said level and/or activity of abnormal phosphorylation of Tau protein is increased by at least 80% compared to said basal value.

In an advantageous embodiment, said level and/or activity of abnormal phosphorylation of Tau protein is increased by at least 90% compared to said basal value.

In an advantageous embodiment, said level and/or activity of abnormal phosphorylation of Tau protein is increased by at least 100% compared to said basal value.

In an advantageous embodiment, said level and/or activity of total Tau protein is increased by at least 10% compared to said basal value.

In an advantageous embodiment, said level and/or activity of total Tau protein is increased by at least 20% compared to said basal value.

In an advantageous embodiment, said level and/or activity of abnormal phosphorylation of Tau protein is increased by at least 30% compared to said basal value.

In an advantageous embodiment, said level and/or activity of total Tau protein is increased by at least 40% compared to said basal value.

In an advantageous embodiment, said level and/or activity of total Tau protein is increased by at least 50% compared to said basal value.

In an advantageous embodiment said level and/or activity of total Tau protein is increased by at least 60% compared to said basal value.

In an advantageous embodiment, said level and/or activity of total Tau protein is increased by at least 70% compared said basal value.

In an advantageous embodiment, said level and/or activity of total Tau protein is increased by at least 80% compared to said basal value.

In an advantageous embodiment, said level and/or activity of total Tau protein is increased by at least 90% compared to said basal value.

In an advantageous embodiment, said level and/or activity of total Tau protein is increased by at least 100% compared to said basal value.

In an advantageous embodiment, said level and/or activity of abnormal phosphorylation of Tau protein is increased by at least 10%, 20%, 30%, 40%, 50%, 60%, 70%, 80%, 90% or 100% compared to said basal value and said level and/or activity of total Tau protein is increased by at least 10%, 20%, 30%, 40%, 50%, 60%, 70%, 80%, 90% or 100% compared to said basal value.

In an advantageous embodiment, the present invention relates to a method of diagnosis or prognostic or follow-up of a neurodegenerative disease in a subject, or determining whether a subject is at increased risk of developing said neurodegenerative disease in a subject as defined above, wherein said neurodegenerative disease is an Alzheimer's disease.

In an advantageous embodiment, the present invention relates to a method of diagnosis or prognostic or follow-up of a neurodegenerative disease in a subject, or determining whether a subject is at increased risk of developing said neurodegenerative disease in a subject as defined above, wherein said level of the transcription product of the gene set forth by SEQ ID NO: 1 is increased by at least 100% as determined by real time PCR.

In this embodiment, only the 3-OST-2 gene is implicated in the disease, the level of the 3-OST-4 gene is substantially unchanged.

In an advantageous embodiment, said level of the transcription product of the gene set forth by SEQ ID NO: 1 is increased by at least 200% as determined by real time PCR.

In an advantageous embodiment, said level of the transcription product of the gene set forth by SEQ ID NO: 1 is increased by at least 300% as determined by real time PCR.

In an advantageous embodiment, said level of the transcription product of the gene set forth by SEQ ID NO: 1 is increased by at least 400% as determined by real time PCR.

In an advantageous embodiment, the present invention relates to a method of diagnosis or prognostic or follow-up of a neurodegenerative disease in a subject, or determining whether a subject is at increased risk of developing said neurodegenerative disease in a subject as defined above, wherein said level of the transcription product of the gene set forth by SEQ ID NO: 3 is increased by at least 100% as determined by real time PCR.

In this embodiment, only the 3-OST-4 gene is implicated in the disease, the level of the 3-OST-2 gene is substantially unchanged.

In an advantageous embodiment, said level of the transcription product of the gene set forth by SEQ ID NO: 3 is increased by at least 200% as determined by real time PCR.

In an advantageous embodiment, said level of the transcription product of the gene set forth by SEQ ID NO: 3 is increased by at least 300% as determined by real time PCR.

In an advantageous embodiment, said level of the transcription product of the gene set forth by SEQ ID NO: 3 is increased by at least 400% as determined by real time PCR.

In an advantageous embodiment, the present invention relates to a method of diagnosis or prognostic or follow-up of a neurodegenerative disease in a subject, or determining whether a subject is at increased risk of developing said neurodegenerative disease in a subject as defined above, wherein said level of the transcription product of the gene set forth by SEQ ID NO: 1 is increased by at least 100% and said level of the transcription product of the gene set forth by SEQ ID NO: 3 is increased by at least 100% as determined by real time PCR.

In this embodiment, both 3-OST-2 and 3-OST-4 genes are implicated in the disease.

In an advantageous embodiment, said level of the transcription product of the gene set forth by SEQ ID NO: 1 is increased by at least 100% as determined by real time PCR and said level of the transcription product of the gene set forth by SEQ ID NO: 3 is increased by at least 200% as determined by real time PCR.

In an advantageous embodiment, said level of the transcription product of the gene set forth by SEQ ID NO: 1 is increased by at least 100% as determined by real time PCR and said level of the transcription product of the gene set forth by SEQ ID NO: 3 is increased by at least 300% as determined by real time PCR.

In an advantageous embodiment, said level of the transcription product of the gene set forth by SEQ ID NO: 1 is increased by at least 100% as determined by real time PCR and said level of the transcription product of the gene set forth by SEQ ID NO: 3 is increased by at least 400% as determined by real time PCR.

In an advantageous embodiment, said level of the transcription product of the gene set forth by SEQ ID NO: 1 is increased by at least 200% as determined by real time PCR and said level of the transcription product of the gene set forth by SEQ ID NO: 3 is increased by at least 100% as determined by real time PCR.

In an advantageous embodiment, said level of the transcription product of the gene set forth by SEQ ID NO: 1 is increased by at least 200% as determined by real time PCR and said level of the transcription product of the gene set forth by SEQ ID NO: 3 is increased by at least 200% as determined by real time PCR.

In an advantageous embodiment, said level of the transcription product of the gene set forth by SEQ ID NO: 1 is increased by at least 200% as determined by real time PCR and said level of the transcription product of the gene set forth by SEQ ID NO: 3 is increased by at least 300% as determined by real time PCR.

In an advantageous embodiment, said level of the transcription product of the gene set forth by SEQ ID NO: 1 is increased by at least 200% as determined by real time PCR and said level of the transcription product of the gene set forth by SEQ ID NO: 3 is increased by at least 400% as determined by real time PCR.

In an advantageous embodiment, said level of the transcription product of the gene set forth by SEQ ID NO: 1 is increased by at least 300% as determined by real time PCR and said level of the transcription product of the gene set forth by SEQ ID NO: 3 is increased by at least 100% as determined by real time PCR.

In an advantageous embodiment, said level of the transcription product of the gene set forth by SEQ ID NO: 1 is increased by at least 300% as determined by real time PCR and said level of the transcription product of the gene set forth by SEQ ID NO: 3 is increased by at least 200% as determined by real time PCR.

In an advantageous embodiment, said level of the transcription product of the gene set forth by SEQ ID NO: 1 is increased by at least 300% as determined by real time PCR and said level of the transcription product of the gene set forth by SEQ ID NO: 3 is increased by at least 300% as determined by real time PCR.

In an advantageous embodiment, said level of the transcription product of the gene set forth by SEQ ID NO: 1 is increased by at least 300% as determined by real time PCR and said level of the transcription product of the gene set forth by SEQ ID NO: 3 is increased by at least 400% as determined by real time PCR.

In an advantageous embodiment, said level of the transcription product of the gene set forth by SEQ ID NO: 1 is increased by at least 400% as determined by real time PCR and said level of the transcription product of the gene set forth by SEQ ID NO: 3 is increased by at least 100% as determined by real time PCR.

In an advantageous embodiment, said level of the transcription product of the gene set forth by SEQ ID NO: 1 is increased by at least 400% as determined by real time PCR and said level of the transcription product of the gene set forth by SEQ ID NO: 3 is increased by at least 200% as determined by real time PCR.

In an advantageous embodiment, said level of the transcription product of the gene set forth by SEQ ID NO: 1 is increased by at least 400% as determined by real time PCR and said level of the transcription product of the gene set forth by SEQ ID NO: 3 is increased by at least 300% as determined by real time PCR.

In an advantageous embodiment, said level of the transcription product of the gene set forth by SEQ ID NO: 1 is increased by at least 400% as determined by real time PCR and said level of the transcription product of the gene set forth by SEQ ID NO: 3 is increased by at least 400% as determined by real time PCR.

In an advantageous embodiment, the present invention relates to a method of diagnosis or prognostic or follow-up of a neurodegenerative disease in a subject, or determining whether a subject is at increased risk of developing said neurodegenerative disease in a subject as defined above, wherein said level of the translation product of the gene and set forth by SEQ ID NO: 2 is increased by at least 50% as determined by Western Blot, ELISA, mass spectrometry or immunohistochemistry methods.

Other methods well known from a man skilled in the art can also be used for said determination.

In an advantageous embodiment, said level of the translation product of the gene set forth by SEQ ID NO: 2 is increased by at least 60% as determined by Western Blot, ELISA, mass spectrometry or immunohistochemistry methods.

In an advantageous embodiment, said level of the translation product of the gene set forth by SEQ ID NO: 2 is increased by at least 70% as determined by Western Blot, ELISA, mass spectrometry or immunohistochemistry methods.

In an advantageous embodiment, said level of the translation product of the gene set forth by SEQ ID NO: 2 is increased by at least 80% as determined by Western Blot, ELISA, mass spectrometry or immunohistochemistry methods.

In an advantageous embodiment, said level of the translation product of the gene set forth by SEQ ID NO: 2 is increased by at least 90% as determined by Western Blot, ELISA, mass spectrometry or immunohistochemistry methods.

In an advantageous embodiment, said level of the translation product of the gene set forth by SEQ ID NO: 2 is increased by at least 100% as determined by Western Blot, ELISA, mass spectrometry or immunohistochemistry methods.

The basal value in human CSF for 3-OST-2 is 60 pg/ml.

In an advantageous embodiment, said level of the translation product of the gene set forth by SEQ ID NO: 2 compared to said basal level is increased by at least 60% as determined by Western Blot, ELISA, mass spectrometry or immunohistochemistry methods in CSF.

In an advantageous embodiment, said level of the translation product of the gene set forth by SEQ ID NO: 2 compared to said basal level is increased by at least 70% as determined by Western Blot, ELISA, mass spectrometry or immunohistochemistry methods in CSF.

In an advantageous embodiment, said level of the translation product of the gene set forth by SEQ ID NO: 2 compared to said basal level is increased by at least 80% as determined by Western Blot, ELISA, mass spectrometry or immunohistochemistry methods in CSF.

In an advantageous embodiment, said level of the translation product of the gene set forth by SEQ ID NO: 2 compared to said basal level is increased by at least 90% as determined by Western Blot, ELISA, mass spectrometry or immunohistochemistry methods in CSF.

In an advantageous embodiment, said level of the translation product of the gene set forth by SEQ ID NO: 2 compared to said basal level is increased by at least 100% as determined by Western Blot, ELISA, mass spectrometry or immunohistochemistry methods in CSF.

In an advantageous embodiment, the present invention relates to a method of diagnosis or prognostic or follow-up of a neurodegenerative disease in a subject, or determining whether a subject is at increased risk of developing said neurodegenerative disease in a subject as defined above, wherein said level of the translation product of the gene and set forth by SEQ ID NO: 4 is increased by at least 50% as determined by Western Blot, ELISA, mass spectrometry or immunohistochemistry methods.

Other methods well known from a man skilled in the art can also be used for said determination.

In an advantageous embodiment, said level of the translation product of the gene set forth by SEQ ID NO: 4 is increased by at least 60% as determined by Western Blot, ELISA, mass spectrometry or immunohistochemistry methods.

In an advantageous embodiment, said level of the translation product of the gene set forth by SEQ ID NO: 4 is increased by at least 70% as determined by Western Blot, ELISA, mass spectrometry or immunohistochemistry methods.

In an advantageous embodiment, said level of the translation product of the gene set forth by SEQ ID NO: 4 is increased by at least 80% as determined by Western Blot, ELISA, mass spectrometry or immunohistochemistry methods.

In an advantageous embodiment, said level of the translation product of the gene set forth by SEQ ID NO: 4 is increased by at least 90% as determined by Western Blot, ELISA, mass spectrometry or immunohistochemistry methods.

In an advantageous embodiment, said level of the translation product of the gene set forth by SEQ ID NO: 4 is increased by at least 100% as determined by Western Blot, ELISA, mass spectrometry or immunohistochemistry methods.

The basal value in human CSF for 3-OST-4 is 60 pg/ml.

In an advantageous embodiment, said level of the translation product of the gene set forth by SEQ ID NO: 4 compared to said basal level is increased by at least 60% as determined by Western Blot, ELISA, mass spectrometry or immunohistochemistry methods in CSF.

In an advantageous embodiment, said level of the translation product of the gene set forth by SEQ ID NO: 4 compared to said basal level is increased by at least 70% as determined by Western Blot, ELISA, mass spectrometry or immunohistochemistry methods in CSF.

In an advantageous embodiment, said level of the translation product of the gene set forth by SEQ ID NO: 4 compared to said basal level is increased by at least 80% as determined by Western Blot, ELISA, mass spectrometry or immunohistochemistry methods in CSF.

In an advantageous embodiment, said level of the translation product of the gene set forth by SEQ ID NO: 4 compared to said basal level is increased by at least 90% as determined by Western Blot, ELISA, mass spectrometry or immunohistochemistry methods in CSF.

In an advantageous embodiment, said level of the translation product of the gene set forth by SEQ ID NO: 4 compared to said basal level is increased by at least 100% as determined by Western Blot, ELISA, mass spectrometry or immunohistochemistry methods in CSF.

In an advantageous embodiment, the present invention relates to a method of diagnosis or prognostic or follow-up of a neurodegenerative disease in a subject, or determining whether a subject is at increased risk of developing said neurodegenerative disease in a subject as defined above, wherein said level of the translation product of the gene and set forth by SEQ ID NO: 2 is increased by at least 50% as determined by ELISA or Western Blot and wherein said level of the translation product of the gene and set forth by SEQ ID NO: 4 is increased by at least 50% as determined by Western Blot, ELISA, mass spectrometry or immunohistochemistry methods.

Other methods well known from a man skilled in the art can also be used for said determination.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 50% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 60% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 70% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 80% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 90% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 50% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 60% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 70% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 80% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 90% as determined by Western Blot, ELISA, mass spectrometry or immunohistochemistry methods.

In an advantageous embodiment, said level of the translation product of the gene set forth by SEQ ID NO: 2 compared to a reference value is increased by at least 100% and said level of the translation product of the gene set forth by SEQ ID NO: 4 compared to a reference value is increased by at least 100% as determined by Western Blot, ELISA, mass spectrometry or immunohistochemistry methods.

In an advantageous embodiment, said reference value for 3-OST-2 is the basal value for 3-OST-2 in human CSF and is 60 pg/ml and said reference value for 3-OST-4 is the basal value for 3-OST-2 in human CSF and is 60 pg/ml.

In an advantageous embodiment, the present invention relates to one of the method of diagnosis or prognostic or follow-up of a neurodegenerative disease in a subject, or determining whether a subject is at increased risk of developing said neurodegenerative disease in a subject as defined above, comprising further determining the level and/or activity of heparan sulfate, in particular of 3-O-sulfated heparan sulfate, an increase of at least 50% of said level and/or activity compared to a reference value being indicative of Alzheimer's disease.

In an advantageous embodiment, said level and/or activity of heparan sulfate is further increased by 60% compared to said reference value.

In an advantageous embodiment, said level and/or activity of heparan sulfate is further increased by 70% compared to said reference value.

In an advantageous embodiment, said level and/or activity of heparan sulfate is further increased by 80% compared to said reference value.

In an advantageous embodiment, said level and/or activity of heparan sulfate is further increased by 90% compared to said reference value.

In an advantageous embodiment, said level and/or activity of heparan sulfate is further increased by 100% compared to said reference value.

The basal level of heparan sulfate in a control human hippocampus is about 0.5 µg/mg of wet tissue as determined by the dimethylmethylene blue (DMMB) assay (Huynh et al. Neurobiol Aging. 2012 33(5):1005.e11-22) Considering that said reference value is said basal level, thus said level in Alzheimer's disease is increased by at least 50% in the hippocampus and the cortex.

In an advantageous embodiment, the level and/or activity of heparan sulfate is further increased by 60% compared to the basal level and/or activity in the hippocampus and the cortex.

In an advantageous embodiment, the level and/or activity of heparan sulfate is further increased by 70% compared to the basal level and/or activity in the hippocampus and the cortex.

In an advantageous embodiment, the level and/or activity of heparan sulfate is further increased by 80% compared to the basal level and/or activity in the hippocampus and the cortex.

In an advantageous embodiment, the level and/or activity of heparan sulfate is further increased by 90% compared to the basal level and/or activity in the hippocampus and the cortex.

In an advantageous embodiment, the level and/or activity of heparan sulfate is further increased by 100% compared to the basal level and/or activity in the hippocampus and the cortex.

In an advantageous embodiment, the present invention relates to an in vitro method wherein said neurodegenerative disease is an Alzheimer's disease, wherein
said level of the transcription product of the gene set forth by SEQ ID NO: 1 is increased by at least 100% as determined by real time PCR and/or
said level of the transcription product of the gene set forth by SEQ ID NO: 3 is increased by at least 100% as determined by real time PCR and/or
said level of the translation product of the gene and set forth by SEQ ID NO: 2 is increased by at least 50% and/or
said level of the translation product of the gene and set forth by SEQ ID NO: 4 is increased by at least 50% as determined by Western Blot, ELISA, mass spectrometry or immunohistochemistry methods as defined above,
comprising further determining the level and/or activity of heparan sulfate liable to bind to Tau protein, an increase of at least 50% of said level and/or activity compared to a reference value being indicative of Alzheimer's disease.

Several sulfated glycosaminoglycans and mimetics can bind Tau, this includes heparan sulfates, chondroitin sulfate, keratan sulfate and other sulfated polysaccharides from chemical synthesis as dextran sulfate and pentosan sulfates.

In an advantageous embodiment, the level and/or activity of heparan sulfate is further increased by 60% compared to said reference value.

In an advantageous embodiment, the level and/or activity of heparan sulfate is further increased by 70% compared to said reference value.

In an advantageous embodiment, the level and/or activity of heparan sulfate is further increased by 80% compared to said reference value.

In an advantageous embodiment, the level and/or activity of heparan sulfate is further increased by 90% compared to said reference value.

In an advantageous embodiment, the level and/or activity of heparan sulfate is further increased by 100% compared to said reference value.

In an advantageous embodiment, the level and/or activity of heparan sulfate is further increased by 110% compared to said reference value.

In an advantageous embodiment, the level and/or activity of heparan sulfate is further increased by 120% compared to said reference value.

In an advantageous embodiment, the level and/or activity of heparan sulfate is further increased by 130% compared to said reference value.

In an advantageous embodiment, the level and/or activity of heparan sulfate is further increased by 140% compared to said reference value.

In an advantageous embodiment, the level and/or activity of heparan sulfate is further increased by 150% or more compared to said reference value.

In an advantageous embodiment, said level and/or activity of heparan sulfate is determined in human hippocampus, cortex, CSF or blood.

The basal level of heparan sulfate in a control human hippocampus is about 0.5 µg/mg of wet tissue as determined by the dimethylmethylene blue (DMMB) assay described by Huynh et al. (Neurobiol Aging. 2012 33(5):1005.e11-22).

Considering that said reference value is said basal level, thus said level and/or activity of heparan sulfate is increased in Alzheimer's disease by 50% in the hippocampus.

In an advantageous embodiment, said level and/or activity of heparan sulfate is further increased by 60% compared to the basal level and/or activity in the hippocampus.

In an advantageous embodiment, said level and/or activity of heparan sulfate is further increased by 70% compared to the basal level and/or activity in the hippocampus.

In an advantageous embodiment, said level and/or activity of heparan sulfate is further increased by 80% compared to the basal level and/or activity in the hippocampus.

In an advantageous embodiment, said level and/or activity of heparan sulfate is further increased by 90% compared to the basal level and/or activity in the hippocampus.

In an advantageous embodiment, said level and/or activity of heparan sulfate is further increased by 100% compared to the basal level and/or activity in the hippocampus.

In an advantageous embodiment, said level and/or activity of heparan sulfate is further increased by 110% compared to the basal level and/or activity in the hippocampus.

In an advantageous embodiment, said level and/or activity of heparan sulfate is further increased by 120% compared to the basal level and/or activity in the hippocampus.

In an advantageous embodiment, said level and/or activity of heparan sulfate is further increased by 130% compared to the basal level and/or activity in the hippocampus.

In an advantageous embodiment, said level and/or activity of heparan sulfate is further increased by 140% compared to the basal level and/or activity in the hippocampus.

In an advantageous embodiment, said level and/or activity of heparan sulfate is further increased by 150% or more compared to the basal level and/or activity in the hippocampus.

In an advantageous embodiment, the present invention relates to an in vitro method wherein said neurodegenerative disease is an Alzheimer's disease, wherein
said level of the transcription product of the gene set forth by SEQ ID NO: 1 is increased by at least 100% as determined by real time PCR and/or
said level of the transcription product of the gene set forth by SEQ ID NO: 3 is increased by at least 100% as determined by real time PCR and/or
said level of the translation product of the gene and set forth by SEQ ID NO: 2 is increased by at least 50% and/or
said level of the translation product of the gene and set forth by SEQ ID NO: 4 is increased by at least 50% as determined by Western Blot, ELISA, mass spectrometry or immunohistochemistry methods as defined above,
comprising further determining the level and/or activity of 3-O-sulfated heparan sulfate, an increase of at least 50% of said level compared to the basal level and/or activity being indicative of Alzheimer's disease.

The inventors have found that among the heparan sulfate, in particular the heparan sulfate liable to bind to Tau protein, the 3-O-sulfated heparan sulfate, are highly increased allowing thus to diagnose an Alzheimer's disease.

Said increase in Alzheimer's disease is observed in the hippocampus, cortex, CSF and blood.

In an advantageous embodiment, said level and/or activity of 3-O-sulfated heparan sulfate is further increased by 60% compared to said reference value.

In an advantageous embodiment, said level and/or activity of 3-O-sulfated heparan sulfate is further increased by 70% compared to said reference value.

In an advantageous embodiment, said level and/or activity of 3-O-sulfated heparan sulfate is further increased by 80% compared to said reference value.

In an advantageous embodiment, said level and/or activity of 3-O-sulfated heparan sulfate is further increased by 90% compared to said reference value.

In an advantageous embodiment, said level and/or activity of 3-O-sulfated heparan sulfate is further increased by 100% compared to said reference value.

In an advantageous embodiment, said level and/or activity of 3-O-sulfated heparan sulfate is further increased by 110% compared to said reference value.

In an advantageous embodiment, said level and/or activity of 3-O-sulfated heparan sulfate is further increased by 120% compared to said reference value.

In an advantageous embodiment, said level and/or activity of 3-O-sulfated heparan sulfate is further increased by 130% compared to said reference value.

In an advantageous embodiment, said level and/or activity of 3-O-sulfated heparan sulfate is further increased by 140% compared to said reference value.

In an advantageous embodiment, said level and/or activity of 3-O-sulfated heparan sulfate is further increased by 150% or more compared to said reference value.

The basal level of 3-O-sulfated heparan sulfate in a control human hippocampus is about 1 ng/ml of wet tissue as determined by the dimethylmethylene blue (DMMB) assay.

In an advantageous embodiment, the level and/or activity of 3-O-sulfated heparan sulfate is further increased by 60% compared to the basal level and/or activity in the hippocampus.

In an advantageous embodiment, the level and/or activity of 3-O-sulfated heparan sulfate is further increased by 70% compared to the basal level and/or activity in the hippocampus.

In an advantageous embodiment, the level and/or activity of 3-O-sulfated heparan sulfate is further increased by 80% compared to the basal level and/or activity in the hippocampus.

In an advantageous embodiment, the level and/or activity of 3-O-sulfated heparan sulfate is further increased by 90% compared to the basal level and/or activity in the hippocampus.

In an advantageous embodiment, the level and/or activity of 3-O-sulfated heparan sulfate is further increased by 100% compared to the basal level and/or activity in the hippocampus.

In an advantageous embodiment, the level and/or activity of 3-O-sulfated heparan sulfate is further increased by 110% compared to the basal level and/or activity in the hippocampus.

In an advantageous embodiment, the level and/or activity of 3-O-sulfated heparan sulfate is further increased by 120% compared to the basal level and/or activity in the hippocampus.

In an advantageous embodiment, the level and/or activity of 3-O-sulfated heparan sulfate is further increased by 130% compared to the basal level and/or activity in the hippocampus.

In an advantageous embodiment, the level and/or activity of 3-O-sulfated heparan sulfate is further increased by 140% compared to the basal level and/or activity in the hippocampus.

In an advantageous embodiment, the level and/or activity of 3-O-sulfated heparan sulfate is further increased by 150% or more compared to the basal level and/or activity in the hippocampus.

In an advantageous embodiment, said 3-O-sulfated heparan sulfate is selected from the trisulfated GlcA2S/IdoA2S-GlcNS3S and the—tetrasulfated GlcA2S/IdoA2S-GlcNS3S6S unit forms, and the biological fluid is CSF after heparinases I-III digestion of heparan sulfate.

A representative structure of 3-O-sulfated heparan sulfate is the following:

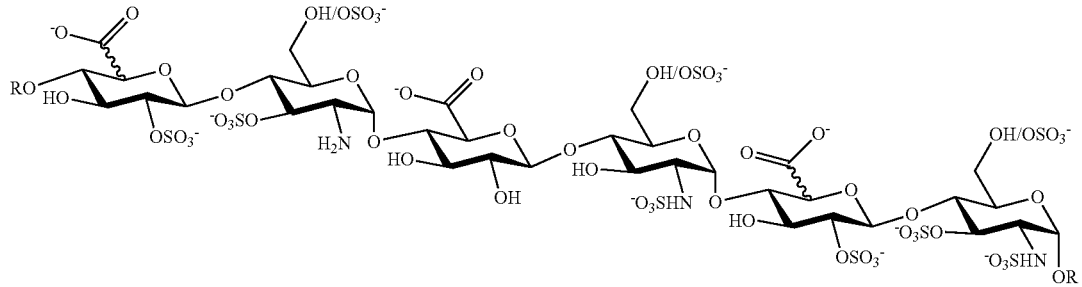

-OR: represents HS chain
-OH/OSO$_3^-$ means either a -OH or a -OSO$_3^-$ group
-NH$_2$/SO$_3^-$ means either a -NH$_2$ or a -NHSO$_3^-$ group In an advantageous embodiment, the present invention relates to one of the methods of diagnosis or prognostic or follow-up of a neurodegenerative disease in a subject, or determining whether a subject is at increased risk of developing said neurodegenerative disease in a subject as defined above, comprising further determining the level and/or activity of abnormal phosphorylation of Tau protein and/or total Tau protein, an increase of at least 10% compared to a respective reference value being indicative of Alzheimer's disease.

In an advantageous embodiment, said level and/or activity of abnormal phosphorylation of Tau protein is increased by at least 20% compared to a reference value.

In an advantageous embodiment, said level and/or activity of abnormal phosphorylation of Tau protein is increased by at least 30% compared to a reference value.

In an advantageous embodiment, said level and/or activity of abnormal phosphorylation of Tau protein is increased by at least 40% compared to a reference value.

In an advantageous embodiment, said level and/or activity of abnormal phosphorylation of Tau protein is increased by at least 50% compared to a reference value.

In an advantageous embodiment, said level and/or activity of abnormal phosphorylation of Tau protein is increased by at least 60% compared to a reference value.

In an advantageous embodiment, said level and/or activity of abnormal phosphorylation of Tau protein is increased by at least 70% compared to a reference value.

In an advantageous embodiment, said level and/or activity of abnormal phosphorylation of Tau protein is increased by at least 80% compared to a reference value.

In an advantageous embodiment, said level and/or activity of abnormal phosphorylation of Tau protein is increased by at least 90% compared to a reference value.

In an advantageous embodiment, said level and/or activity of abnormal phosphorylation of Tau protein is increased by at least 100% compared to a reference value.

In an advantageous embodiment, said level and/or activity of abnormal phosphorylation of Tau protein is increased by at least 10%, 20%, 30%, 40%, 50%, 60%, 70%, 80%, 90% or 100% compared to said reference value and said level and/or activity of total Tau protein is increased by at least 10%, 20%, 30%, 40%, 50%, 60%, 70%, 80%, 90% or 100% compared to said reference value.

The basal value in human CSF for pTau is about or less than 60 pg/ml and for total Tau is about or less than 450 pg/ml).

In an advantageous embodiment, said level and/or activity of abnormal phosphorylation of Tau protein is increased by at least 20% compared to said basal value.

In an advantageous embodiment, level and/or activity of abnormal phosphorylation of Tau protein is increased by at least 30% compared to said basal value.

In an advantageous embodiment, level and/or activity of abnormal phosphorylation of Tau protein is increased by at least 40% compared to said basal value.

In an advantageous embodiment, said level and/or activity of abnormal phosphorylation of Tau protein is increased by at least 50% compared to said basal value.

In an advantageous embodiment, said level and/or activity of abnormal phosphorylation of Tau protein is increased by at least 60% compared to said basal value.

In an advantageous embodiment, said level and/or activity of abnormal phosphorylation of Tau protein is increased by at least 70% compared said basal value.

In an advantageous embodiment, said level and/or activity of abnormal phosphorylation of Tau protein is increased by at least 80% compared to said basal value.

In an advantageous embodiment, said level and/or activity of abnormal phosphorylation of Tau protein is increased by at least 90% compared to said basal value.

In an advantageous embodiment, said level and/or activity of abnormal phosphorylation of Tau protein is increased by at least 100% compared to said basal value.

In an advantageous embodiment, said level and/or activity of total Tau protein is increased by at least 10% compared to said basal value.

In an advantageous embodiment, said level and/or activity of total Tau protein is increased by at least 20% compared to said basal value.

In an advantageous embodiment, said level and/or activity of abnormal phosphorylation of Tau protein is increased by at least 30% compared to said basal value.

In an advantageous embodiment, said level and/or activity of total Tau protein is increased by at least 40% compared to said basal value.

In an advantageous embodiment, said level and/or activity of total Tau protein is increased by at least 50% compared to said basal value.

In an advantageous embodiment said level and/or activity of total Tau protein is increased by at least 60% compared to said basal value.

In an advantageous embodiment, said level and/or activity of total Tau protein is increased by at least 70% compared said basal value.

In an advantageous embodiment, said level and/or activity of total Tau protein is increased by at least 80% compared to said basal value.

In an advantageous embodiment, said level and/or activity of total Tau protein is increased by at least 90% compared to said basal value.

In an advantageous embodiment, said level and/or activity of total Tau protein is increased by at least 100% compared to said basal value.

In an advantageous embodiment, said level and/or activity of abnormal phosphorylation of Tau protein is increased by at least 10%, 20%, 30%, 40%, 50%, 60%, 70%, 80%, 90% or 100% compared to said basal value and said level and/or activity of total Tau protein is increased by at least 10%, 20%, 30%, 40%, 50%, 60%, 70%, 80%, 90% or 100% compared to said basal value.

The present invention shows results in where 3-OST-2 enzyme is present in CSF in AD patients and that the levels of the protein correlate with levels of hyperphosphorylated Tau in the same CSF samples. This demonstrates that the enzyme can, as Tau protein, be found in the extracellular space and thus pass to CSF and confirm that measure of its levels, or the measure of its activity, can be used as a diagnostic, and/or prognostic marker of AD disease.

In an advantageous embodiment, the present invention relates to one of the method of diagnosis or prognostic or follow-up of a neurodegenerative disease in a subject, or determining whether a subject is at increased risk of developing said neurodegenerative disease in a subject as defined above, wherein said biological fluid is the CSF and said activity and/or level of:
  a) at least one gene selected from the group consisting of the nucleotidic sequences set forth by SEQ ID NO: 1 and SEQ ID NO: 3 and coding for an heparin-glucosamine 3-O-sulfotransferase 2 and 4 respectively, and/or
  b) at least one transcription product of a gene selected from the group consisting of the nucleotidic sequences set forth by SEQ ID NO: 1 and SEQ ID NO: 3 and coding for an heparin-glucosamine 3-O-sulfotransferase, and/or
  c) translation product of said genes, said products being set forth respectively by SEQ ID NO: 2 and 4, and
  d) heparan sulfate, in particular 3-O-sulfated heparan sulfate, notably 3-O-sulfated heparan sulfate disaccharide, and e) said activity and/or level of abnormal phosphorylation of the Tau protein and/or total Tau protein, are increased in said subject compared to said respective reference value.

It must be noted that the increase of the level and/or activity of said gene and said transcription product of said gene and said translation product of said gene and HS could be increased before the increase of the abnormal phosphorylation of the Tau protein and/or total Tau protein.

In another aspect, the present invention relates to a method of treating or preventing a neurodegenerative disease, in a subject, comprising the administration to said subject in a therapeutically or prophylactically effective amount at least one agent which directly or indirectly affects an activity and/or a level of:
   a) at least one gene selected from the group consisting of the nucleotidic sequences set forth by SEQ ID NO: 1 and SEQ ID NO: 3 and coding for an heparin-glucosamine 3-O-sulfotransferase, and/or
   b) at least one transcription product of a gene selected from the group consisting of the nucleotidic sequences set forth by SEQ ID NO: 1 and SEQ ID NO: 3 and coding for an heparin-glucosamine 3-O-sulfotransferase, and/or
   c) at least one translation product of said genes, said products being set forth respectively by SEQ ID NO: 2 and 4, and/or
   d) a fragment or derivative or variant of said gene or said transcription or translation product,
   e) heparan sulfate, in particular 3-O-sulfated heparan sulfate, notably 3-O-sulfated heparan sulfate disaccharide,
   f) abnormal phosphorylated Tau protein and/or total Tau protein, In an advantageous embodiment, the present invention relates to a method of treating or preventing a neurodegenerative disease, in a subject as defined above, wherein said agent is a polysaccharide or an oligosaccharide having a molecular weight from about 2000 to about 20 000 Daltons, preferably of about 20 000 Daltons, in particular an heparan sulfate mimetic, such as F6 molecule, CR36, HM100 or HM 2602, or fucoidan, or pentosan polysulfate, or in particular a pentasaccharide, such as Arixtra® (fondaparinux), fucoidan, or pentosan polysulfate, and/or low molecular weight heparins as enoxaparin (Lovenox®), and/or ultralow molecular weight heparins.

In an advantageous embodiment, the present invention relates to a method of treating or preventing a neurodegenerative disease, in a subject, as defined above, wherein said agent is a polysaccharide or an oligosaccharide having a molecular weight of about 20 000 Daltons, in particular an heparan sulfate mimetic, such as F6 molecule and wherein said agent is administered at a dose comprised from about 1.5 mg/Kg to about 50 mg/Kg by intravenous route.

Said agent can also be administered by another route as oral at about 50 mg/kg to about 500 mg/kg, in particular 100 to 200 mg/kg or i.p . . . at an appropriate dosage for said routes.

In an advantageous embodiment, the present invention relates to a method of treating or preventing a neurodegenerative disease, in a subject, as defined above, wherein said agent is an oligonucleotide, such as a siRNA selected from the list consisting of: sense siRNA set forth by SEQ ID NO: 71 and antisense siRNA set forth by SEQ ID NO: 72, sense siRNA set forth by SEQ ID NO: 73 and antisense siRNA set forth by SEQ ID NO: 74, sense siRNA set forth by SEQ ID NO: 75 and antisense siRNA set forth by SEQ ID NO: 76, sense siRNA set forth by SEQ ID NO: 77 and antisense siRNA set forth by SEQ ID NO: 78, or a morpholino antisense oligonucleotide, and said activity and/or level directly or indirectly affected is the transcription product of at least one gene selected from the group consisting of the nucleotidic sequences set forth by SEQ ID NO: 1 and SEQ ID NO: 3, said level of at least one transcription product being decreased, in particular equal to about at least 50% of the original value.

In an advantageous embodiment, the present invention relates to a method of treating or preventing a neurodegenerative disease, in a subject, as defined above, said agent being an oligonucleotide, such as a morpholino antisense oligonucleotide, and wherein said at least one gene is set forth by SEQ ID NO: 1 and said oligonucleotide is set forth by SEQ ID NO: 5.

In an advantageous embodiment, the present invention relates to a method of treating or preventing a neurodegenerative disease, in a subject, as defined above, said agent being an oligonucleotide, such as a morpholino antisense oligonucleotide, and wherein said gene is set forth by SEQ ID NO: 3 and said oligonucleotide is set forth by SEQ ID NO: 6.

In an advantageous embodiment, the present invention relates to a method of treating or preventing a neurodegenerative disease, in a subject, as defined above, said agent being an oligonucleotide, such as a morpholino antisense oligonucleotide, wherein said at least one gene consists in the two genes set forth by SEQ ID NO: 1 and SEQ ID NO: 3, said oligonucleotide for the gene set forth by SEQ ID NO:1 being set forth by SEQ ID NO: 5 and said oligonucleotide for the gene set forth by SEQ ID NO: 3 being set forth by SEQ ID NO: 6

In an advantageous embodiment, the present invention relates to a method of treating or preventing a neurodegenerative disease, in a subject, as defined above, said agent being an oligonucleotide, such as a morpholino antisense oligonucleotide, wherein said agent is administered at a dose comprised from 0.1 to 1 mM, in particular 0.5 mM by intraveinous route.

Said agent can also be administered by another route as oral, i.p . . . at appropriate dosage for said routes.

In an advantageous embodiment, the present invention relates to a method of treating or preventing a neurodegenerative disease, in a subject, as defined above, wherein said agent is a polysaccharide, preferably a pentasaccharide, such as Arixtra® (fondaparinux), fucoidan, or pentosan polysulfate, and/or low molecular weight heparins as enoxaparin (Lovenox®), and/or ultralow molecular weight heparins, and said activity and/or level directly or indirectly affected is the translation product of the gene set forth respectively by SEQ ID NO: 2.

This invention is not limited to a polysaccharide, any heparin type product can be used as said agent.

In an advantageous embodiment, the present invention relates to a method of treating or preventing a neurodegenerative disease, in a subject, as defined above, wherein said agent being a polysaccharide, preferably a saccharide, such as Arixtra® (fondaparinux), fucoidan, or pentosan polysulfate, and/or low molecular weight heparins as enoxaparin (Lovenox®), and/or ultralow molecular weight heparins, wherein said agent is administered at a dose comprised from about 1.5 mg/Kg to about 50 mg/Kg by intravenous route.

Said agent can also be administered by another route as oral at about 50 mg/kg to about 500 mg/kg, in particular 100 to 200 mg/kg or i.p at an appropriate dosage for said routes.

In an advantageous embodiment, the present invention relates to a method of treating or preventing a neurodegenerative disease, in a subject, as defined above, wherein said agent is a small molecule, inhibitor of heparin and heparan sulfate actions, such as protamine or protamine sulfate.

In an advantageous embodiment, the present invention relates to a method of treating or preventing a neurodegenerative disease, in a subject, as defined above, said agent being a small molecule, wherein said agent is administered at a dose comprised from 1.0 mg/Kg to about 50 mg/Kg by intraveinous route.

Said agent can also be administered by another route as oral at about 50 mg/kg to about 500 mg/kg, in particular 100 to 200 mg/kg or i.p. at appropriate dosage.

In another aspect, the present invention relates to a method of treating or preventing a neurodegenerative disease, in a subject, comprising the administration to said subject in a therapeutically or prophylactically effective amount at least one agent which directly or indirectly affects an activity and/or a level of heparan sulfate.

Inhibitors of 3-O-sulfatation or inhibitors of sulfotransferases of heparan sulfate can be used in this embodiment, in particular those described in Razi, N et al. (J Biol Chem 1995, 270, 11267-75); in Rath, V. L. et al. (Drug Discov Today 2004, 9, 1003-11) or in Seko, A. et al. (J Inorg Biochem 2009, 103, 1061-6).

Inhibitors of heparan sulfate described in US20100048638 can also be used.

In an advantageous embodiment, the present invention relates to a method of treating or preventing a neurodegenerative disease, in a subject, comprising the administration to said subject in a therapeutically or prophylactically effective amount at least one agent which directly or indirectly affects an activity and/or a level of heparan sulfate, as defined above, wherein said at least agent further directly or indirectly affects the level of abnormal phosphorylation of the Tau protein and/or total Tau protein.

In an advantageous embodiment, the present invention relates to a method of treating or preventing a neurodegenerative disease, in a subject, comprising the administration to said subject in a therapeutically or prophylactically effective amount at least one agent which directly or indirectly affects an activity and/or a level of heparan sulfate and directly or indirectly affects the level of abnormal phosphorylation of the Tau protein and/or total Tau protein, as defined above, wherein agent is administered at a dose comprised from about 0.5 mg/Kg to about 50 mg/Kg by intravenous route.

Said agent can also be administered by another route as oral at about 50 mg/kg to about 500 mg/kg, in particular 100 to 200 mg/kg or i.p. . . . at appropriate dosage for said routes.

In another aspect, the present invention relates to a method for an in vitro screening for a modulator of neurodegenerative diseases, advantageously a Tauopathy, in particular Alzheimer's disease, provided that said neurodegenerative disease is different from a prion disease, comprising:
a) contacting a brain cell of a mammal with a neurodegenerative disease, with a compound to test,
b) determining the activity and/or a level of:
    i. at least one gene selected from the group consisting of the nucleotidic sequences set forth by SEQ ID NO: 1 and SEQ ID NO: 3 and coding for an heparin-glucosamine 3-O-sulfotransferase, and/or
    ii. at least one transcription product of a gene selected from the group consisting of the nucleotidic sequences set forth by SEQ ID NO: 1 and SEQ ID NO: 3 and coding for an heparin-glucosamine 3-O-sulfotransferase, and/or
    iii. at least one translation product of said genes, said products being set forth respectively by SEQ ID NO: 2 and 4, and/or
    iv. a fragment or derivative or variant of said gene or transcription or translation product, and/or
    v. heparan sulfate, in particular the level of 3-O-sulfated heparan sulfate, notably the level of 3-O-sulfated heparan sulfate disaccharides, and/or
    vi. abnormal phosphorylation of the Tau protein and/or total Tau protein,
c) determining said activity and/or a level in a control brain cell of a mammal with a neurodegenerative disease not contacted with said compound,
d) comparing the difference of said activity and/or a level in the contacted cell with the one in the non contacted cell, wherein an alteration in said activity and/or level of the contacted cell indicates that the test compound is a modulator of said disease.

In an advantageous embodiment, in the above in vitro screening, when said activity and/or the level determined in step b) is the one of:
heparan sulfate, or
of abnormal phosphorylation of the Tau protein and/or total Tau protein,
therefore, the activities and/or levels heparan sulfate and abnormal phosphorylation of the Tau protein and/or total Tau protein are both determined, or
the activity and/or the level of at least one other element chosen among said gene, said transcription product of said genes, said translation product of said genes, or said fragment or derivative or variant of said gene or said transcription or translation product is also determined.

In another aspect, the present invention relates to a method for an in vitro screening for a modulator of neurodegenerative diseases, advantageously a Tauopathy, in particular Alzheimer's disease, provided that said neurodegenerative disease is different from a prion disease, comprising:
a) contacting a brain cell of a mammal with a neurodegenerative disease, with a compound to test,
b) determining the binding of abnormal phosphorylation of the Tau protein and/or total Tau protein to immobilized heparin,
c) determining said binding in a control brain cell of a mammal with a neurodegenerative disease not contacted with said compound,
d) comparing the difference of said binding in the contacted cell with the one in the non contacted cell, wherein an alteration in said binding of the contacted cell indicates that the test compound is a modulator of said disease.

In another aspect, the present invention relates to a method for an in vivo screening for a modulator of neurodegenerative diseases, advantageously a Tauopathy, in particular Alzheimer's disease, provided that said neurodegenerative disease is different from a prion disease, comprising:
a) administering a test compound to a test animal which is predisposed or has already developed symptoms of a neurodegenerative disease,
b) determining in said animal the activity and/or a level of:
    i. at least one gene selected from the group consisting of the nucleotidic sequences set forth by SEQ ID NO: 1 and SEQ ID NO: 3 and coding for an heparin-glucosamine 3-O-sulfotransferase, and/or ii. at least one transcription product of a gene selected from the group consisting of the nucleotidic sequences set forth by SEQ ID NO: 1 and SEQ ID NO: 3 and coding for an heparin-glucosamine 3-O-sulfotransferase, and/or iii. at least one translation product of said genes, said products being set forth respectively by SEQ ID NO: 2 and 4, and/or iv. a fragment or derivative or variant of said gene or said transcription or translation product, and/or v. heparan sulfate, in particular the level of 3-O-sulfated heparan sulfate, notably the level of 3-O-sulfated heparan sulfate disaccharides, and/or vi. abnormal phosphorylation of the Tau protein and/or total Tau protein, c) determining said activity and/or a level in a control animal which is predisposed or has already developed symptoms of a neurodegenerative disease, not contacted with said compound, d) comparing the difference of said activity and/or a level in the contacted animal with the one of the non contacted animal, wherein an alteration in said activity and/or level of the contacted animal indicates that the test compound is a modulator of said disease.

In an advantageous embodiment, in the above in vivo screening, when said activity and/or the level determined in step b) is the one of:

heparan sulfate, or of abnormal phosphorylation of the Tau protein and/or total Tau protein, therefore, the activities and/or levels heparan sulfate and abnormal phosphorylation of the Tau protein and/or total Tau protein are both determined, or the activity and/or the level of at least one other element chosen among said gene, said transcription product of said genes, said translation product of said genes, or said fragment or derivative or variant of said gene or said transcription or translation product is also determined.

In another aspect, the present invention relates to a method for an in vivo screening for a modulator of neurodegenerative diseases, advantageously a Tauopathy, in particular Alzheimer's disease, provided that said neurodegenerative disease is different from a prion disease, comprising:

a) administering a test compound to a test animal which is predisposed or has already developed symptoms of a neurodegenerative disease, b) determining the binding of abnormal phosphorylation of the Tau protein and/or total Tau protein to immobilized heparin, c) determining said binding in a control animal which is predisposed or has already developed symptoms of a neurodegenerative disease, not contacted with said compound, d) comparing the difference of said binding in the contacted animal with the one of the non contacted animal, wherein an alteration in said activity and/or level of the contacted animal indicates that the test compound is a modulator of said disease.

In preferred embodiment, the present invention relates to a method for an in vivo screening for a modulator of neurodegenerative diseases, in particular Alzheimer's disease, as defined above, wherein said animal is a mouse such as a SAMP8 mouse and/or the 3xTg-AD mice model of AD.

In preferred embodiment, the present invention relates to a method for an in vivo screening for a modulator of neurodegenerative diseases, in particular Alzheimer's disease, as defined above, wherein said animal is Zebra fish.

DESCRIPTION OF THE FIGURES

FIGS. 2A to 2C present the increased total sulfated GAGs (2A) and particularly total HS (2B) sulfate levels in the hippocampus of AD postmortem brains compared to GAGs and HS from age-matched normal control brains (individuals and brains characteristics are described in Table I). The DMMB assay (Huynh et al, neurobiology of aging 2010) was used to detect and quantify the GAGs and HS levels in the postmortem brain samples. FIG. 2A: total GAG (μg/mg of tissue). White histogram: control. Black histogram: Patient with AD.

FIG. 2B: total HS (μg/mg of tissue). White histogram: control Black histogram: Patient with AD.

FIG. 2C: Left upper square (a): control brain; right upper square (b): plaques and tangles in AD brain. Left lower square (c): plaques in in AD brain; right lower square (d): tangles in AD brain.

TABLE 1

Characteristics of the subjects providing brains tissues.

| Sex | Age (years) | PMD[a] (h) | Group | Immediate ause of death[b] | Senile plaques[c]/ mm$^2$ | CERAD/ Braak and Braak[d] |
|---|---|---|---|---|---|---|
| M | 62 | 20.2 | Control | Myocardial infarctation | 32 | I |
| M | 65 | 8.2 | Control | Hemotorax trauma | 47 | 0 |
| M | 65 | 8.6 | Control | Guns shot | 51 | I |
| F | 73 | 15.3 | Control | Brochopneumonia | 65 | II |
| M | 61 | 9.3 | Control | PuDlmonar trombosis | 36 | 0 |
| F | 64 | 14.3 | Control | Liver traumatic rupture | 41 | I |
| M | 60 | 21.0 | Control | Bronchopneumonia | 44 | 0 |
| F | 76 | 24.0 | Control | Myocardio infarctation | 65 | I |
| Mean ± SD | 67.8 ± 2.9 | 15.1 ± 2.2 | | | | |

TABLE 1-continued

Characteristics of the subjects providing brains tissues.

| Sex | Age (years) | PMD[a] (h) | Group | Immediate ause of death[b] | Senile plaques[c]/ mm$^2$ | CERAD/ Braak and Braak[d] |
|---|---|---|---|---|---|---|
| M | 84 | 19.0 | AD | Bronchopneumonia | 78 | IV |
| F | 70 | 10.3 | AD | Bronchopneumonia | 65 | III |
| F | 98 | 14.2 | AD | Bronchopneumonia | 87 | III |
| M | 84 | 14.0 | AD | Aortic rupture | 84 | IV |
| F | 82 | 9.2 | AD | Traumatic torax | 87 | III |
| F | 75 | 19.2 | AD | Pulmonar trombosis | 80 | IV |
| F | 69 | 5.4 | AD | Myocardial infarctation | 76 | IV |
| M | 82 | 21.2 | AD | Myocardial infarctation | 80 | III |
| Mean ± SD | 76.8 ± 3.5 | 14.1 ± 2.0 | | | | |

[a]PMD: post mortem delay. No significant PMD statistical difference (p = 0.7249) was found between the two groups.
[b]Subjects died from guns shot diagnosis do not have traumatic brain lesions.
[c]Senile plaques and NFT values represent an arithmetic mean (Mean ± SEM) calculated from the counts of six fields for each observed region.
[d]CERAD score (A, B, or C)/Braak and Braak stage (I to VI).

FIG. 3 presents the transcript levels of sulfotransferases and some other enzymes implicated in HS biosynthesis.
NS: No significant change in enzyme expression
ND: the enzyme was not detected FIGS. 4A to 4H present the colocalization of HS and hyperphosphorylated Tau in hippocampus from AD subjects and age-matched controls.

Cryosections from Alzheimer's disease (AD) and aged matched human hippocampus were incubated with anti-HS (10E4) (FIGS. 4A and B) and anti Tau 262 (FIGS. 4C and D) antibodies, followed by labelling with secondary antibodies targeted with fluoroprobes Alexa 568 and Alexa 488.

Sections were labelled with DAPI (FIGS. 4E and F), the right panel shows overlay (FIGS. 4G and H), scale bar 50 µm.

Figure 1:
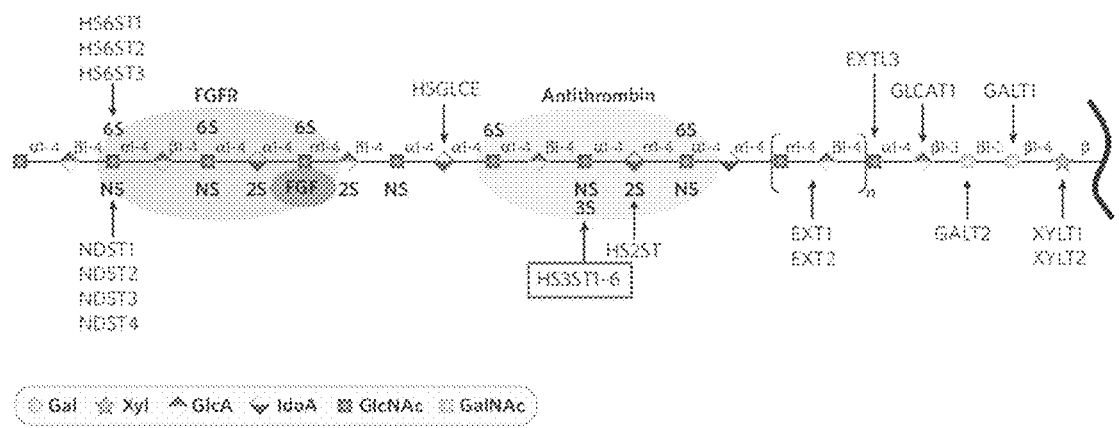
FIG. 1 presents the assembly of heparan sulfate (HS) and resulting binding sites for known ligands including FGF, FGFR and antithrombin. Sulfation of the 3-O-position of glucosamine residues is catalyzed by the family of heparan sulfate (glucosamine) 3-O-sulfotransferases HS 3-O-sulfotransferases-1 to -6 (HS3ST1-6). This 3-O-sulfation is the last metabolic modification in the heparan sulfate biosynthesis (Bishop et al., 2007, Heparan sulphate proteoglycans fine-tune mammalian physiology. Nature 446:1030-1037), it is not related to any trophic function of heparan sulfates and is largely the minor sulfated form of these sugars since very lowly expressed in tissues (about 0.2% of total HS).
Figure 5:

FIG. 5 presents the levels of the 3-OST-2 (HS3ST2) protein in cerebrospinal fluid (CSF) of AD patients compared to the level of phosphorylated tau protein (pTau, Ser231 epitope) in the same samples. Western blot was used to detect and compare the proteins levels in samples.

Figures 6A, 6B:
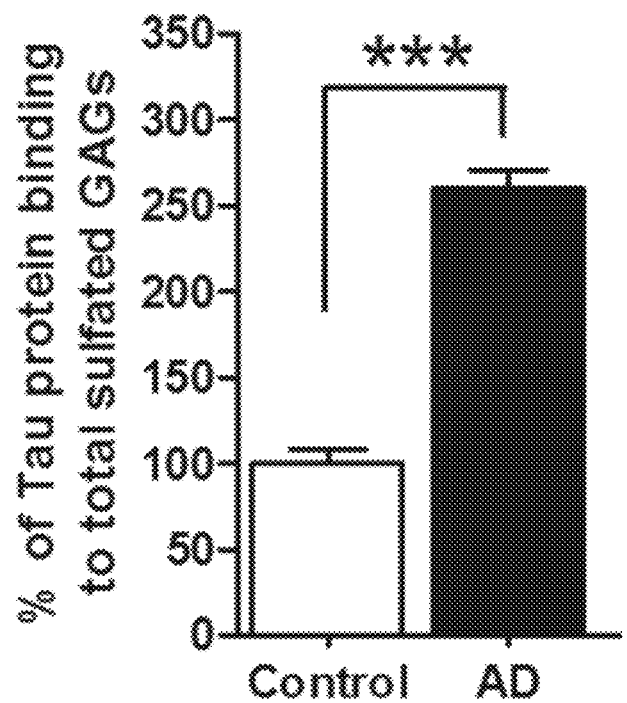

FIGS. 6A and 6B presents the higher capacity of GAGs extracted from hippocampus of AD to bind to human tau protein compared to GAGs from age-matched normal control brains. An ELISA test was used to compare the capacity of the different GAGs to bind to tau protein. The ELISA competing assay used immobilized heparin to bind au in the absence of competing GAGs. For the assay, GAGs (used from 0.1 to 1000 ng/mL) were added to the ELISA together with the tau protein (used at 100 ng/mL). After 1 h incubation at 4° C. plates were washed and remaining tau signal was recorded in the plate. X-axis: % Tau protein binding to total sulfated GAGs. EC50 stands for the GAG concentration necessary to inhibit 50% of the tau protein binding to immobilized heparin. Y-axis: Control (white histogram), AD (black histogram).

FIG. 6A GAGs binding to Tau protein as determined by the ELISA type competing Signal given by control GAGs was considered as 100% effect.

X-axis: % Tau protein binding to total sulfated GAGs.
Y-axis: Control (white histogram), AD (black histogram).

FIG. 6B Changes in the binding capacities of total GAGs to Tau as determined by the ELISA type competing assay. EC$_{50}$ stands for the GAG concentration necessary to inhibit 50% of the factor binding to immobilized heparin.

Figures 7A, 7B:
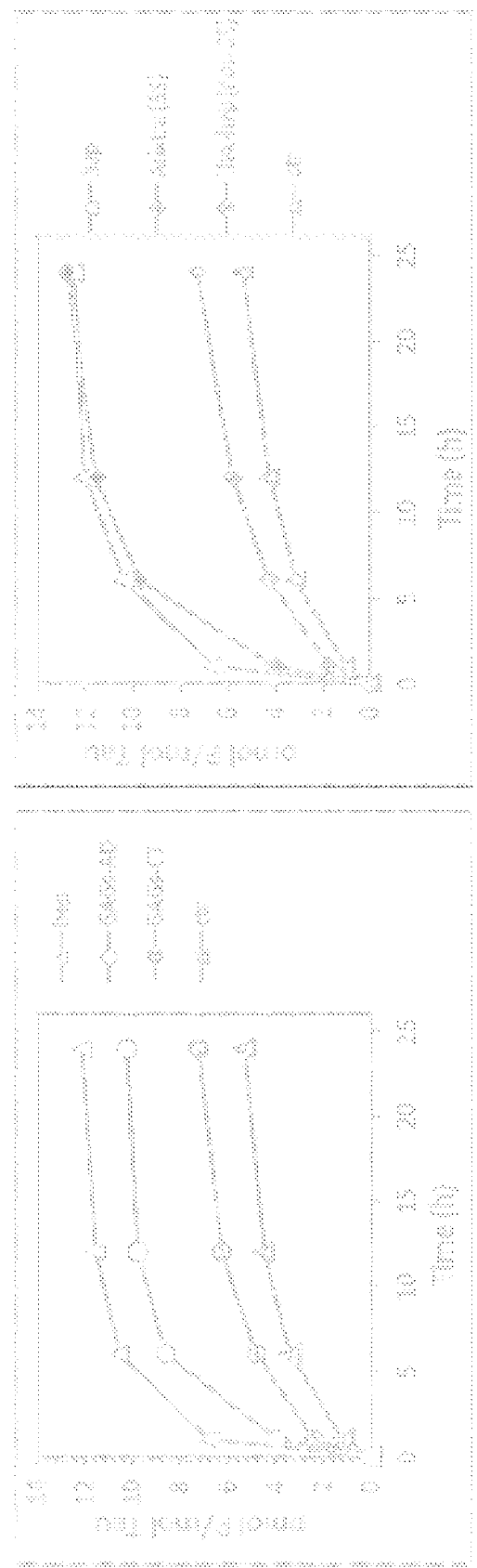

FIGS. 7A and 7B present the effect of GAG and heparin on in vitro Tau abnormal Tau phosphorylation.

FIG. 7A presents increased effect of GAGs extracted from hippocampus of AD (GAGs-AD) to induce the abnormal pathological phosphorylation of recombinant human tau protein (441-amino acid isoform of human Tau) by glycogen synthase kinase 3 (GSK-3) compared to the effect of GAGs from age-matched brains (GAGs-CT). Antibody Tau396 was used to detect the abnormally phosphorylated tau formation.
x-axis: time (h)
y-axis: pmol P Tau/mol Tau
Black triangles: heparin, black circles: GAGs-AD, white circles: GAGs-CT, white triangles: control.

FIG. 7B presents the effect of heparin, oligosaccharides of heparin (Arixtra) containing 3-O-sulfation and oligosaccharides of heparin lacking of 3-O-sulfation, to induce the abnormal pathological phosphorylation of recombinant human tau protein by GSK-3 Kinase. Antibody Tau396 was used to detect the abnormally phosphorylated tau formation.
x-axis: time (h)
y-axis: pmol P Tau/mol Tau
Black triangles: heparin, black diamonds: Arixtra (3Sulfated), white diamonds: Hexa-Heparine (non 3 Sulfated), white triangles: control.

FIGS. 8A to 8G present the effect of inhibiting sulfation on GAGs, including heparan sulfates, in abnormal phosphorylation in two models of SH-SY5Y differentiated cells.

Figure 8A:
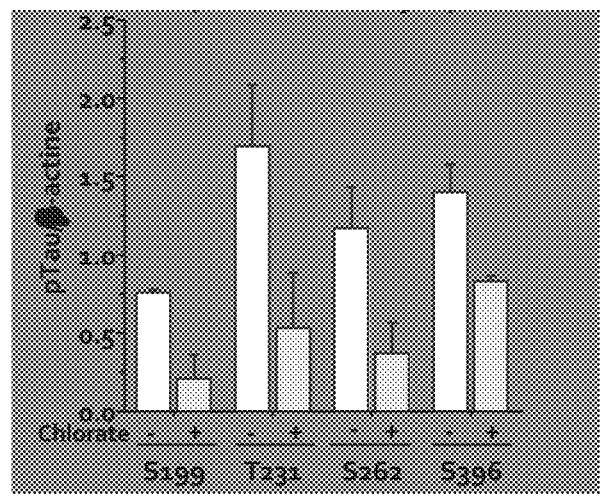
Figure 8B:
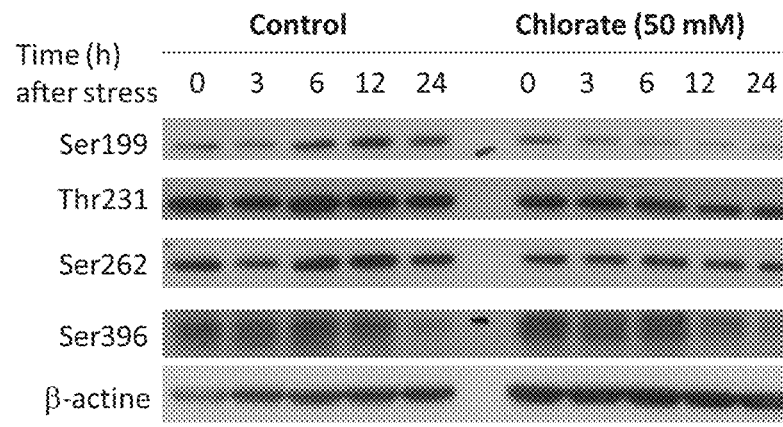

FIG. 8A presents the effect of inhibiting sulfation of GAGs in wild type differentiated SH-SY5Y cells. Sulfation is inhibited by using chlorate (50 mM), an inhibitor of 3'-phosphoadenosine 5'-phosphosulfate biosynthesis. Decreased levels of the abnormally phosphorylated Tau epitopes S199, T231, S262, and S396 after chlorate treatment were confirmed by western blot analysis.
x-axis: Tau epitope: from left to right by the anti tau199, the anti tau 231, the anti tau 262 or the anti tau396 phosphorylated epitope
y-axis: pTau/β actine FIG. 8B shows the effect of H$_2$O$_2$ (500 mM), in the presence and in the absence of chlorate treatment, on the levels of abnormally phosphorylated Tau epitopes S199, T231, S262, and S396 from 0 to 24 h, as revealed by western blot analysis.

Figure 8C:
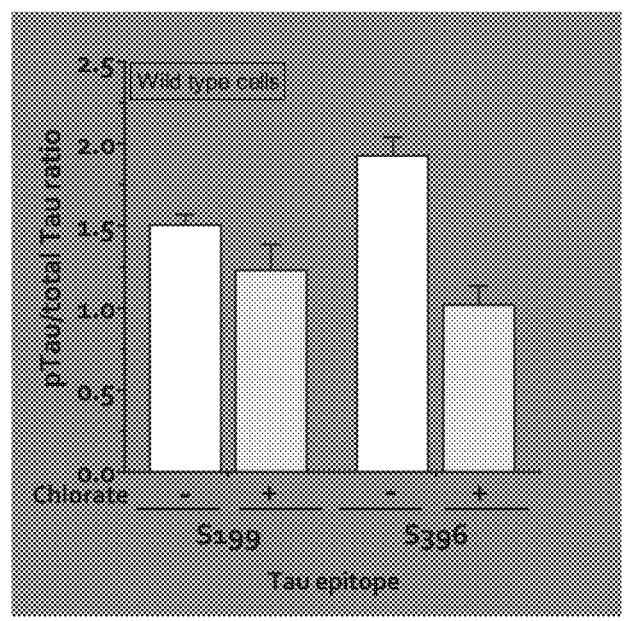
Figure 8D:
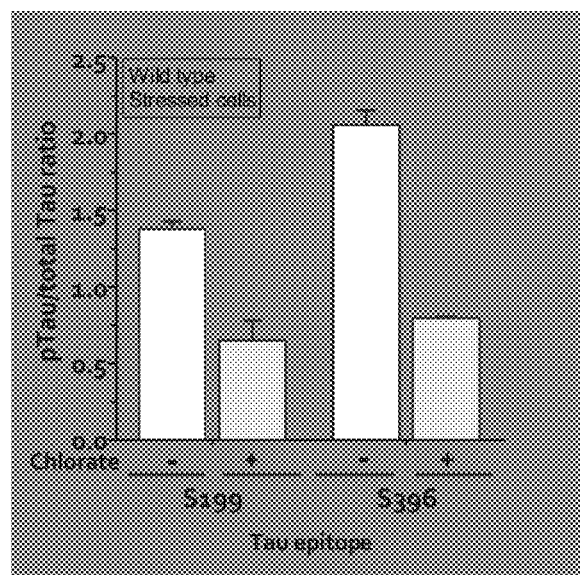
Figure 8E:
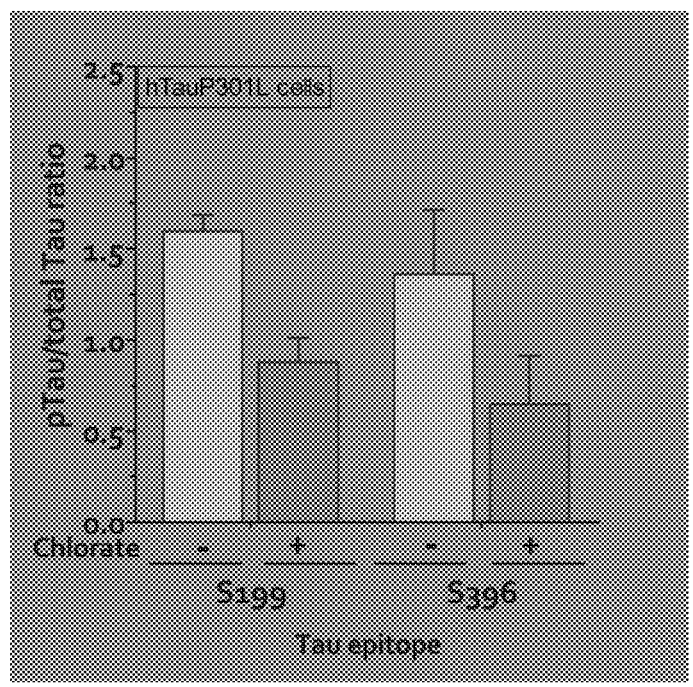
Figure 8F:
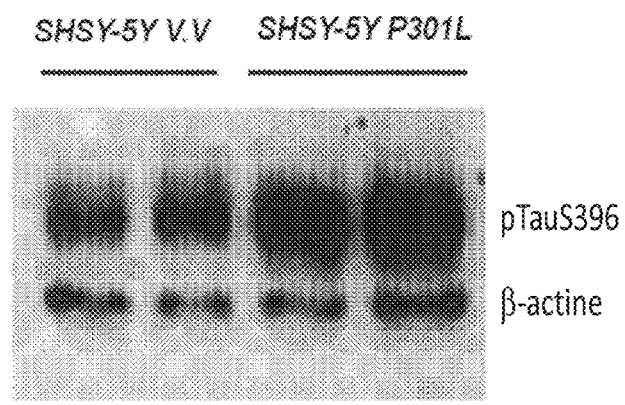

FIG. 8C shows the effect of chlorate treatment (75 mM) on the levels of abnormally phosphorylated Tau epitopes S199 and S396 on wild type cells as revealed by flow cytometry analysis.

x-axis: Tau epitope: from left to right by the anti tau199 (without and with chlorate) or the anti tau396 (without and with chlorate) phosphorylated epitope
y-axis: pTau/total-Tau FIG. 8D shows the effect of chlorate (75 mM) treatment on the levels of abnormally phosphorylated Tau epitopes S199 and S396 on wild type $H_2O_2$ (500 mM) stressed cells as revealed by flow cytometry analysis.
x-axis: Tau epitope: from left to right by the anti tau199 (without and with chlorate) or the anti tau396 (without and with chlorate) phosphorylated epitope
y-axis: pTau/total-Tau FIG. 8E shows the effect of chlorate (75 mM) treatment on the levels of abnormally phosphorylated Tau epitopes S199 and S396 on hTauP301L SH-SY5Y cells as revealed by flow cytometry analysis. hTauP301L SH-SY5Y cells are cells permanently transfected with the human Tau (hTau) in where the mutation P301L has been introduced.
x-axis: Tau epitope: from left to right by the anti tau199 (without and with chlorate) or the anti tau396 (without and with chlorate) phosphorylated epitope
y-axis: pTau/total-Tau FIG. 8F shows the effect of the introduction of the hTauP301L mutation in SH-SY5Y cells in the abnormal phosphorylation (epitope S396) of Tau.

Figure 8G:
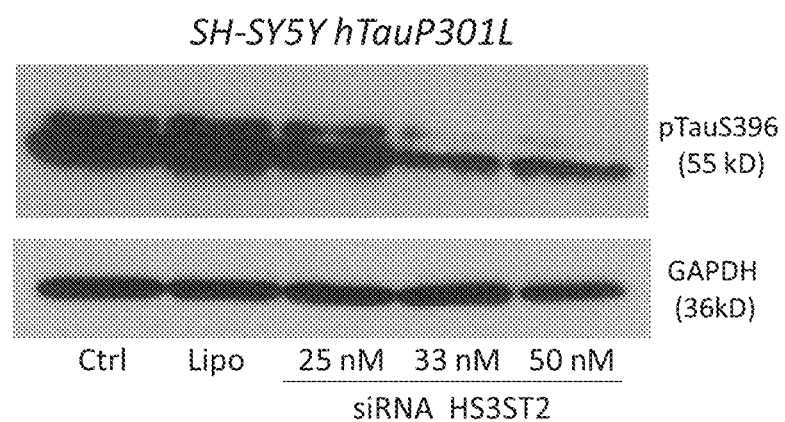

FIG. 8G shows the effect of silencing the 3-OST-2 (by siRNA set forth by SEQ ID NO 73 for the sense and 74 for the antisense) in hTauP301L SH-SY5Y cells in the abnormal phosphorylation (epitope S396) of Tau. Ctrl: control hTauP301L SH-SY5Y cells; Lipo: lipofectamine treated cells, negative siRNA control, HS3ST2 siRNA at 10, 20, 40 and 80 nM.

Figure 9:
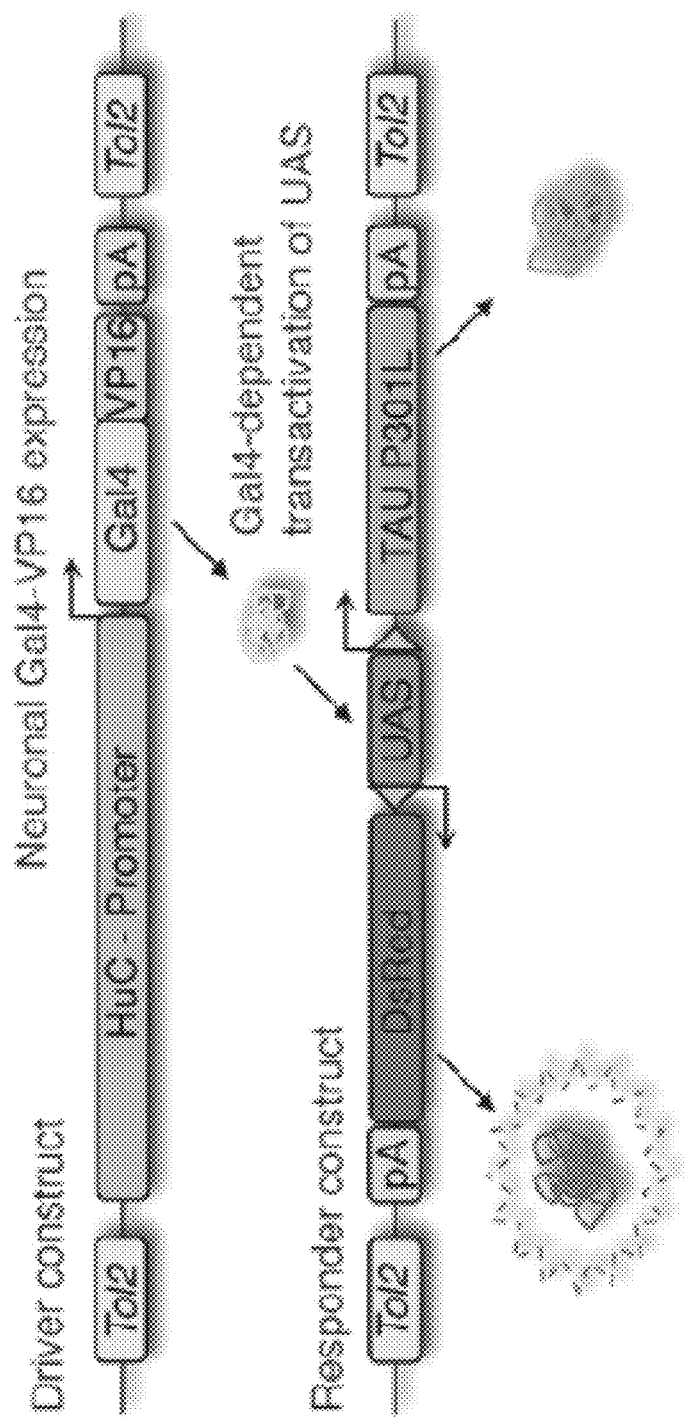

FIG. 9 presents the technical advance of transgenic zebrafish model expressing TAU-P301L.

The Driver construct contains the neuronal zebrafish promoter HuC driving the expression of Gal4-VP16, which binds to the UAS on the responder construct. It activates the bidirectional expression of hTAU-P301L and rhodamine (DsRed) via the minimal promoters. UAS-dependent gene expression of Tau and DsRed is indicated in living fish by DsRed fluorescence. Driver and Responder constructs are flanked by To12 transposon sites (FIG. 2) (Paquet et al., 2009).

Figure 10B:
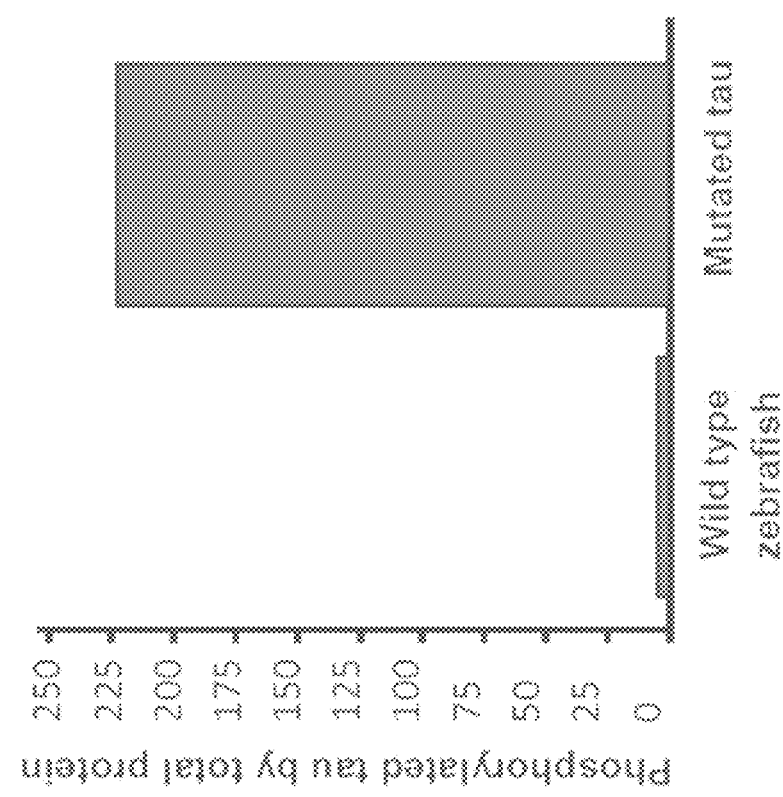
Figure 10A:
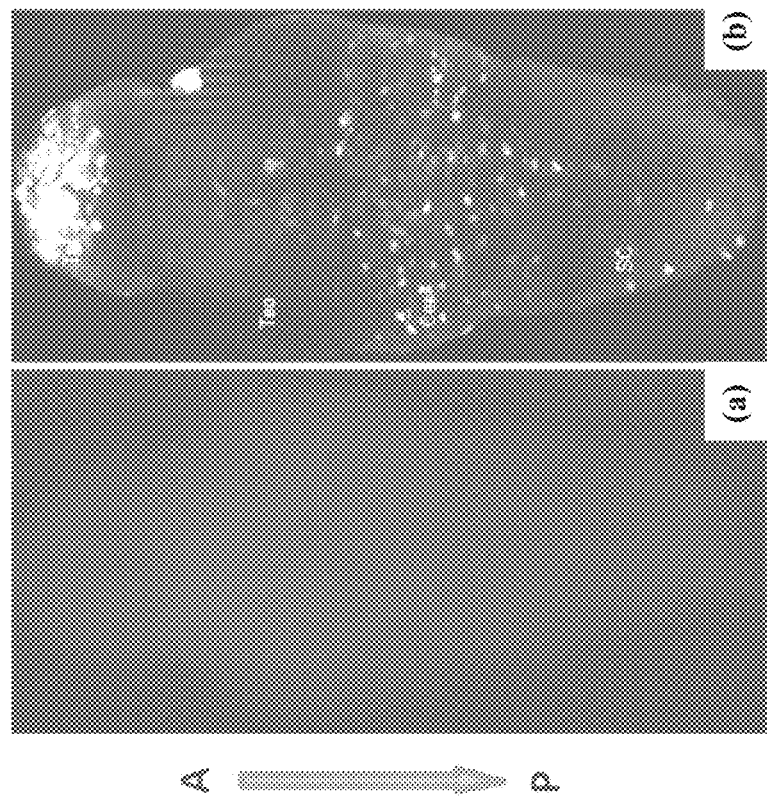

FIGS. 10A and 10B present Tau phosphorylation in hTau-P301L transgenic zebrafish.

FIG. 10A: Brains form 5 days old zebrafish embryos (wild type (a) versus hTau-P301L transgenic model (b)) were dissected and labeled with anti-Tau AT180 antibody. The marked hyperphosphorylation sites (green) are localized in the transgenic model; in the Telencephalon (Tel), Cerebellum (Cer) and upper region of the spinal cord (SC) (Abbreviations: A: Anterior, P: Posterior, TeO: Optic tectum, Cer: Cerebellum)

FIG. 10B: The level of phosphorylated protein Tau by level of total total proteins in transgenic hTAU-P301L compared to wild type nontransgenic siblings. A 90 fold increase is demonstrated in hyperphosphorylated protein Tau accumulation in transgenic hTAU-P301L compared to nontransgenic siblings.
X-axis: Phosphorylated Tau by total protein.
Y-axis: Left histogram: Wild type protein, right histogram: mutated Tau.

Figure 11:
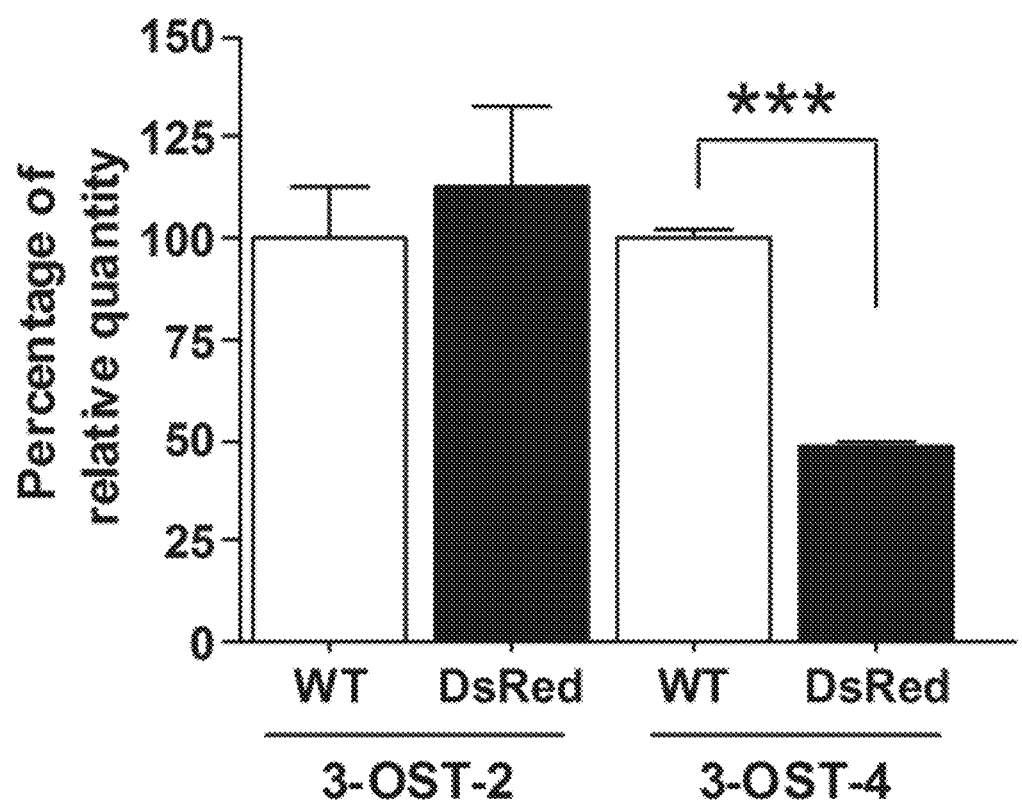

FIG. 11 presents the expression of 3-OST 2 and 4 in transgenic hTAU-P301L zebrafish.

Figure 12B:
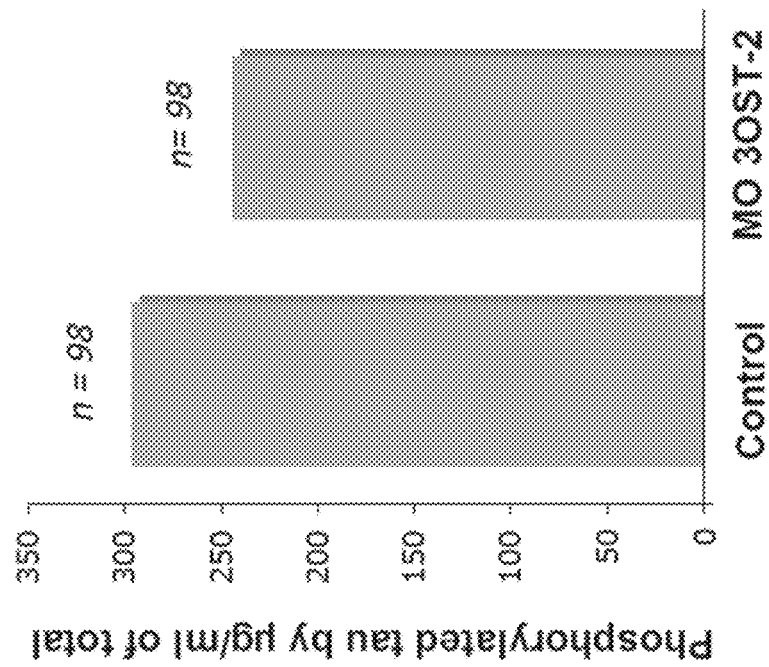

Relative quantities of 3-OST-2 and 3-OST-4 were detected by realtime PCR in the transgenic hTAU-P301L fishes (indicated with DsRed) versus WT. Enzyme expression given by WT was considered as 100%.
X-axis: percentage of relative quantity
Y-axis: from left to right:
White and black histograms of the left side (3-OST-2): White: WT; black: DsRed
White and black histograms of the right side (3-OST-4): White: WT; black: DsRed FIGS. 12A and 12B present the survival rate of 3-OST-2 morphants after 24 hours of post-injection with decreased level of phosphorylated protein.

Figure 12A:
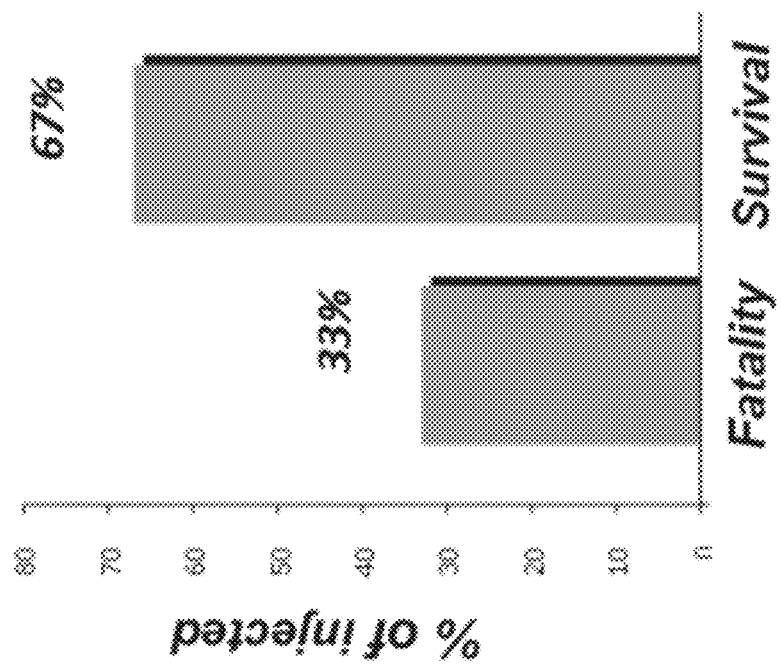

FIG. 12A: The survival rate was detected in 3-OST-2 morphans with morpholino concentration of 0.5 mM. The morpholino-mediated knock-down of the 3-OST-2 coding gene in the transgenic hTAU-P301L zebrafish embryos after 24 (hours of post fertilization) hpf was compared to the non-injected embryos used as control.
X-axis: percent of injected
Y-axis: left histogram: fatality, right histogram: survival FIG. 12B: The level of phosphorylated protein Tau by level of total protein in morphant embryos compared to non-injected controls (pool of n=98, 3 different series of injections).
X-axis: Phosphorylated Tau by µg/ml of total protein.
Y-axis: MO 3-OST-2

FIGS. 13A to 13F present the morpholino inhibition of 3-OST-2 in Zebrafish model (Paquet et al. 2009) that diminishes the accumulation of abnormally phosphorylated Tau protein in spinal cord as detected by anti-PHF-tau antibody clone AT8.

FIGS. 13A, 13C and 13E: immunostaining of Zebrafish spinal cord expressing mutated Tau protein P301L (FIG. 13A: Tau protein (DsRed), FIG. 13C: hyperphosphorylated Tau protein as detected by anti-PHF-tau antibody clone AT8, 13E: merge 13A and 13C)

FIGS. 13B, 13D and 13F immunostaining of Zebrafish spinal cord expressing mutated Tau protein P301L in which, 3-OST-2 protein has been inhibited (Morphants) (FIG. 13B: DsRed indicative of mutation present, FIG. 13D: hyperphosphorylated Tau protein as detected by anti-PHF-tau antibody clone AT8, FIG. 13F: merge 13B and 13D).

FIGS. 14A to 14F present the inhibition of 3-OST-2 in Zebrafish model (Paquet et al. 2009) that diminishes the accumulation of abnormally phosphorylated Tau protein in the brain of Zebrafish.

Figures 14A, 14C, 14E:
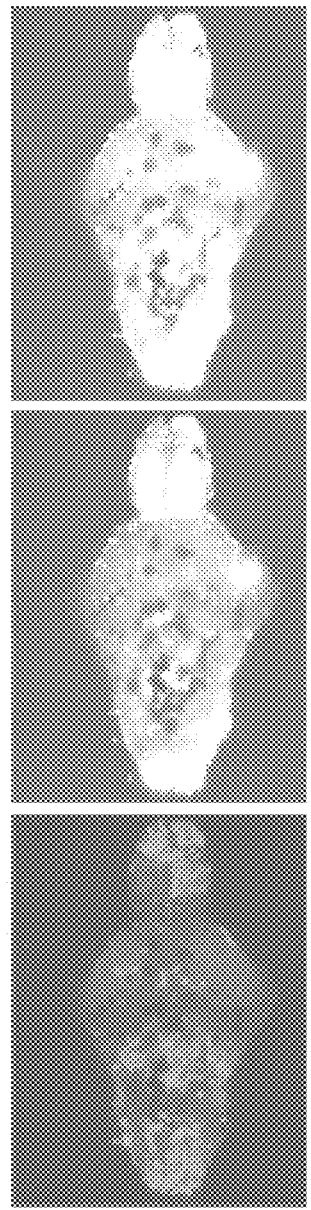

FIGS. 14A, 14C and 14E: immunostaining of Zebrafish brain expressing mutated Tau protein P301L corresponding to non injected controls (FIG. 14A: DsRed, FIG. 14C: hyperphosphorylated Tau protein as detected by anti-PHF-tau antibody clone AT8, 14E: merge 14A and 14C)

Figures 14B, 14D, 14F:
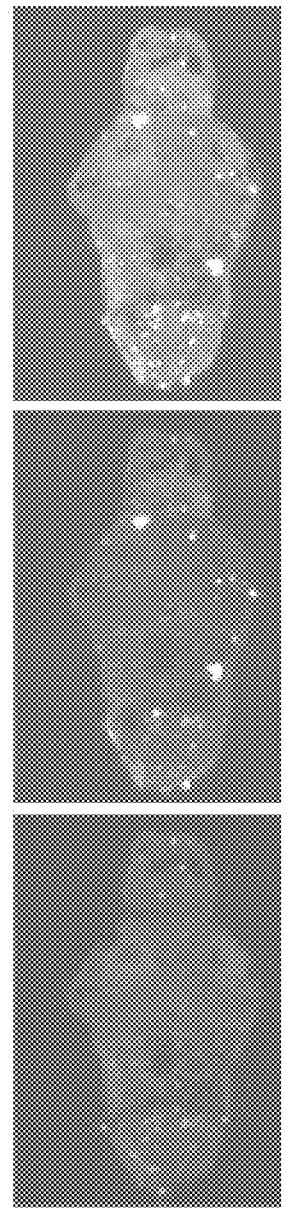

FIGS. 14B, 14D and 14F immunostaining of Zebrafish brain expressing mutated Tau protein P301L in which, 3-OST-2 protein has been inhibited (Morphants) (FIG. 14B: DsRed, FIG. 14D: hyperphosphorylated Tau protein as detected by anti-PHF-tau antibody clone AT8, 14F: merge 14B and 14D).

FIGS. 15A to 15F present the effect of 3-OST-2 expression inhibition in the abnormal phosphorylation of Tau protein and in axons recovery from the mutation effect FIGS. 15A, 15C and 15E: immunostaining of Zebrafish axon expressing mutated Tau protein P301L corresponding to non injected controls (FIG. 15A: DsRed, FIG. 15C: hyperphosphorylated Tau protein as detected by anti-pTau231, 15E: merge 15A and 15C). (10×, scale bar=50 mm).

FIGS. 15B, 15D and 15F immunostaining of Zebrafish axon expressing mutated Tau protein P301L in which, 3-OST-2 protein has been inhibited (Morphants) (FIG. 15B: DsRed indicative of mutation, FIG. 15D: hyperphosphorylated Tau protein, 15F: merge 15B and 15D).

pTau231 staining is lower and arrows show that axonal abnormalities could had been reversed in 3OST-2 splice morphants compared to DsRed/hTauP301L (10×, scale bar=50 mm).

FIGS. 16A to 16F present the effect of 3-OST-2 expression inhibition in the abnormal phosphorylation of Tau protein and in axons recovery from the mutation effect.

FIGS. 16A, 16C and 16E: immunostaining of Zebrafish axon expressing mutated Tau protein P301L corresponding to non injected controls (FIG. 16A: DsRed, FIG. 16C: hyperphosphorylated Tau protein as detected by anti-pTau231, 16E: merge 16A and 16C). (20×, scale bar=20 mm).

FIGS. 16B, 16D and 16F immunostaining of Zebrafish axon expressing mutated Tau protein P301L in which, 3-OST-2 protein has been inhibited (Morphants) (FIG. 16B: Tau protein (DsRed), FIG. 16D: hyperphosphorylated Tau protein as detected by anti-pTau231, 16F: merge 16B and 16D).

P-Tau231 staining is lower and axonal abnormalities are apparently in 3OST-2 splice morphants compared to DsRed/hTauP301L (20×, scale bar=20 mm in the first row, 50 mm in the second row)

FIGS. 17A and 17B presents the effect of the HS mimetic F6 in an accelerated senescence model of AD (SAMP8 mice). The SAMR1 mice were used as control of (control). F6 was used at high dose (H) and low dose (L) by IP 25 or 50 mg/kg or oral 100 or 200 mg/kg; twice a week for two months. Treatments started when mice were 5 month old and finished when mice where 7 months old. Hyperzine A was used as a positive control drug.

FIG. 17A: Spatial learning ability (n=10) % successful mice to reach platform
Histograms from left to right: Control, model (SAMP8), huperzine A, F6: IP 50 mg/kg, F6: IP 25 mg/kg, F6: p.o. 200 mg/kg, F6: p.o. 100 mg/kg.
FIG. 17B: Spatial Memory ability (n=10). Searching time in platform quadrant At 7 month age (2 months treatment).
Histograms from left to right: Control, model (SAMP8), huperzine A, F6: IP 50 mg/kg, F6: IP 25 mg/kg, F6: p.o. 200 mg/kg, F6: p.o. 100 mg/kg.
F6 increased spatial retention in Morris water maze after 2 months treatment (7 month aged)

Figure 18:
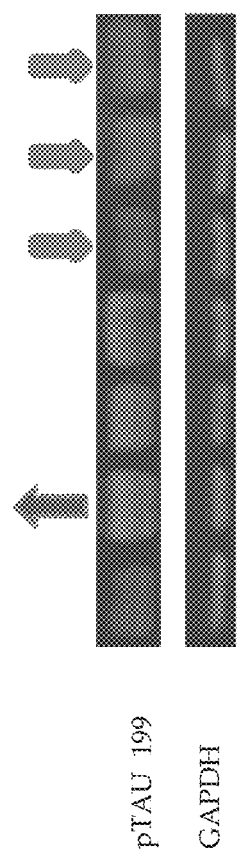

FIG. 18 presents the decrease of the hyperphosphorylated protein Tau (pTau199/202, pathological) in the brains of SAMP8 treated with sulfate heparan F6 at an IP dose of 25 or 50 mg/Kg or p.o. ar 100 or 200 mg/kg as demonstrated by western Blot analysis (WB) of brain (cortex) carried out with a specific antibody of the pathologically phosphorylated protein (pTau 199/202). The study was performed after two months treatment (7 months old mice).

upper WB: Tau199 and lower WB: GADPH
From left to right: Control, Model (SAMP8), Huperzine (anti Alzheimer control), treated SAMP with F6 25 mg/kg ip, treated SAMP with F6 50 mg/kg ip, treated SAMP with F6 100 mg/kg p.o., treated SAMP with F6 200 mg/kg p.o. for 2 months (from 5 month old to seven months old, twice a week).

The arrow in the model indicates an increase of hyperphosphorylated protein Tau compared with the control.

The arrow in the F6 treated (50 mg/kg) indicates a decrease of hyperphosphorylated protein Tau compared with the model.

FIGS. 19A to 19I present the swimming layout (Morris water maze) of SAMR1 mice (7 months old), and SAMP8 mice (7 months old) treated or not with the mimetic of sulfate heparan F6 at an IP dose of 25 mg/Kg (3 mice).

FIGS. 19A, 19D and 19G: control SAMR1 mice (control).
FIGS. 19B, 19E, 19H: model SAMP8 mice.
FIGS. 19C, 19F, 19I: model SAMP8 treated F6 mice.
Treated animals present a significant increase of memory.

Figure 20:
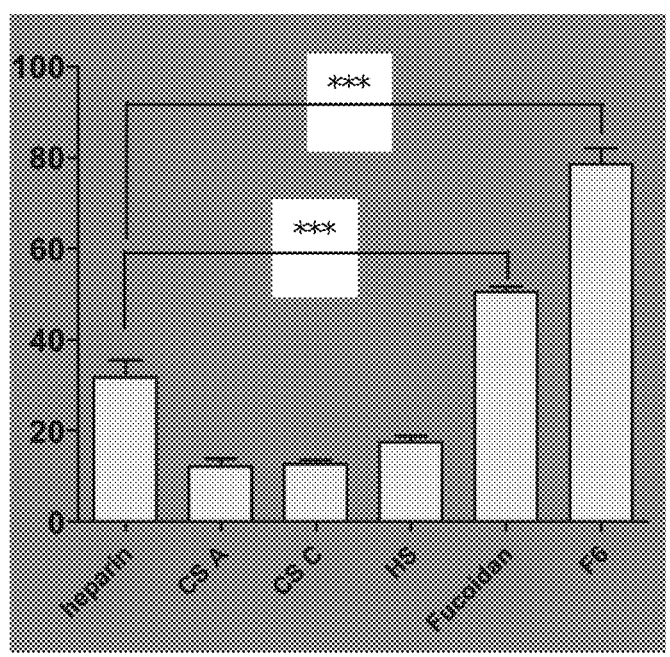

FIG. 20 presents the heparin/glycosaminoglycans competition assay towards human Tau protein.

x-axis: from left to right: heparin, chondroitin sulfate A (CSA), chondroitin sulfate C (CSC), HS, fucoidan, F6.
y-axis: percentage of binding of test compound to hTau
Fucoidan and F6 are able to compete with heparin for the binding to human Tau protein.

Figure 21:
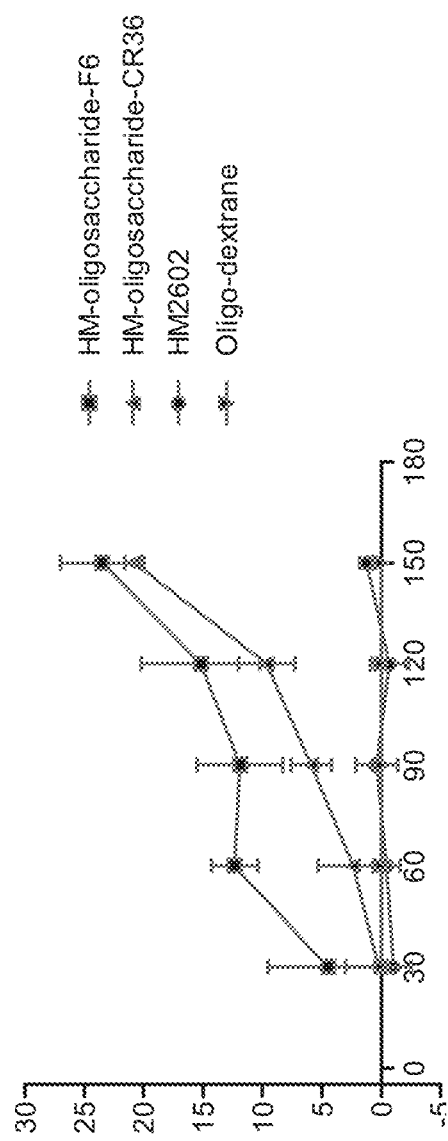
Figure 22:
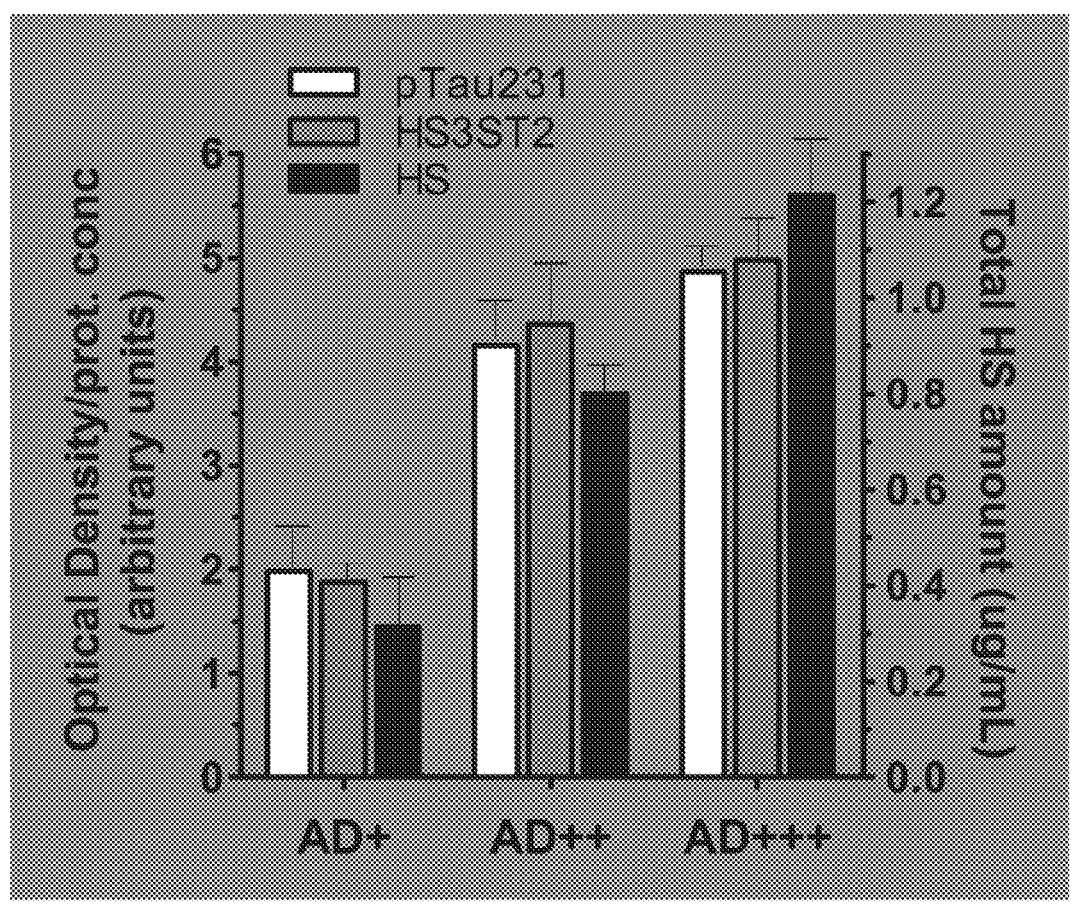

FIG. 21 presents the Blood Brain Barrier (BBB) permeability studies of F6, CR36, HM2602 and Dextran.

x-axis: time (min)
y-axis: percentage of transmembrane passage
Square: HM-oligosaccharide F6
Triangle (up): HM-oligosaccharide CR36
Diamond: HM2602
Triangle (down): oligo-dextrane FIG. 22 presents the CSF levels of pTau231 and HS3ST2, as measured by densitometry analysis of western blot gels, correlated with HS sulfate levels in CSF measured by the DMMB method.

All patients have been diagnosed with AD by clinical and biochemical evaluations with increased degree of AD (+, ++, +++). Said presented degree of AD (+,++,+++) was assumed by pTau231 levels in CSF measured by densitometry analysis of the WB.

3 samples were analyzed each time.
x-axis: from left to right: AD+, AD++ and AD+++.
For each AD degree, from left to right histograms: pTau231, HS3ST2, HS.
left y-axis: optical density/protein concentration (arbitrary units)
right y-axis: total HS amount (µg/mL)
This figure shows that the concentration of OST-2, HS and phosphorylated Tau are between is significantly increased with the degree of AD (from AD+ to AD+++).

Figure 23:
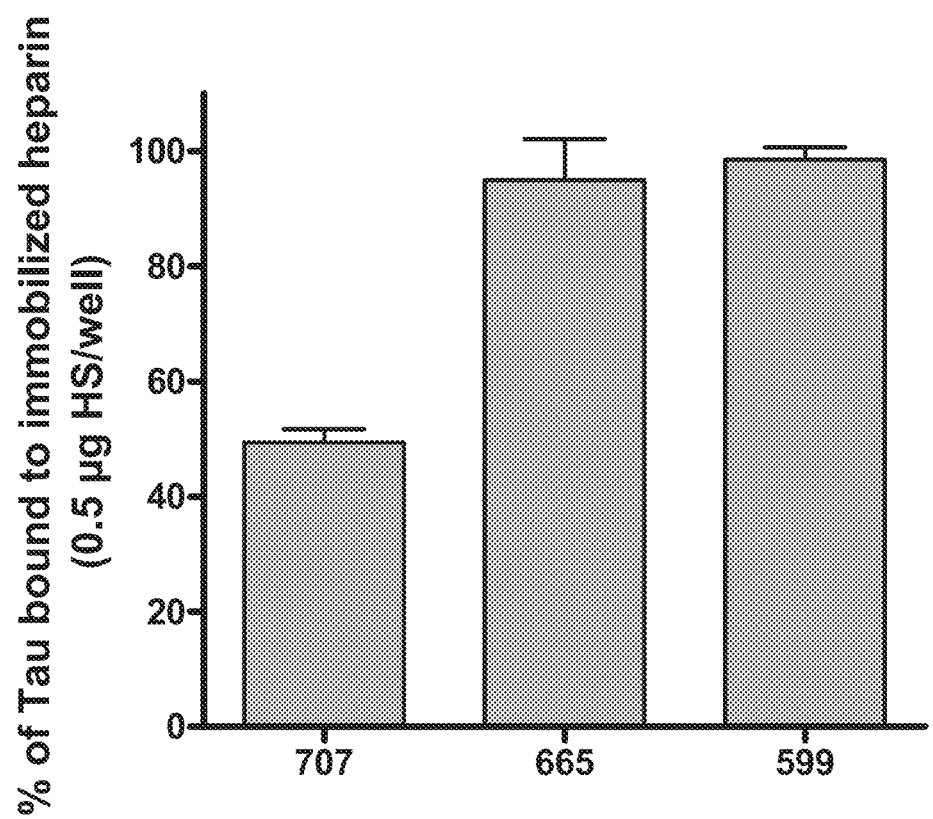

FIG. 23 presents the percentage of Tau binding to immobilized heparin in the presence of CSF (0.5 ug/well) from AD patients (same patients as in FIG. 5). HS were extracted from CSF, quantified by the DMMB method, and used for this competitive assay in where Tau protein binding to immobilized heparin (in a ELISA plate) is inhibited by HS from the CSF.

Total Tau used in the ELISA assay was commercially available.

These results show that the CSF containing the highest amount of pTau contains also the HS with the highest capacity to inhibit Tau binding to the immobilized heparin.

Each CSF sample was assayed 3 times in the binding test.

This indicates a correlation between the tauopathie and the capacity of CSF HS to bind Total Tau.

FIGS. 24A to 24H present the model of transfer inhibition of Tau aggregates from a cell (SH-SY5Y differentiated cells) to another one with F6 molecule at 0.1 and 10 µg/mL. The construct used to express Tau-EYFP in donor cells as previously reopreted: J Biol Chem. 2009 May 8; 284(19): 12845-52. Epub 2009 Mar. 11. Propagation of Tau misfolding from the outside to the inside of a cell. Frost B, Jacks R L, Diamond M I)

FIGS. 24A to 24E present the general protocol used for the study.

FIG. 24A:

Aggregates donor cells: SH-SY5Y cells are transfected with Tau-EYFP according to Frost B, Jacks R L, Diamond M I. J Biol Chem. 2009 May 8; 284(19): 12845-52. Transfected cells produce green Tau aggregates.

Recipient cells: wild type SH-SY5Y cells

FIG. 24B: Transfected cells were cultured in the upper chamber of the trans-wells. Non transfected cells were cultured in the bottom chamber of the trans-well. Both aggregates donor cells (Tau-EYF transfected cells) and recipient cells (no transfected cells) are differentiated by culturing them for 7 days in the presence of 10 μM 7 days of retinoic acid.

FIG. 24C: Both aggregates donor cells (transfected cells) and recipient cells (no transfected cells) are submitted to an oxidative stress pulse ($H_2O_2$, 500 μM) for 30 min. After this time, the stressor containing medium was replaced by fresh medium containing or not the F6 molecule.

FIG. 24D: Aggregates donor cells and recipient cells are co-cultured 24 hours.

FIG. 24E: Recipient cells are fixed, labeled with bIII-tubulin (red) and examined by microscopy.

Cells were fixed and labeled A) Stressed cells untreated by the drug. B) Stressed cells treated with F6 (10 μg/mL). C) Tau aggregates were counted in 10 different fields and in 3 different cultures for each condition.

Figure 24F:
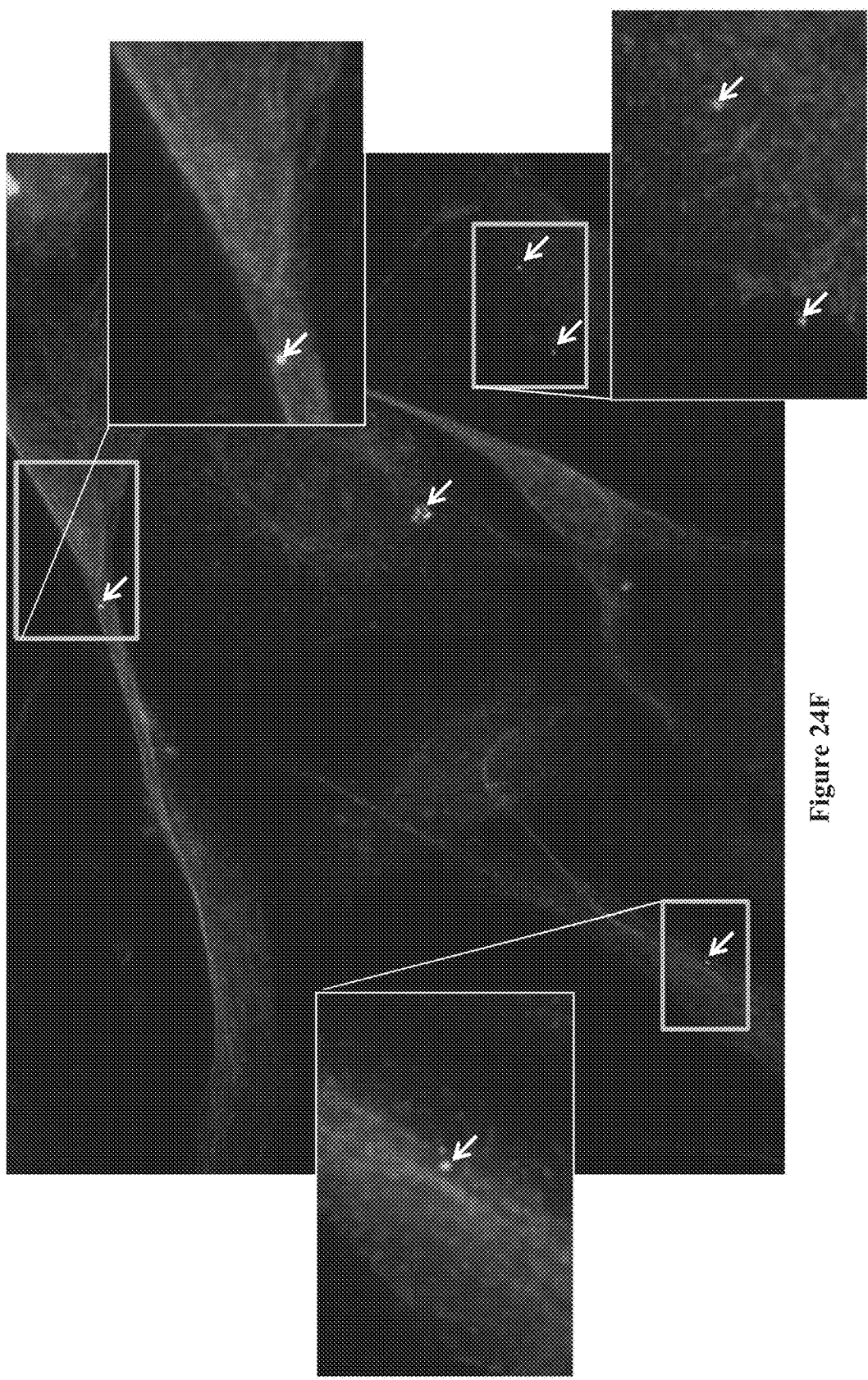

FIG. 24F: Stressed recipient SH-SY5Y cells not treated by F6 and co-incubated (co-cultured) with stressed SH-SY5Y/Tau-EYFP show to be infected by green Tau aggregates from stressed donor cells (white arrows).

Figure 24G:

FIG. 24G: Stressed recipient SH-SY5Y cells co-incubated with stressed SH-SY5Y/Tau-EYFP treated with F6 molecule (10 μg/mL). Tau aggregates (white arrow) were counted in 10 different fields and in 3 different cultures for each condition.

Figure 24H:
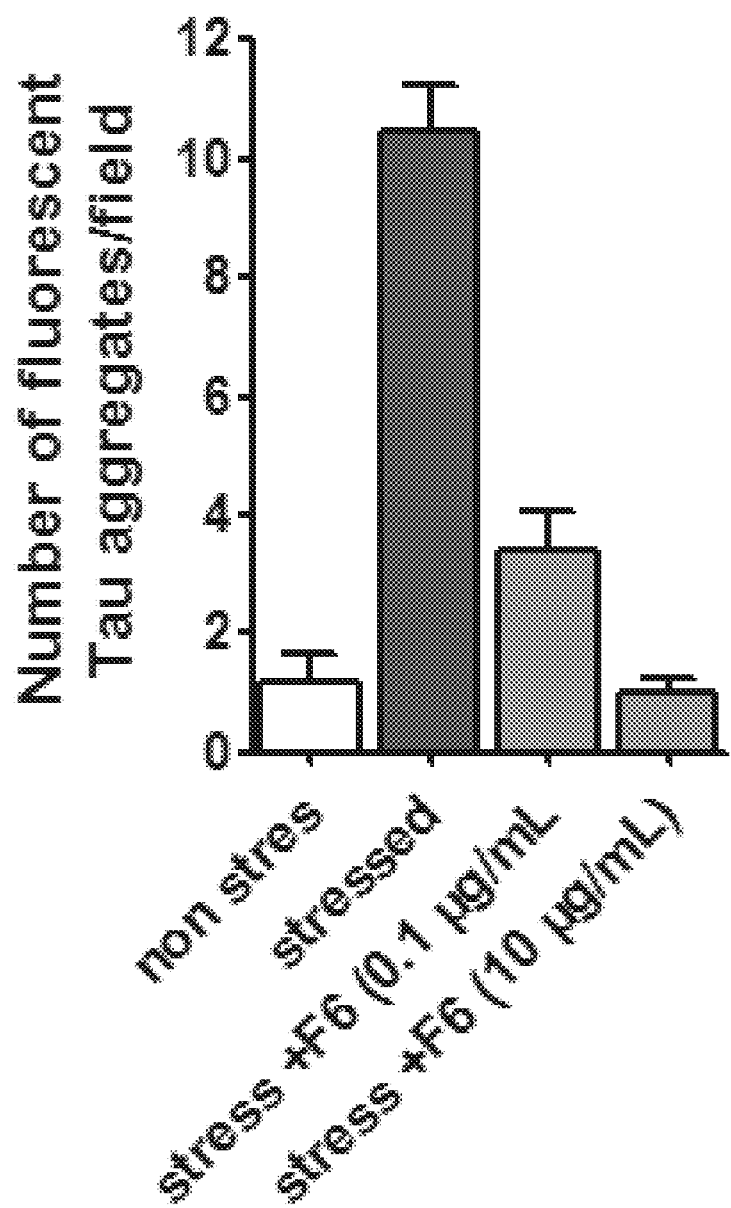

FIG. 24H: Number of fluorescent Tau aggregates per field in function of the treatment.

x-Axis: from left to right: non stressed, stressed, stressed+ F6 (0.1 μg/mL), and stressed+F6 (10 μg/mL).

y-axis: Number of fluorescent Tau aggregates per field.

F6 molecule markedly decreases the number of fluorescent Tau aggregates.

FIGS. 24A to 24H show that F6 molecule inhibits the transfer of Tau aggregates from a cell (SH-SY5Y differentiated cells) to another one, and thus polysaccharides such as heparan sulfate mimetics, in particular F6 molecule are liable to treat Tauopathies, in particular Alzheimer's disease.

Figure 25:
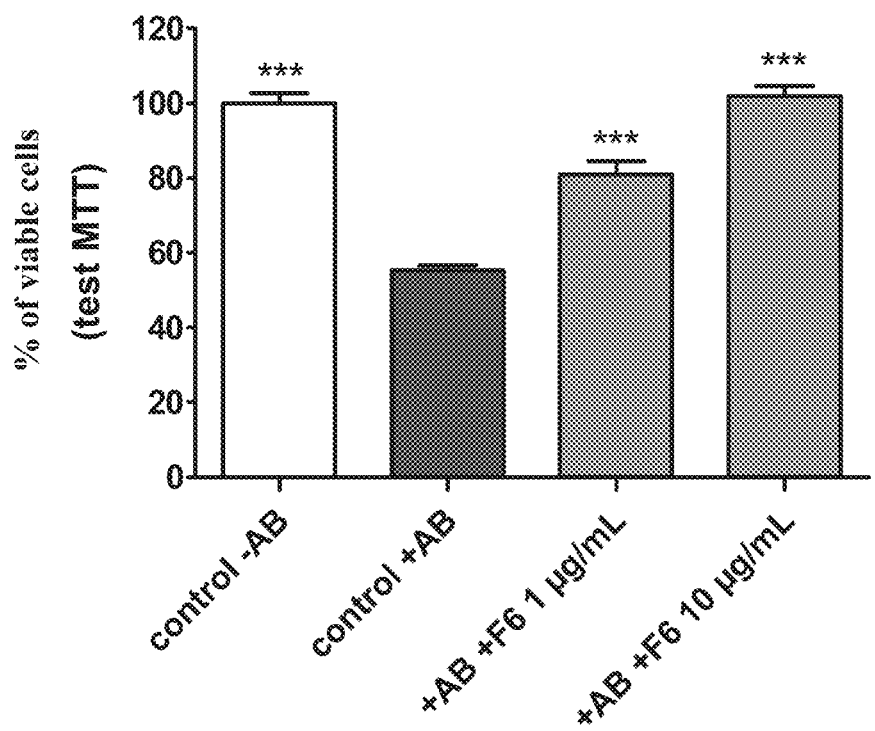

FIG. 25 presents the protective effect of heparan sulfate mimetic F6 in SH-SY5Y cells differentiated with retinoic acid and treated with the peptide Abeta25-35 (25 μM).

x-axis: from left to right: control without Aβ, control with Aβ, Aβ+F6 (1 μg/mL), Aβ+F6 (10 μg/mL);

y-axis: % of viable cells as determined by a MTT test

A p value <0.05 was considered to be statistically significant

Note that *≤0.05, ≤0.01 and *≤0.001.

Figure 26:
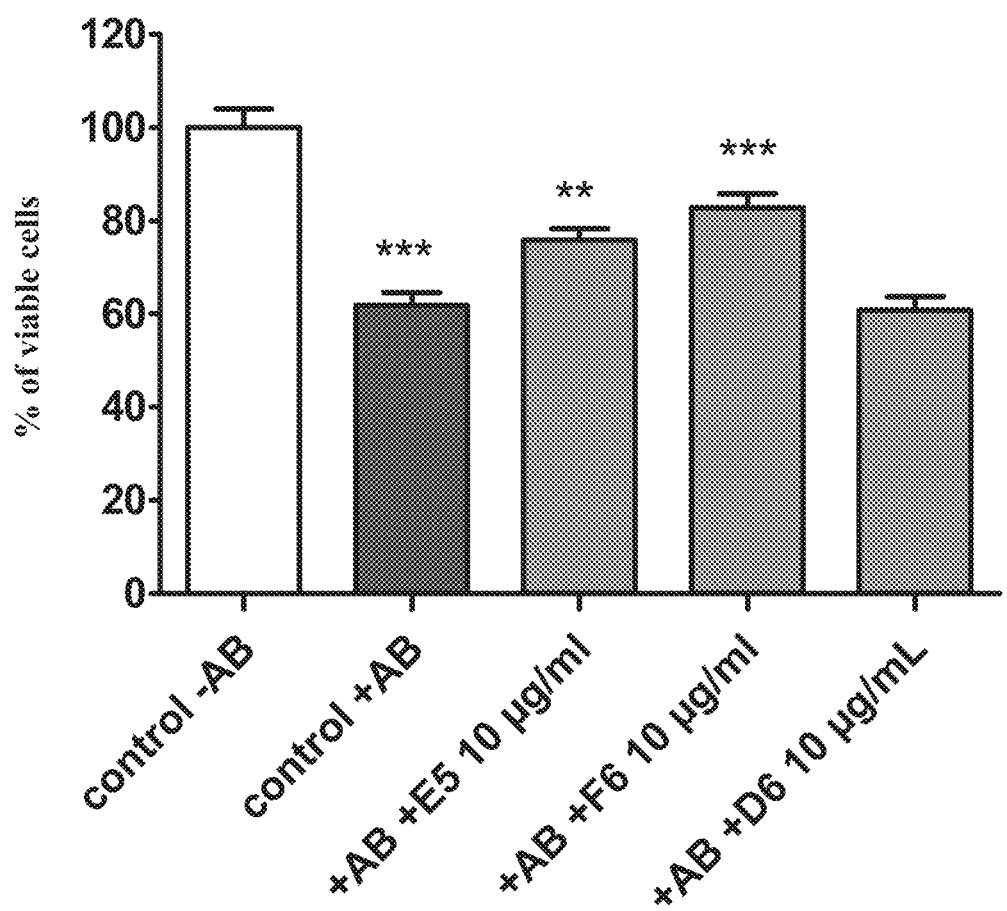

FIG. 26 presents the effect of various heparan sulfate mimetics on the survival of SH-SY5Y differentiated cells treated with peptide Aβ42.

x-axis: from left to right: control without Aβ, control with Aβ, Aβ+E5 (10 μg/mL); Aβ+F6 (10 μg/mL); Aβ+D6 (10 μg/mL);

y-axis: % of viable cells as determined by a MTT test

Columns are compared to control+Aβ: p value <0.05 was considered to be statistically significant Note that *≤0.05, ≤0.01 and *≤0.001.

Figure 27:
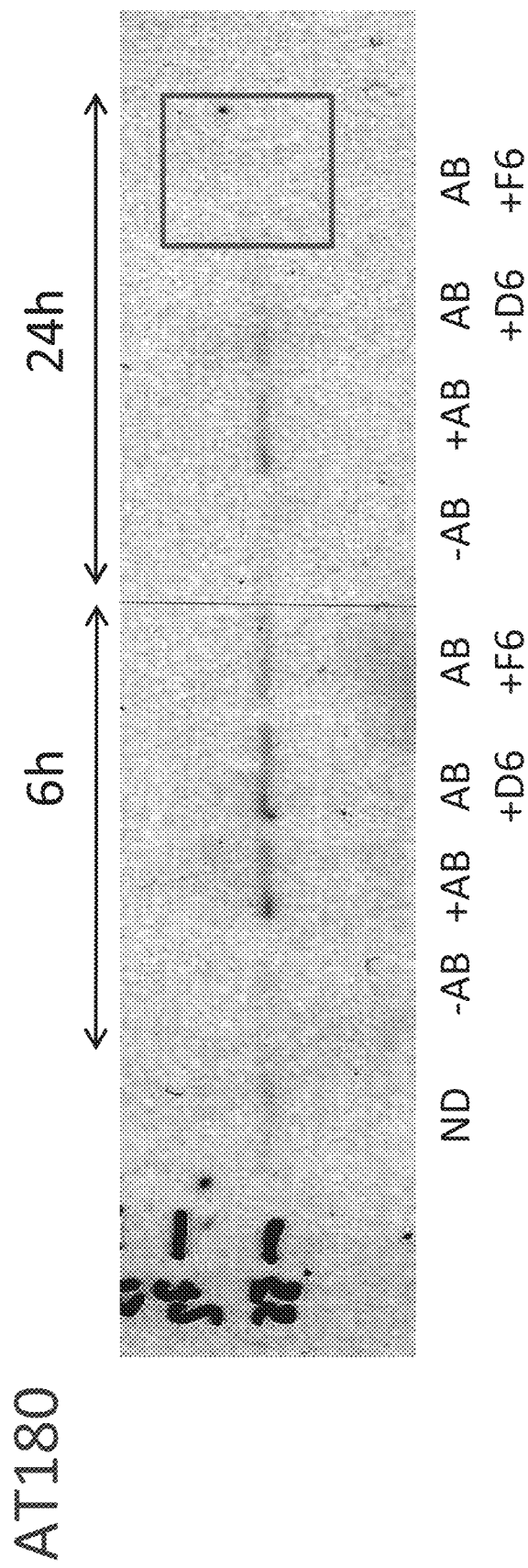

FIG. 27 presents the Tau phosphorylation in cells protein extracts after 6 h or 24 h of treatment with Aβ25-35. Effect of heparan mimetics D6 and F6 (10 μg/mL) as detected by AT 180.

Heparan sulfate mimetics decrease phosphorylated Tau.

Figure 28A:
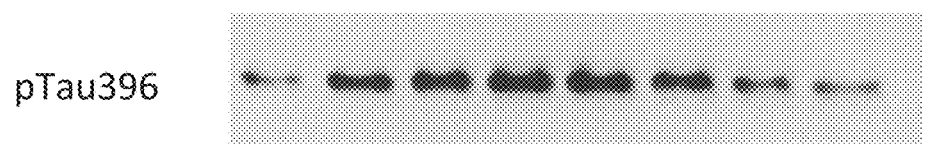
Figure 28B:
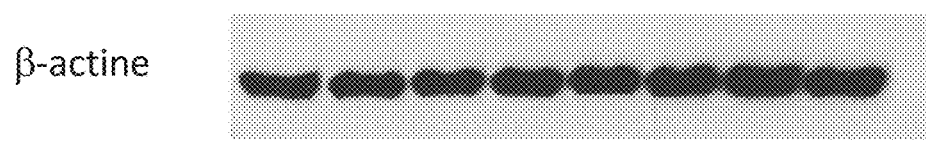
Figure 28C:
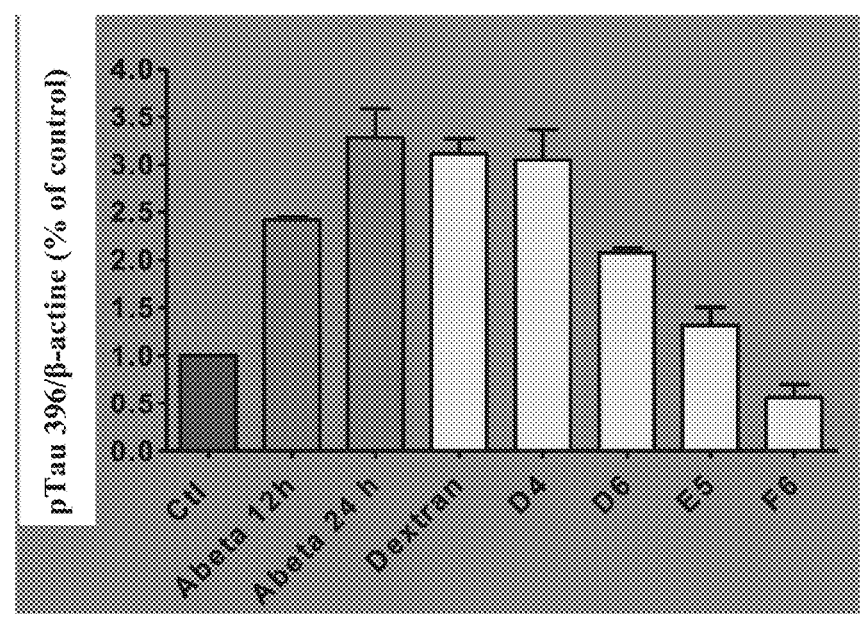

FIG. 28A to 28C present the Tau phosphorylation in Aβ42 stressed cells treated with heparan sulfate mimetics Dx, D4, D5, D6, F6 at 10 μg/mL.

FIG. 28A: pTau 396

FIG. 28B: β actine

FIG. 28C: pTau 396/β actine in function of various compounds.

x-axis: from left to right: control, Aβ 12 h, Aβ 24 h, dextran, D4, D6, E5, F6.

y-axis: pTau 396/β-actine (% of control)

Statistics are done with the average signal from two WB

Heparan sulfate mimetics decrease phosphorylated Tau.

Figure 29:
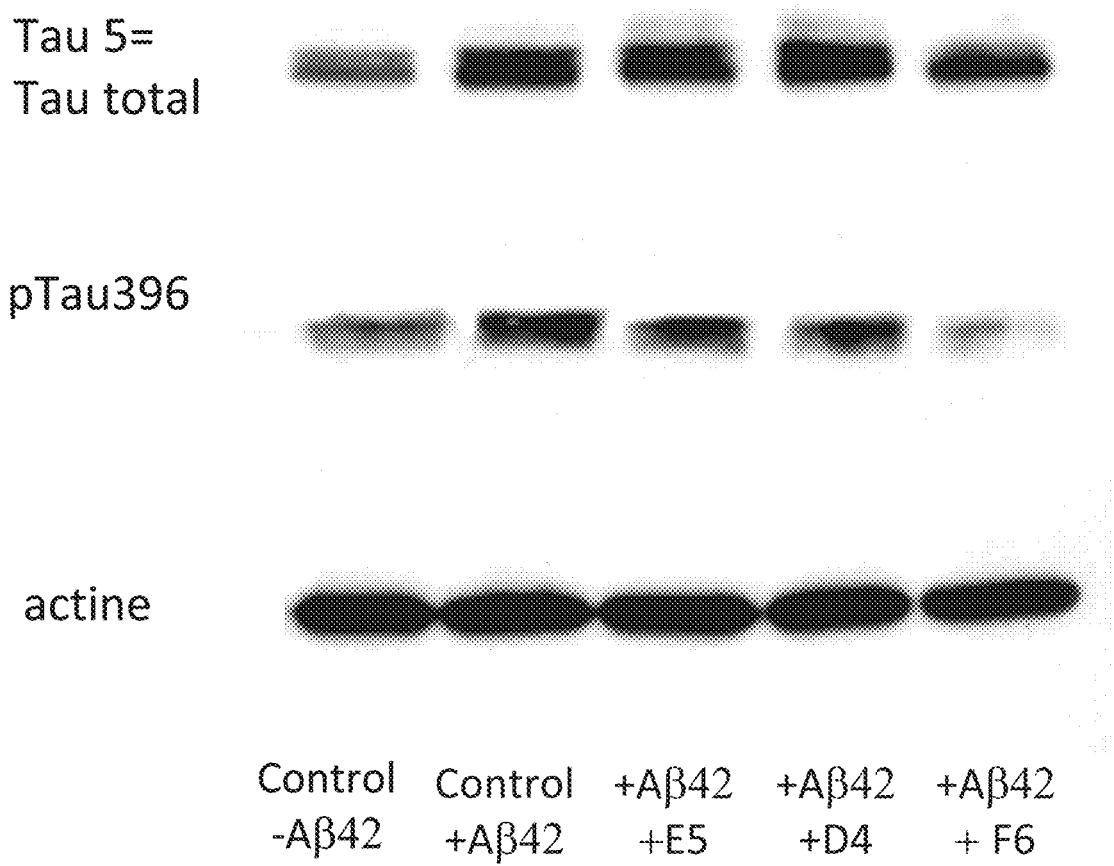

FIG. 29 presents the Tau phosphorylation in Aβ42 stressed cells treated with heparan sulfate mimetics D4, E5 and F6 at 10 μg/mL for 24 h.

Heparan sulfate mimetics such as D4, E5 and F6 decrease phosphorylated Tau.

EXAMPLES

Example 1

Brain Tissue Dissection from Control and AD Human Brain Tissue

Post-mortem human brain sampling was performed according to the Consortium to Establish a Registry of AD (CERAD). Two experimental groups were included in the study, an aged group (n=8, control group) with subject ages ranging from 60 to 77 years with a mean of 67.8±2.9 years, and an AD group (n=8) with subjects ages ranging from 69 to 82 years with a mean of 76.8±3.5 years. Subjects included in the study received post-mortem evaluation by a board-certified neuropathologist. Post-mortem intervals varied from 8.0 h to 15.2 h for both groups. No significant statistical difference (p=0.1781) was found for post-mortem delay between the two groups. Brains were obtained at autopsy and halved sagitally within 2 h after autopsy. One hemisphere was cut into 2-cm-thick slabs along the frontal plane from which the hippocampus (temporal lobe), cortex, and cerebellum were dissected. Tissues were immediately frozen after dissection in dry ice. Tissue samples were stored at −80° C. until use.

Example 2

Senile Plaques and Neurofibrillary Tangles (NFT) Quantification in Control and AD Human Brain Tissue Neuropathologic changes in brains were investigated using Consortium to Establish a Registry for Alzheimer's Disease (CERAD) and Braak and Braak guidelines. Senile plaques and NFT were determined on Bielschowsky—stained sections of middle frontal gyrus, middle temporal gyms, inferior parietal lobule, occipital pole, hippocampal CA1 and enthorinal cortex. Senile plaques were counted using a 10× objective and NFT were counted with a 20× objective. An arithmetic mean was calculated (Mean±SEM) from the counts of six fields for senile plaques/mm$^2$ and NFT/mm$^2$ for each region. Neuropathologic diagnosis was then made using the guidelines proposed by CERAD and Braak and Braak criteria. AD brains were characterized to be at stage III-V from hippocampal analysis. Control brains were determined to be non AD.

Example 3

Immunohistochemical HS and Tau Co-Localization on Human Hippocampus

Sections (20 µm) of human hippocampus from Alzheimer and age-matched control were fixed with 3% acetic acid for 10 min at room temperature (rt). Sections were then incubated for 30 min with 3% BSA dissolved in phosphate-buffered saline (PBS) and permeabilized with 0.2% Triton X100 in PBS for 30 min. HS were stained with an anti-heparan sulfate (10E4 epitope, Seikagaku corp. by AMS Biotechnology) and anti-Tau phosphoSerine 262 (Millipore); dissolved in permeabilization buffer (1:200) and incubated for 1 h 30 min at rt. Fluorescence was introduced by staining tissue slides with a secondary antibody conjugated to an Alexa 568 fluoroprobe (Molecular Probes) and Alexa 488 fluoroprobe (Interchim). Then, sections were DAPI labelled for 3 min with a 1 µg/mL DAPI solution and rinsed with methanol. Images were first obtained using a CCD monochrome camera (CFW-1310M, Scion Corporation, USA) fitted to a BH-2 epi-fluorescence optical microscope (Olympus). Image acquisition was obtained from the Scion VisiCapture 2.0 software. Image processing was done using ImageJ software (W. Rasband, National Institute of Mental Health, Maryland, USA). DAPI labelling of nuclei was quantified as the previously described (Blondet et al., 2006).

Example 4

Expression of 3-OST Enzymes in Alzheimer's Disease Hippocampus

Here, it has been investigated if the expression 3-OST enzymes involved in HS biosynthesis were altered in Alzheimer's disease compared to control hippocampus samples (Table 2). Results show a particular over-expression of the 3-OST-2 and 3-OST-4 in the Alzheimer's disease hippocampus. This may suggest the enhanced of 3-O-sulfation in the HS chains of Alzheimer's disease brains and enhanced expression of 3-OST-2 transcripts can be thought characteristic of the disease. As control experiments, expected expression of glutamine synthetase (GS) and of glyceraldehyde-3-phosphate deshydrogenase (GAPDH), known to be enhanced in Alzheimer's disease brains (Burbaeva et al., 2005), were confirmed, as well the unchanged expression of the chemokine receptor 4 reported to keep stable in Alzheimer's disease compared to age-matched individuals (Cartier et al., 2005). Our results agreeing these expected increases of genes expressions (Table 2) indicate that, as shown by the RIN number, the quality of the biological material was consistent for these studies.

TABLE 2

Expression of human 3-OST enzymes by real time PCR

| Target | Enzymes | Relative quantity control (µg/mL) | Relative quantity Alzheimer's disease (µg/mL) | Expression Alzheimer's disease vs Control |
|---|---|---|---|---|
| Heparan sulfate | 3-OST-1 | 0.75 ± 0.09 | 0.96 ± 0.20 | NS |
| | 3-OST-2 | 0.37 ± 0.07 | 2.06 ± 0.46 | ↑** |
| | 3-OST-3a | 0.35 ± 0.08 | 2.17 ± 0.86 | ↑* |
| | 3-OST-3b | 0.58 ± 0.21 | 1.76 ± 0.43 | ↑* |
| | 3-OST-4 | 1.33 ± 0.12 | 5.04 ± 0.31 | ↑*** |
| | 3-OST-5 | 0.10 ± 0.01 | 0.08 ± 0.02 | NS |
| | 3-OST-6 | — | — | ND |

NS: no significant change in enzyme expression
ND: the enzyme was not detected

RNA Extraction and RTqPCR from Control and AD Human Brain Tissue:

Total RNA was extracted from human hippocampus. For quantitative PCR (qPCR), primers (Eurofins, Germany) were designed by Primer3output. qPCR was performed from template cDNA according to the LightCycler FastS art DNA Master SYBR Green kit manufacturer's instructions (Roche, Germany). qPCR conditions were depended on primer set (Table 3). Samples were simultaneously amplified in single runs. Relative quantification of gene expression was performed using the comparative CT method, also referred to as the ααCT method (Schefe et al., 2006). Two reference genes (α-tubulin and TFIID) were used as endogenous controls. Normalization of these genes was accomplished with the Genorm program (Vandesompele et al., 2002).

TABLE 3

Oligonucleotides for real time qPCR in human hippocampus

| Gene name | Accession number | Oligonucleotide sequences (sense) | Oligonucleotide sequences (anti-sense) |
|---|---|---|---|
| NDST-1 | NM_001543 | GGAAGTGTGTCCGTGGTTC (SEQ ID NO: 11) | CCCTGGTAACTGTGCTCCAT (SEQ ID NO: 12) |
| NDST-2 | NM_003635.3 | CTCCAGTTGTGGAAGGTGGT (SEQ ID NO: 13) | CTTAGGGCTGGTGGACACAT (SEQ ID NO: 14) |
| NDST-3 | NM_004784 | CGACCTCCAACACCTACCAT (SEQ ID NO: 15) | TAGGACTGTGGGGTCTGTCC (SEQ ID NO: 16) |
| NDST-4 | NM_022569 | GCAACGGTGATTCAGGATCT (SEQ ID NO: 17) | TGTGCAGCCAAAAGTTCAAG (SEQ ID NO: 18) |

TABLE 3-continued

Oligonucleotides for real time qPCR in human hippocampus

| Gene name | Accession number | Oligonucleotide sequences (sense) | Oligonucleotide sequences (anti-sense) |
|---|---|---|---|
| GLCE | NM_015554 | GGAAGTGTGTCCGTGGTTCT (SEQ ID NO: 19) | CCCTGGTAACTGTGCTCCAT (SEQ ID NO: 20) |
| HS2STVar1 | NM_012262 | CGAAGTCCGAGAAATTGAGC (SEQ ID NO: 21) | AATGAAGTGCTTGCCGTTTT (SEQ ID NO: 22) |
| HS2STVar2 | NM_001134492 | CGAAGTCCGAGAAATTGAGC (SEQ ID NO: 23) | AATGAAGTGCTTGCCGTTTT (SEQ ID NO: 24) |
| HS6ST1 | NM_004807 | GGCCCTTCATGCAGTACAAT (SEQ ID NO: 25) | TACAGCTGCATGTCCAGGTC (SEQ ID NO: 26) |
| HS6ST2VarL | NM_001077188 | CGGGGTTCTCCAAACACTAA (SEQ ID NO: 27) | GTCTCGGAGGATGGTGATGT (SEQ ID NO: 28) |
| HS6ST2VarS | NM_147175 | AGGCTCCTTCAGACCCATTT (SEQ ID NO: 29) | TCGGATTTGGGTTCTGACTC (SEQ ID NO: 30) |
| HS6ST3 | NM_153456 | CATCTCCCCCTTCACACAGT (SEQ ID NO: 31) | CTCGTAAAGCTGCATGTCCA (SEQ ID NO: 32) |
| HS3ST1 | NM_005114 | ACCACATGCAGAAGCACAAG (SEQ ID NO: 33) | TTGAGGGCCTTGTAGTCCAC (SEQ ID NO: 34) |
| HS3ST2 | NM_006043 | GGAACCCCACTTCTTTGACA (SEQ ID NO: 7) | GTCGAGGAGCCTCTTGAGTG (SEQ ID NO: 8) |
| HS3ST3A1 | NM_006042 | ACGCCCAGTTACTTCGTCAC (SEQ ID NO: 35) | GAACGTCAAGCTCTCGAAGG (SEQ ID NO: 36) |
| HS3ST3B1 | NM_006041 | ACGCCCAGTTACTTCGTCAC (SEQ ID NO: 37) | TCTGCGTGTAGTCCGAGATG (SEQ ID NO: 38) |
| HS3ST4 | NM_006040 | AAGAGCAAAGGTCGGACTCA (SEQ ID NO: 9) | ACCCTCTTCCTGTTCCCACT (SEQ ID NO: 10) |
| HS3ST5 | NM_153612.3 | GCTAGAGGGGAAGGAGAGGA (SEQ ID NO: 39) | CCATCGACGACATGAAATTG (SEQ ID NO: 40) |
| HS3ST6 | NM_001009606.2 | CTGTCCCACTTCCTGTTCGT (SEQ ID NO: 41) | CCTTGGTGGCGTTGAAGTAG (SEQ ID NO: 42) |
| TUBA1A | NM_006009.2 | GCAACAACCTCTCCTCTTCG (SEQ ID NO: 43) | GAATCATCTCCTCCCCCAAT (SEQ ID NO: 44) |
| TBP (TFIID) | NM_003194.4 | TGCACAGGAGCCAAGAGTGAA (SEQ ID NO: 45) | CACATCACAGCTCCCCACCA (SEQ ID NO: 46) |

Example 5

AD Patients for Cerebrospinal Fluid:

Cerebrospinal fluid (CSF) samples were obtained by lumbar puncture from patients with clinical features of AD. Patients and samples were previously described by Sarazin et al. (Habert et al. Brain perfusion SPECT correlates with CSF biomarkers in Alzheimer's disease. Eur J Nucl Med Mol Imaging 2010; 37:589-593). Patients with AD fulfilled the National Institute of Neurological and Communicative Disorders and Stroke and the Alzheimer's Disease and Related Disorders Association (NINCDSADRDA) criteria for probable AD. All subjects underwent the same clinical, biochemical (CSF biomarker measurements), and neuroimaging procedures. All patients had a routine MRI exploration, including fluid-attenuated inversion recovery (FLAIR), T1- and T2-weighted sequences. They did not show clinical or neuroimaging evidence of focal lesions and no cortical or subcortical vascular lesions. AD patients could display various degrees of cortical and/or subcortical atrophy. They had no medical conditions that would interfere with cognitive performance and no severe depression. All patients were treated with acetylcholine esterase inhibitors from the time of diagnosis. They were living in the community.

CSF Examination

CSF samples obtained by lumbar puncture were centrifuged for 10 min at 1,500 rpm at 4° C. to remove cells, aliquotted into 0.4-ml polypropylene tubes and stored at −80° C. until analysis.

Preparation of Tissue and CSF Protein Extracts for Phosphor-Tau and HS3ST-2 by Western Blotting Frozen brain tissues were homogenized under liquid nitrogen vapors and the suspended in a Laemmli buffer 4× (1:100 β-mercaptoethanol added previously). The mixture was boiled for 5 min and sonicated 5 min. Tubes were then centrifuged 10 min (1,500 rpm at 4° C.). Protein concentrations in tissue homogenates and CSF samples were calculated by using Pierce® BCA Protein Assay kit, following manufacturer's instructions and equal amounts of samples were electrophoresed on 10% gels (Invitrogen Corp). After transfer, membranes were blocked with blocking buffer (3% milk in PBS, 0.02% Tween-20) for 40 min and probed with an goat anti-HS3ST2 (T-15, Santa Cruz) 2 hours at room temperature). Membranes were rinsed once in PBST and then washed 3 times for 5 min in same buffer. Secondary antibody was diluted in PBST and incubated 45 min at RT (rabbit anti-goat, Jackson Immuno Research). Membranes were rinsed with PBST and washed 3 times for 5 min in the same buffer. Blots were developed with Immobilon Western Chemiluminiscent HRP Substrate (Millipore) following manufacturer's instructions.

After, the membrane was washed in TBS 1× and then incubated for 2 hours at room temperature with anti-pTau Thr231 (rabbit polyclonal, Millipore, ref 9668, lot NG1863963) diluted in 1% BSA in TBS, 0.1% Tween-20 (TBST). Membranes were washed 3 times in TBST for 5 minutes and then incubated with the secondary antibody (donkey anti-rabbit Jackson ImmunoResearch). Blots were developed with the same reagent.

Glycosaminoglycans (Heparan Sulfates and Chondroitin Sulfate) Extraction and Quantification from Brain and CSF GAGs were extracted from brain tissue and CSF as follows: Frozen brain tissue samples were reduced to powder, homogenized and suspended in an extraction buffer (50 mM Tris, pH 7.9, 10 mM NaCl, 3 mM $MgCl_2$ and 1% of Triton X-100) to final 25 mg of tissue per mL of buffer. CSF or brain homogenates were treated by proteinase K (PK) (Merck) (final 50 μg/mL of sample) at 56° C. overnight followed by 30 min at 90° C. to inactivate the enzyme. After cooling to room temperature (rt), DNase I (Qiagen) was added (7.5 mU/mL of sample) and samples were incubated overnight at 37° C. Samples were then diluted 1:1 with 4 M NaCl, centrifuged (13 000 g, 20 min) and pellet was discarded. Lipids were eliminated by 1:1 chloroform extraction and total sulfated GAGs were quantified according to the 1-9 dimethyl-methylene blue (DMMB) assay as described (Huynh et al *Neurobiol Aging.* 2011). Chondroitinase ABC (ChABC) (Sigma-Aldrich) or nitrous acid treatments were used to selectively quantify HS or CS in total GAG samples (Huynh et al 2011). A calibration curve constructed with known amounts of CS standard was included in each assay. The extraction and quantification method was validated in GAGs spiked rodent brain samples as previously described (Huynh et al, *Neurobiol Aging.* 2011).

GAGs Isolation (Heparan Sulfates and Chondroitin Sulfate) Extraction and Quantification from Brain and CSF GAGs were isolated as follows: PK/DNAse digested samples were reached to 4 M NaCl final sample concentration and vigorously agitated during 10 min. Proteins were precipitated with TCA treatment (10% final concentration) and supernatants were then cleared by chloroform washing followed by rapid dialysis of the aqueous phase (Slide-A-Lyzer Mini Dialysis Units 3,500 MWCO, Pierce) against the extraction buffer and then pure water. After freeze drying, material was dissolved in water or in a glycanases digestion buffer (10 mM sodium acetate, 2 mM $CaCl_2$, pH 7), as required. GAGs were then quantified by following the DMMB protocol. Identities and specific recovery of extracted HS or CS were performed by specific digestion with chondroitinase ABC (ChABC) for HS recovery, or by heparinases I/II/III or by nitrous acid treatment for CS recovery as previously described (Huynh et at, *Neurobiol Aging.* 2011).

Brain and CSF HS Disaccharide Analysis by LC/MS

Extracted and freeze dried GAGs samples from brain and CSF dissolved in the glycanases digestion buffer (10 mM sodium acetate, 2 mM $CaCl_2$, pH 7) were simultaneously digested with heparinase I, II, and III cocktail (0.25 mU each, 24 h, 37° C.). After filtration, samples were filtered and injected to LC/MS system composed of a LTQ/orbitrap coupled to a capillary liquid chromatographic system (LC). The used separation and detection method was that described in Methods Enzymol. 2011 ou par la method de Yang et al (Ultra-performance ion-pairing liquid chromatography with on-line electrospray ion trap mass spectrometry for heparin disaccharide analysis. Analytical Biochemistry 415 (2011) 59-66).

Example 6

GAGs from Alzheimer's Disease have Increased Tau Binding Capacities

GAGs from Alzheimer's disease and age-matched control hippocampus were tested for their capacities to bind Tau protein by using the ELISA competition binding assay as described below. FIG. 6A shows a significant increase in the ability of Tau to bind Alzheimer's disease GAGs. This effect was already observed for 0.1 ng/mL GAG. Evaluation of the effective concentration necessary to obtain 50% of Tau binding to polysaccharides (EC50) showed to be decreased on Alzheimer's disease GAGs compared to controls (FIG. 6B) meaning an increase in GAG affinity for Tau in case of disease. These results suggest that, with Alzheimer's disease, GAGs composition changes in hippocampus resulting in more binding of these GAGs to Tau.

Heparin/Glycosaminoglycans Competition Assay Towards Human Tau Protein:

AD and control hippocampus extracted GAGs binding to human Tau protein (R&D systems) was evaluated by an ELISA based competition binding essay (Najjam et al., 1997). ELISA type 96 wells plates were coated with a 2 μg/mL BSA-heparin conjugate solution prepared as previously described (Najjam et al., 1997). After washing with PBS/0.05% Tween-20 (washing solution), wells were saturated with 3% BSA in PBS. Then, the assayed protein (in PBS) was added to the plate in a concentration dependent manner in order to determine the protein concentration giving 50% of binding to immobilized heparin ($ED_{50}$). From this data, tau protein doses used on the competition assay were fixed at 100 ng/mL. This tau concentration was used to examine changes on the Tau binding extents to immobilized heparin in the presence of soluble competing extracted GAGs (0, 0.01, 0.1, 0.5, 1 10, 100, and 500 ng/mL). Control and AD GAGs, and tau protein were simultaneously added to heparin immobilized wells and plates were incubated 1 h at rt. After washing, the protein remaining bond to the plate was targeted by a corresponding specific antibody (1:1000, 1 h, rt) followed by a peroxidase-labeled secondary antibody (1:5000, 1 h, rt). Peroxidase activity was measured by the tetramethylbenzidine (TMB) detection kit (Pierce). Reference binding (100%) was assigned to signal left when aged group GAGs were used (FIG. 21).

Example 7

Phosphorylation of Human Tau by Brain GSK-3 Kinases in the Presence of Control and AD GAGs or 3-O-Sulfated or not HS Oligosaccharides Phosphorylation by glycogen synthase kinase 3 (GSK-3). Recombinant hTau41 (Millipore) was incubated for 0 to 24 h with 1 unit/ml of recombinant GSK3 (Millipore) in the presence or absence of 50 mg/ml of heparin, Arixtra®, or the heparin hexasaccharide non 3-O-sulfated. Phosphorylation assays (0.050 ml) were carried out at 30° C. and comprised 25 mM Tris-HCl, pH 7.4, 0.1 mM EGTA, 0.1 mM sodium orthovanadate, 2.5 mM PKI (a specific inhibitor of cyclic AMP-dependent protein kinase), protease inhibitors (0.5 mM phenylmethylsulfonyl fluoride, 5 mg/ml aprotinin, 5 mg/ml leupeptin, and 0.5 mg/ml pepstatin), tau protein (4 mM), 10 mM magnesium acetate, 2 mM [g-$^{32}$P]ATP (approximately 100 cpm/nmol) 5 units/ml recombinant reconstituted GSK3. Reactions were initiated with ATP and aliquots were removed at various times ranging from 10 min to 24 h and used for SDS-polyacrylamide gel electrophoresis and immunoblotting. Immunoblots were performed as described (Masato Hasegawa et al., J Bio Chem. (1997) 272 (52), pp. 33118-33124). Alternatively, incorporation of $^{32}$P radioactivity was measured after adsorption to Whatman P-81 paper, as described. Heparin and extracted GAGs were included in the assays at 50 mg/ml.

Example 8

Suppression of Glycosaminoglycans Sulfation in a Mutational-Dependent (hTauP301L) and in a Mutational Independent (Oxidative Stress) Cell Model of AD with Tau Hyperphosphorylation Two cell types were used, (i) a wild type SH-SY5Y cells (mutation-independent model) in where abnormal phosphorylation is induced by oxidative stress and (ii) cells stably transfected with complete human tau protein having the mutation hTAU-P301L (mutation dependent model), characteristic of FTDP-17. As a consequence of the Tau mutation cells present high levels of abnormal phosphorylated Tau.

For the mutation dependent model cells were cultured as previously described (Schaeffer V et al., J Neurobiol 2006, July; 66(8):868-881). For the mutation independent model, human SH-SY5Y neuroblastoma cells were propagated in Dulbeco's modied Eagle's medium (Gibco) with 5% fetal bovine serum and penicillin/streptomycin (5% $CO_2$ and 95% air). For both models cells were plated at a density of $10^6$ cells/cm$^2$ on 25 cm$^2$ dish and incubated under standard conditions for 24 h. Then, cells (both models) were treated with 10 µM retinoic acid (RA) for 3 days to induce their neural differentiation.

For the mutation independent models, differentiated cells were then treated with $H_2O_2$ (500 mM) for 30 min and medium was changed for fresh medium again supplemented with RA. This oxidative treatment induces abnormal tau phosphorylation in cells at Thr231 and Ser396 of Tau.

Six hours after the oxidant elimination.

After 3 days of differentiation, cells from both models were treated with sodium chlorate, an inhibitor of GAGs sulfation, added at final 50 mM concentration in the presence of RA (10 µM) to maintain differentiation. Cells were incubated under these conditions for additional 24 h, then, cells were washed, harvested and used for pTau flow cytometry and western blot analysis with anti-tau-pSer199 and anti-tau-pSer396 antibodies (Millipore).

Example 9

Silencing of 3-OST-2 (HS3ST2) in a Mutational-dependent (hTauP301L) and in a Mutational Independent (Oxidative Stress) Cell Model of AD with Tau Hyperphosphorylation Effect of HS3ST2 and HS3ST4 siRNA silencing was tested in the two described cell models of AD but chlorate treatment was replaced by a siRNA set forth by SEQ ID NO 73 for the sense and 74 for the antisense (10, 20, 40 and 80 nM) transfection with lipofectamine. In all cases cells were plated and incubated under standard conditions to 60% of confluence, siRNA silencing was directly performed in hTauP301L cells and before and after $H_2O_2$ stress for WT cells. Optionally, silenced cells and controls were differentiated with retinoic acid (10 µM) for 3 days. Harvested cells were analyzed by flow cytometry using antibodies anti-tau-pSer199 and anti-tau-pSer396 (Millipore) using well known techniques. At least 10000 cells (events) were analyzed by point. HS3ST2 silencing was confirmed by RTqPCR of HS3ST2 transcripts analysis and by western blot for HS3ST2 protein expression.

Western Blot Analysis.

After harvesting, cells were and incubated in an ice bath for 5 min in a lysis buffer (50 mM Trus-HCl, 150 mM NaCl, 1% Triton X-100, 1 mM EDTA, 10 mM NaF, pH 8.0) containing 1 mM $Na_3VO_4$, and 0.1% protease inhibitor cocktail (Sigam). Lysates were centrifuged and proteins in the supernatants were quantified using the BCA protein assay kit (Pierce). Extracts corresponding to 30 µg of proteins electrophoretically separated as described for tissue and CSF protein samples. Abnormally phosphorylated tau was detected by using anti-tau-pSer199 and anti-tau-pSer396 (Millipore) as described above. For analysis of the HS3ST2, previous immunoprecipitation (milteni kit) of the enzyme was required for improving detection in cultured cells. To evaluate protein loading, membranes were immediately stripped and reprobed for β-actine. Results were expressed as a ratio of target protein to actine. Independent experiments were normalized to controls.

Example 10

Analysis of Hyperphosphorylation of Tau Protein in Zebrafish

In order to study the expression of 3-OSTs on mutated hyperphosphorylated Tau protein levels, we used a zebrafish transgenic line of hTau-P301L that shows the characteristic features of Taupathies including neuronal loss, Tau hyperphosphorylation, aggregation, tangles formation, and behavior alterations (Paquet et al., 2009). Brains of 5 day old hTau-P301L transgenic embryos were first labeled with antibodies against hyperphosphorylated Tau protein to assess whether the sites of hyperphosphorylation, indicative of Taupathies, were present. As expected we observed a hyperphosphorylation of Tau in the hTau-P301L mutated (FIG. 10A); compared to wild type which showed no Tau hyperphosphorylation at all. Additionally, the hyperphosphorylated Tau was not only localized on cerebellum and on the upper region of the spinal cord, but it was also highly expressed in the telencephalon of the mutant, suggesting that the forebrain may extremely be affected by the misfolding of Tau.

Abnormal phosphorylation is classically expressed as the ratio of abnormal phosphorylated Tau levels compared to total Tau protein levels analyzed in a same sample. In the transgenic zebrafish, the level of abnormal phosphorylated Tau/total Tau protein was determined by the P-Tau and T-Tau ELISA assays, as described below. A 90 fold increase in abnormally hyperphosphorylated Tau protein accumulation by the amount of total Tau protein was observed in transgenic hTAU-P301L compared to WT (FIG. 10B). Additionally, to determine if Aβ42 was present in these fishes, Aβ42 ELISA analyzes were performed. As expected, no Aβ42 was observed in this transgenic hTAU-P301L model of FTD.

Transgenic hTAU-P301L embryos with morpholino-mediated knock-down of the 3-OST-2 coding gene with SEQ ID NO: 5 and the non-injected embryos were screened on the intensity of DsRed fluorescent protein at 24 hpf. With morpholino-mediated knock-down of the 3-OST-2 coding gene in the transgenic hTAU-P301L zebrafish model the level of hyperphosphorylation in Tau protein was investigated. First of all, the obtained zebrafish embryos from the crossing between WT line and transgenic zebrafish carrying the P301L mutation in Tau protein were injected with different morpholino concentrations, respectively 0.3 mM, 0.5 mM and 1 mM. The numbers of living embryos were assessed at 24 hours after injection and survival rates were determined. We observed that the morpholino concentration of 0.5 mM did not give major anomalies or deformities and the rate of survival among morphants was optimal (67% survival rate at 24 hours post-injection). Thus, this concentration was chosen for further analyses (FIG. 12).

Transgenic Zebrafish:

The transgenic line expressing hTAU-P301L was kindly provided by Professor Christian Haas (Paquet et al., 2009). The animals were raised as described. Briefly, Mosaic DsRed-positive larvae were raised and out-crossed with wild-type fish. Zebrafish were maintained at 28° C. under standard conditions as described by Westerfield (1995). Developmental stages were determined as hours of post fertilization (hpf) as described by Kimmel et al. (1995). All experiments were performed in accordance with ethical policies for the care and use of laboratory vertebrate animals (Direction départementale des services veterinaries de Paris).

Total RNA Extraction from Zebrafish and qPCR

Total RNA was extracted from a pool of 100 dissected embryos of both WT and DsRed-positive zebrafish samples. The RNA extraction was accomplished by using the RNAeasy® minikit (50). To determine the HS3ST2 expressions at the mRNA level, cDNA was synthesized from the isolated RNA by a reverse transcriptase reaction. Briefly, total extracted RNA (1 μg) was incubated with random primers (30 μg/mL) in a mixture of 5 mM dNTP's and RNase inhibitor (Invitrogen) for 5 min at 65° C. Followed by an incubation with respectively 5× first strand buffer, 1 mM DTT and RNase inhibitor Superscript II Rnase H— Reverse Transcriptase (Invitrogen) at 42° C. for 52 min and 15 at 70° C. A mixture with except the transcriptase was served as a negative control. For qPCR, primers were designed by Primer3output and obtained by Eurofins (Gemany) (Table 4). For qPCR, amplifications were performed on the Light-Cycler (Software version 3.5; Roche Switserland) with FastSart DNA Master SYBR Green I (Roche, Switzerland) used following the standard operating procedures provided by manufacturer. All samples were amplified simultaneously in one assay run. Relative quantification was performed as described above (Vandesompele et al., 2002, Accurate normalization of real-time quantitative RT-PCR data by geometric averaging of multiple internal control genes. Genome Biol 3:RESEARCH0034).

TABLE 4

Human and zebrafish (Danio rerio) 3-OST primers

| | Enzymes | Accession number | Oligonucleotide sequences sense | Oligonucleotide sequences anti-sense |
| --- | --- | --- | --- | --- |
| Human | 3-OST-1 | NM_005114 | ACCACATGCAGAAGCACAAG (SEQ ID NO: 33) | TTGAGGGCCTTGTAGTCCAC (SEQ ID NO: 34) |
| | 3-OST-2 | NM_006043 | GGAACCCCACTTCTTTGACA (SEQ ID NO: 7) | GTCGAGGAGCCTCTTGAGTG (SEQ ID NO: 8) |
| | 3-OST-3a1 | NM_006042 | ACGCCCAGTTACTTCGTCAC (SEQ ID NO: 35) | GAACGTCAAGCTCTCGAAGG (SEQ ID NO: 36) |
| | 3-OST-3b1 | NM_006041 | ACGCCCAGTTACTTCGTCAC (SEQ ID NO: 37) | TCTGCGTGTAGTCCGAGATG (SEQ ID NO: 38) |
| | 3-OST-4 | NM_006040 | AAGAGCAAAGGTCGGACTCA (SEQ ID NO: 9) | ACCCTCTTCCTGTTCCCACT (SEQ ID NO: 10) |
| | 3-OST-5 | NM_153612.3 | GCTAGAGGGGAAGGAGAGGA (SEQ ID NO: 39) | CCATCGACGACATGAAATTG (SEQ ID NO: 40) |
| | GAPDH | NM_002046.3 | CCGTCTAGAAAAACCTGCC (SEQ ID NO: 47) | GCCAAATTCGTTGTCATACC (SEQ ID NO: 48) |
| | A-tubulin | NM_006009.2 | GCAACAACCTCTCCTCTTCG (SEQ ID NO: 43) | GAATCATCTCCTCCCCCAAT (SEQ ID NO: 44) |
| | TFIID | NM_003194.4 | TGCACAGGAGCCAAGAGTGAA (SEQ ID NO: 45) | CACATCACAGCTCCCCACCA (SEQ ID NO: 46) |
| Danio rerio | 3-OST-1 | NM_001080593.1 | CGGTGTCTGCACAGCTCTAA (SEQ ID NO: 49) | CGACCAGCTCAAAGAACCTC (SEQ ID NO: 50) |
| | 3-OST-2 | NM_001080608 | CTCCAGTACTTCCGGCTGTC (SEQ ID NO: 51) | CTGCTGCTCTCTGGCTTCTT (SEQ ID NO: 52) |
| | 3-OST-3X | DQ812987.1 | CAGGGAACTAATGCCCAAAA (SEQ ID NO: 53) | TCTCGCACCACGACTATCAG (SEQ ID NO: 54) |
| | 3-OST-3Z | DQ812988 | GAAGAAACTCGGGCTCCTCT (SEQ ID NO: 55) | CGTCTCCTTCGCTCGATTAC (SEQ ID NO: 56) |
| | 3-OST-4 | NM_001080589 | GCTCTTCACCTGGAAAGCTG (SEQ ID NO: 57) | AATCCTGCACTTTTGCCATC (SEQ ID NO: 58) |
| | 3-OST-5 | NM_001039926.1 | ACTTTCGGAAGGGTCTGGAT (SEQ ID NO: 59) | GGTGGAGCTGTGAAGTAGCC (SEQ ID NO: 60) |
| | 3-OST-6 | DQ812991 | CACCTGCATCTCCATCCTCT (SEQ ID NO: 61) | CTCTCGGCCTGAACTATTGC (SEQ ID NO: 62) |
| | 3-OST-7 | DQ812992 | AAACACCGGGGTATTTCACA (SEQ ID NO: 63) | TCTTCACCAGCATGTTCTCG (SEQ ID NO: 64) |
| | gapdh | NM_001115114 | GATACACGGAGCACCAGGTT (SEQ ID NO: 65) | GCCATCAGGTCACATACACG (SEQ ID NO: 66) |

TABLE 4-continued

Human and zebrafish (Danio rerio) 3-OST primers

| Enzymes | Accession number | Oligonucleotide sequences sense | Oligonucleotide sequences anti-sense |
|---|---|---|---|
| bactin1 | NM_131031 | CTCTTCCAGCCTTCCTTCCT (SEQ ID NO: 67) | CTTCTGCATACGGTCAGCAA (SEQ ID NO: 68) |
| tbp | NM_200096 | GAGCAACAGAGGCAACAACA (SEQ ID NO: 69) | GATAGGCGTCATAGGGGTGA (SEQ ID NO: 70) |

Morpholino-mediated Knockdown of the HS3ST2 Coding Gene in the Transgenic Zebrafish Line Expressing hTAU-P301L Morpholino oligonucleotides (MO) were designed to target the flanking region in the zebrafish 3-OST-2 gene in order to block the translation of the HS3ST2 mRNA: 5'-ATGGCATATAGGT TCCTGTCAAGCC . . . -3'. The morpholino antisense oligonucleotides were designed by Gene Tools (LLC One Summerton Way, Philomath, Oreg., USA). MO HS3ST2-ATG: 5'-GGCTTGACAGGAAC-CTATATGCCAT-3'.

Morpholino Injection.

The morpholinos were diluted to three different concentrations in Danieau buffer (58 mM NaCl, 0.7 mM KCl, 0.4 mM MgSO4, 0.6 mM Ca(NO$_3$), 5 mM HEPES pH 7.6) and co-injected with 0.3 mg/mL dextran rhodamine (Molecular Probes, Eugene, Oreg., USA). Transgenic zebrafish embryos at one-cell or two-cell stage were microinjected with approximately 2 nL of 0.5 mM, or 1 mM morpholino solution using a pressure microinjector and a Zeiss stereomicroscope (Zeiss). The three morpholino solutions were tested for fish viability, anomalies and deformities. Only viable concentrations that did not caused any major anomalies or deformities were used (0.5 mM). Embryos were maintained at 28° C. in fish water. After 20 hpf, embryos were incubated with 1×PTU (1-phenyl 2-thiourea), an inhibitor of all tyrosinase-dependent steps in the melanin pathway. The second day, after dechorionation, the DsRed-positive embryos were selected: only embryos showing a significant red fluorescent labeling, characteristic of mutated fish, were considered positive in the presence of the morpholino. Embryos were then fixed or dissected at 48, and 120 hpf.

Analysis of Hyperphosphorylation Tau Protein in Zebrafish by Immunocytochemistry Zebrafish embryos were anaesthetized with 0.64 mM tricaine (Sigma-Aldrich, St. Louis, Mo., USA) and fixed in 4% paraformaldehyde for 1 hour at rt. 5 dpf embryos were fixed for 1 hour before brains were dissected in PBS. After 6 times washing with phosphate buffer for 5 minutes each, the dissected brains or whole embryos were blocked and permeabilized with 0.2% gelatin (Merck, Darmstadt, Germany) and 0.25% Triton X100 (Sigma-Aldrich, St. Louis, Mo., USA) for 1 hour at rt, followed by incubation of the primary antibodies anti-PHF-Tau antibody clone AT8 (Thermo Scientific) and anti-PHF-Tau antibody clones AT180 (Thermo Scientific) diluted at 1:100 in the buffer containing 0.02% NaN$_3$. Also anti-DsRed (Clontech) was labeled, diluted at 1:50 in order to select positive DsRed embryos. After, brains or embryos were incubated with the solution of goat anti-mouse biotinylated antibody (Vector, 1:400 dilution) for 1 h30 min at rt, followed by an incubation for 1 hour at rt in a solution of Steptavidine Alexa 488 (Molecular probes, used at 1:400 dilution). Brains or embryos were mounted with 1% of agarose (low melting, Biorad) in PBS buffer. Images of morphant phenotype were captured under bright-field illumination using a stereomicroscope (SteREO Lumar. V12, Zeiss) equipped with a digital camera (DXM 1200F, Nikon) controlled by the ACT-1 software (Version 2.63 Nikon). Combination of fluorescent labelings was imaged using a microscope equipped with an ApoTome system (Zeiss) equipped with an AxioCam MRm camera (Zeiss) controlled by the Axiovision software.

Protein Extraction from Zebrafish and Tau Quantification by ELISA

The embryos resulting from crossing between AB line and transgenic zebrafish carrying the P301L mutated Tau gene were screened for the DsRed fluorescent protein at 24 hpf and at 48 hpf the vitellus was removed. A double volume of ice-cold extraction buffer containing 50 mM Tris HCl pH 8, 150 mM NaCl, 10% Triton X100, 1 mM EDTA, protease inhibitor (cocktail Roche), 10 mM NaF and 1 mM sodium orthovanadate was added to the embryos. Tissues were fragmented by sonication (Branson, Sonifier 250) and homogenized at 4° C. (Stuart rotator SB3). After 30 minutes of centrifugation at 10 000 rpm (Eppendorf Centrifuge, Sigma-202 MK) supernatant was decanted. Protein concentration was measured according to the Bradford method.

Abnormally phosphorylated Tau (P-Tau) was determined with the INNOTEST™ PHOSPHO-TAU (181P) ELISA (Innogenetics, Gent Belgium). Levels of P-Tau181, characteristic of taupathy associated pathologies, were measured using a combination of monoclonal antibody HT7 (which recognizes amino acids 159-163 in normal Tau and P-Tau) and biotinylated monoclonal antibody AT270 (which recognizes P-Tau containing the phosphorylated threonine 181 residue). A synthetic phosphopeptide, furnished in the ELISA INNOTEST, was used for standardization.

Total Tau (T-tau) was measured by INNOTEST hTAU-Ag ELISA, (Innogenetics, Gent, Belgium). The T-Tau assay utilizes monoclonal antibody (AT120) for capture and biotinylated monoclonal antibodies (HT7 and BT2) for detection (Vanmechelen et al., 2000). Also Aβ42, were determined by INNOTEST™ β-Amyloid (1-42) ELISA, (Innogenetics, Gent, Belgium).

Example 11

Heparan Mimetic Synthesis (F6 and CR36) Inhibits Tau Hyperphosphorylation in Brain of SAMP8 Mice The general synthesis procedure is disclosed below:

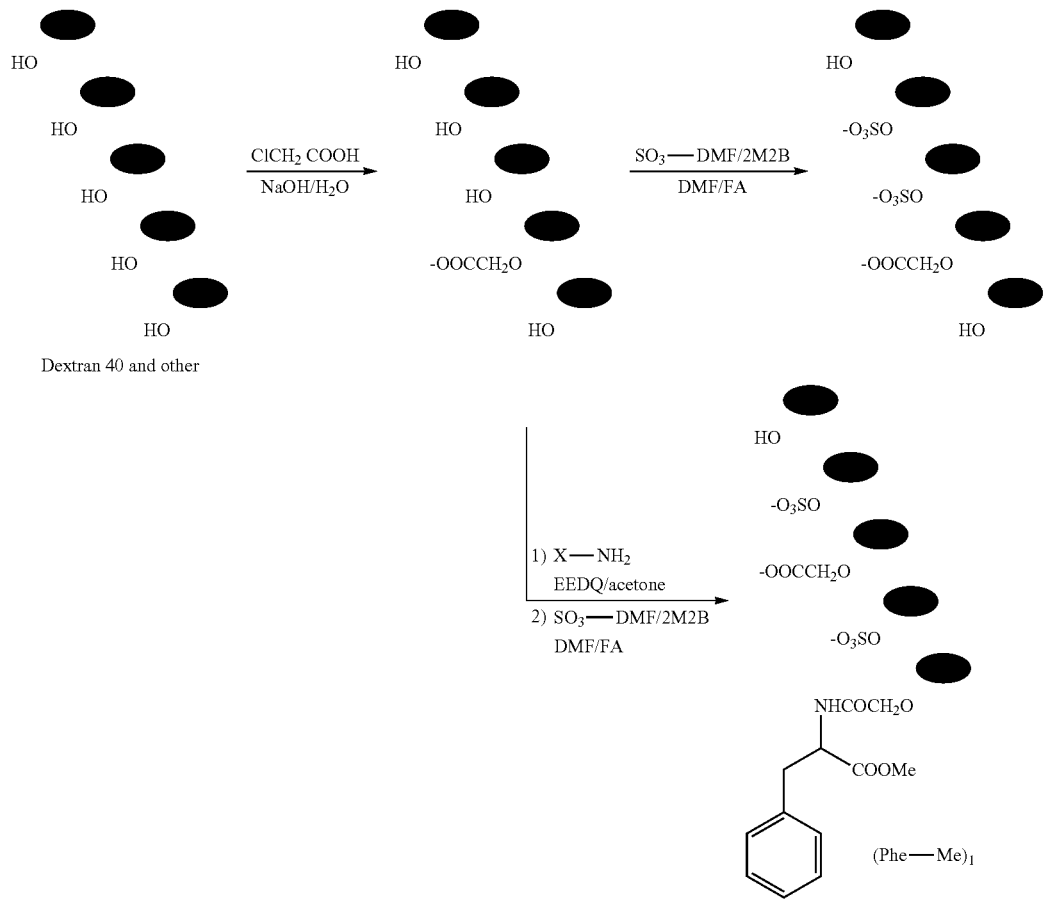

Dextran 40 and other (Phe—Me)₁

XNH₂ = n-octylamine
  t-octylamine
  Ethylhexylamine
  Phenylalanine methyl ester 2M2B: 2-methyl-2-butene
EEDQ: 2-ethoxy-1-ethoxycarbonyl-1,2-di-hydroxyquinoleine
DMF: dimethylformamide
FA: Formamide

| HMs[a] (ref. NMR) | Structural characteristics | | | |
|---|---|---|---|---|
| | N glu[b] (dp) | dsS[c] (NMR) | dsCM[d] free | X(NH₂)[e](PheOMe) |
| HM-oligo.CM$_L$-S$_L$-X$_L$ (B) | 6 to 15 | 0.22 Low | Low | Low |
| HM-oligo.CM$_M$-S$_L$-X$_H$ (C) | 6 to 15 | 0.17 Low | High | High |
| HM-oligo.CM$_M$-S$_{ML}$-X$_H$ (D) | 6 to 15 | 0.60 Medium | Low | High |
| HM-oligo.CM$_H$-S$_L$-X$_H$ (E) | 6 to 15 | 0.20 Low | Medium | High |
| HM-oligo.CM$_{ML}$-S$_M$-X$_H$ (F) | 6 to 15 | 0.88 Medium | Medium | High |

[a]L: Low, M: Medium, H: High
[b]Polymerization degree, determined by size exclusion chromatographié
[c]sulfatation degree (dsS), determined by NMR dosage with DMMB
[d]carboxymethylation level, estimated by ¹H NMR
[e]Amidation level with Phenylalanine methyl ester (PheOMe), estimated by ¹H NMR Heparan mimetics (HM) used in the present invention are dextran derivatives also known as RGTAs (for ReGeneraTing Agents) because of their tissue regenerative properties. These compounds have the general formula AaXxYy, in where A represents a monomer, including a glucose unit, X represents a RCOOR' moiety, including a carboxymethyl moiety, Y represents an O- or N-sulfonate moiety covalently linked to A and having one of next formulas: —$ROSO_3R'$, —$RNSO_3R'$ in where: R represents an alkyl chain with possible aromatic substitutions, including amino acid substitution, and R' represents an hydrogen atom or a cation. a represent monomers number, x represents the substitution degree of the X moieties linked to monomer A, and y represents the substitution degree of Y groups on monomer A. CR36, F6, and other molecules responding to this definition are prepared as reported in previous patents. However, the synthesis and structure characterization of the compounds used in this invention is as specified below. The difference between the F6 and the CR36 synthesis is the starting dextran used in their synthesis, carboxymethylation, amidation and sulfations reactions are the same.

Carboxymethylation of Dextran:

For F6, a dextran T5 (MW=5000 Da) was used as starting material. For CR36, a dextran T10 (MW=10000 Da) was used as starting material. Dextran (30 g, 0.185 mol of glucose) was dissolved in 146 mL of water, and separately, 59.2 g of NaOH (1.4 mol) was dissolved in 59 mL of water. Both solutions were cooled to 4° C. The NaOH solution was slowly poured into the dextran solution under stirring and controlling temperature not to exceed 15° C. The reaction mixture was stirred for 20 min and then allowed to cool at 4° C. Monochloroacetic acid (61.3 g, 6.5 mol) was added in small portions with controlling reaction temperature <20° C., and then the reaction mixture was stirred at 50° C. during 40 min. The reaction was then quenched by purified by tangential ultrafiltration of the resulting aqueous solution using a 1000 molecular weight cutoff membrane, followed by freeze-drying as described. For preparation of products with higher carboxymethyl content the same procedure was repeated two or three times in order to obtained desired dsCM.

D6, D4 and E5 are synthesized in a similar way.

Amidation Reactions.

CMD (5 g, dsCM) 1.1, 21.5 mmol of $COO^-$) was dissolved in 136 mL of water, and then 71 mL of acetone was added. The temperature was kept at 40° C. To activate the carboxylic functions, 5.3 g of 2-ethoxy-1-ethoxycarbonyl-1,2-dihydroquinoline (21.5 mmol) in 20 mL of acetone was added, and the reaction mixture was stirred for 20 min at 40° C. The final solvent was composed by a ratio 60/40 water and acetone. Then, phenyalanine methyl ester (21.5 mmol) was added and the pH was adjusted to 7 by HCl 4 M. The reaction was stirred at 40° C. overnight. The final product was purified by tangential ultrafiltration of the resulting aqueous solution followed by freeze-drying.

$SO_3$-DMF Mediated Synthesis of Sulfated Polysaccharides in the Presence of 2M2B.

An aqueous 10 g/L solution of CMDPh (24.3 mmol of glucose) was dissolved in 40 mL of formamide and 160 mL of DMF. After complete dissolution, 40 mL of 2M2B (26.5 g, 378.6 mmol) was slowly added. A $SO_3$-DMF complex (7.4 g, 48.6 mmol) was rapidly added, and the reaction mixture was stirred at 30° C. for 2 h. The reaction was quenched by slowly pouring it into 200 mL of $NaHCO_3$ and the final product was purified by tangential ultrafiltration followed by freeze drying as described above. Amidated products were not protonated before sulfation.

Product Purification and Structure Characterization.

Product purification was systematically achieved by tangential ultrafiltration on a 1000 normal-molecular-weight cutoff (NMWCO) regenerated cellulose membrane (Pellicon2, 0.5 $m^2$, Millipore, Mass.) against 5 L of NaCl 1 M and then 20 L of Milli-Q water. The resulting concentrated solution was freezedried. Pure dry products were homogenized to obtain a fine powder by a Universal mill A10 IKA (IKA-WERKE GMBH & CO. KG, Germany). 1H NMR spectra were recorded with a 200 MHz Bruker spectrometer and with a 600 MHz Varian spectrometer from samples in D2O using residual H2O peak as a standard (4.805 ppm). Absolute determination of molecular weights and size distributions were performed on polysaccharide solutions by a size exclusion chromatography (SEC) eluted in 0.1 M $LiNO_3$ coupled to a multiangle laser lightscattering photometer (MALLS; Dawn DSP-F, Wyatt Technology, Santa Barbara, Calif.) connected in series to a differential refractive index detector (RI, ERC 7515A, Erma Cr. Inc., France). An TSK Gel G3000 PWXL (TosoHaas, Cambridge, U.K.) column was used for polysaccharide analysis. Degrees of substitution (ds), defined as the number of substituted carboxymethyl (dsCM), carboxymethyl amide (dsX), and sulfate (dsS) groups.

F6: 0.61 CM, 0.15 L-Phe(OMe), 0.7S wherein CM corresponds to the carboxymethyl groups (61% from possible 20 to 150% contents), S corresponds to the sulfate groups (70% from possible 20-150% contents); L-Phe(OMe) is present at 15% from possible 0-50% substitutions.

CR 36: Prepared from T10, NHX=L-Phe(OMe)) having the following degree of substitution:

59 CM, 22 L-Phe(OMe), 83S.

wherein CM corresponds to the carboxymethyl groups (59% from possible 20 to 150% contents), S corresponds to the sulfate groups (83% from possible 20-150% contents); L-Phe(OMe) is present at 22% from possible 0-50% substitutions.

Treatment of SAMP8 Mice with F6

A total of 60 5-month-old male SAMP8 and 14 5-month-old SAMR1 (normal control) were fed in clean grade animal houses at 22-24 with the humidity of 55±5% throughout 12 h light-dark cycle, all mice were fed with standard diet. The mean life spans of SAMP8 and SAMR1 were 15±2 and 30±3 months respectively. All mice were adaptively fed for five days, and then 60 SAMP8 mice were divided into six groups according to their weights, with 15 mice in each group: model group, Huperzine A group, F6 high-dose group (F6 H, 50 mg/kg), and F6 low-dose group (F6 L, 50 mg/kg). Huperzine A group was orally administered with 3.86 µg/Kg Huperzine A (equivalent to clinical the dose of people, dissolved in normal sodium) once a day; F6 H group was intraperitoneally injected 50 mg·Kg-1 F6 (dissolved in normal sodium) once every four days; F6 L group was intraperitoneally injected 25 mg·Kg-1 F6 (dissolved in normal sodium) once every four days; the model group and SAMR1 normal control group (control) were orally administered with equivalent dose solute (200 µL purified water) once a day. All groups were treated for 2 months before perform behavior and molecular biology detection.

Behavior and Molecular Biology Detection:

Determination of the effect of GAGs analogues on the learning and memory ability of SAM Behaviours detections were performed in order: place navigation (day 1-4), spatial probe test (day 5) and foot shock avoidance test (day 8-9). Place navigation Morris water maze (MWM) detection was performed referring to reported literature with minor modifications (reference). The escape latency, swimming distance, residence time in different quadrant, the length of swimming route in different quadrant, total length of swimming route, swimming speed, percentage of successful escape in each group were investigated. Before experiment, mice were first put onto the submerged platform for 15 s (adaptation phase), and then put into water faced to the pool wall in the first and third quadrant respectively. Mice freely swam in MWM for 90 s, and the residence time on the platform longer than 5 s was considered as successfully searching for platform, the time from entering into water to successfully searching for platform was served as the escape latency. If mice did not successfully got platform in 90 s, the escape latency were recorded as 90 s. The mean escape latency every day was calculated to evaluate the ability to acquire spatial memory. All mice were continuously trained for 4 days, and the percentage of mice successfully searching for platform (swim-out rate) in each group every day was calculated.

Spatial Probe Test.

The platform was removed on the day after finishing the place navigation (the fifth day). Each mouse freely swam from the third quadrant for 90 s. The number of annulus crossings (across the actual location where the platform had been located in place navigation determination), the swim distance rate and time rate in the same platform (the percentage of swim distance or time in the platform of the third quadrant compared to total swim distance or time for mice) within 90 s were recorded to evaluate the ability to acquire spatial memory.

Foot Shock Avoidance.

Mice were performed foot shock avoidance test two days after finishing MWM test. The jumping apparatus was square and had eight rooms, with charged copper reticulum in the bottom of each room, its voltage could be controlled and regulated by computer, and a voltage of 40 V was used in this experiment. In the bottom of each room, an insulated circular platform with 5 cm diameter was put in the same side, fenders were put in the surrounding, the top side faced to the observer was transparent, and the other sides were non-transparent. The top of the room was moveable and could put into and take out of mice. Mice could stand in the insulated platform to avoid electric shock. The experiment had two phases: memory acquisition and memory consolidation.

Experiment of Memory Acquisition.

mice were put into room for 2 min to be familiar with the environment, and then put on the copper reticulum at the beginning of the experiment and switched on (40 V) for 5 min. The latency of mice escaping onto the insulated platform for the first time after electric shock, time on platform within 5 min (time in safe area), time underwent electric shock (time in wrong area), times of electric shock and frequency of mice underwent electric shock were recorded as the learning performance to judge the ability of passive avoidance response.

Experiment of Memory Consolidation.

mice were put onto platform to switch on for 5 min the next day after finishing the experiment of memory acquisition, the time when mice jumped down the platform into copper reticulum for the first time (latency), time in safe area (platform), time in wrong area (copper reticulum), frequency of electric shock and numbers of mice underwent electric shock were recorded to evaluate the memory performance.

Western Blot.

After finishing foot shock avoidance test, ⅔ of mice were collected blood by enucleating eyeball and then sacrificed. The whole brain was taken out on ice and washed with pooled normal sodium to remove blood, and then the left and right cerebral cortex and hippocampal area were respectively separated and put into freezing tubes, and finally preserved in liquid nitrogen. The left hippocampal area and cerebral cortex of three mice in each group were weighed, 1 mL protein lysate [50 mM Tris-HCl (pH 8.0), 150 mM NaCl, 1% Trition X-100, 1 mM EDTA, 10 mM NaF, 1 mM $Na_3VO_4$, cocktail inhibitor 1%] were added into 20 mg grinned samples on ice for 30 min, and then centrifuged at 13,000 rpm for 15 min at 4° C., the supernatant was collected and preserved at −80° C. The protein content was determined by using BCA kit. A total of 30 μg proteins were collected to perform Western blot. After SDS-PAGE, protein was transferred onto PVDF membrane at 4° C. and blocked for 1 h with 3% BSA, then added with the primary antibody to incubate overnight at 4° C. Following primary antibody were used: Anti-Tau 1 (1:200), anti-Tau5 (1:500), anti-pTau199/202 (1:1,000), anti-pTau231 (1:1,000), anti-pTau404 (1:1,000). The fluorescence-labeled secondary antibody was added and incubated for 1 h in dark at room temperature. Odyssey infrared imaging system was finally used to scan and analyze bands.

Fluorescence Immunohistochemistry.

Sample processing. After finishing foot shock avoidance test, ⅓ mice were underwent endocardial perfusion with 0.1 M PBS for 5 min and 4% paraformaldehyde (0.1 M PBS, pH 7.4) for 10 min, when the liver and bowels of mice turned white and tail twitched, the whole brain was rapidly taken out and fixed with 4% paraformaldehyde for 24 h, and then put into 20% sucrose solution (in 0.1 M PBS, pH7.4) overnight at 4° C. And then went through dehydration procedures: 50% alcohol for 36 h, 70% alcohol for 48 h, 80% alcohol for 6 h, 95% alcohol for 4 h (×2), 100% alcohol for 3 h for (×3), dimethyl benzene for 1.5 h (×2), paraffin wax for 4 h (×2). Finally samples were performed with paraffin imbedding and serial sections with a thickness of 5 μM.

Fluorescent Staining:

the formal experiment of fluorescent staining was developed on the basis that no positive staining was observed in non-specific primary immunostaining and non-specific secondary immunostaining of each determined index.

Deparaffinage: dimethyl benzene for 5 min for three times, 100% alcohol for 3 min for twice, 95% alcohol for 1 min, 70% alcohol for 1 min, 50% alcohol for 1 min, washed with water for 5 min.

Antigen retrieval: citrate water bath at 100° C. for 20 min, washed with water for 10 min, washed with PBS for 5 min for once. Antigen blocking: blocked with 3% BSA for 30 min at room temperature. Endogenous biotin blocking: performed according to the instructions of the kit. Blocked with solution A and B for 15 min respectively. The primary antibody: diluted with 1% BSA+0.2% Triton X-100+PBS and incubated overnight at 4° C. Anti Tau 5 (1:100), anti pTau199/202 (1:100), anti pTau231 (1:100), anti pTau262 (1:200), anti pTau396 (1:100), anti CS (1:100), anti cathepsin D (1:100), anti cathepsin B (1:50), anti HS (A04B08) (1:20). The secondary antibody: diluted with 1% BSA+0.2% Triton X-100+PBS (1:200) and incubated for 1 h at room temperature in dark place. HS was referred to reported literature (Ottenheijm et al., 2007), anti-VSV was diluted (1:5) and incubated for 1 h at room temperature and then performed staining.

Signal amplification: performed according to the instructions of the kit, two drips of solution A and B were respectively added into 10 mL PBS and incubated for 30 min at room temperature in dark place. Coloration: a drip of levamisole solution and two drips of solution A, B and C in the kit were respectively added into 5 ml Tris-Hcl (0.1 M, pH 8.2) and incubated for 20 min at room temperature in dark place. DAPI staining: used 1 µg·ml-1 DAPI to stain for 3 min at room temperature. Mounting and preserved at 4° C. in dark place. Taking pictures in time.

Example 12

F6 and CR36 Treatment on Aβ42 Neurotoxicity in Differentiated or Undifferentiated SH-SY5Y Cells F6 and CR36 were assayed on their capacities to modify Aβ42 toxicity in differentiated and in undifferentiated human SH-SY5Y cells (Datki et al., 2003). Undifferentiated SH-SY5Y cells were maintained at 37° C. and 5% $CO_2$ in DMEM supplemented with 10% FBS. For the assay, cells were seeded in 96 wells plates at 15 000 cells/well and maintained in DMEM supplemented with 10% FBS for 24 h. For the differentiated cells assay, medium was supplemented with 10 µM retinoic acid (Sigma-Aldrich) and cells were allowed to differentiate for 3 days. Retinoic acid treatment was not performed for the undifferentiated cells assay. Human Aβ42 peptide (Sigma-Aldrich) was extemporary aggregated in aqueous solution (50 µM) by gentle shaking at rt for 3 days. Aggregated Aβ42 was then added to the differentiated or undifferentiated cells at 10 µM final concentration. This Aβ42 peptide concentration was fixed by dose-effect experiments to obtain near 50% of cell viability (data not shown). F6, CR36, or control products (LiCl2, heparin, enoxaparin, DMMB) were added to cells at 0.01, 0.1 or 1 µg/mL final concentration with 10 µM of aggregated Aβ42 peptide and cells were incubated for 1 day. Cell viability was measured by the MTT assay (Mosmann, 1983). Briefly, medium was exchanged and 10 µL of a MTT stock solution (5 mg/mL) was added to each well. Cells were incubated for 2 h at rt and the MTT solution was discarded. DMSO was added to each well and optical density was read at 560 nm. Optical density was directly correlated to cell count by means of calibration curves for both, differentiated an undifferentiated cells (data not shown).

Example 12

Blood Brain Barrier (BBB) Passage

The Blood Brain Barrier (BBB) permeability studies were performed in BBB cells prepared as previously described (B. B. Weksler et al.; FASEB J. 2005 November; 19(13): 1872-4) in hCMEC/D3 cell monolayers. Briefly, permeability of BBB to molecules of different sizes was measured on Transwell polycarbonate insert filters. HCMEC/D3 cells were seeded on the filters at a confluent density of 2×105 cells/cm² in EGM-2 medium. After 48 h, assayed molecules including F6, CR36, HM2602 and Oligo-Dextran were added to the upper chamber, the lower chamber was sampled at 10-min intervals and the molecules that passed through the cell-covered inserts was determined using DMMB method for detection of sulfated saccharides (FIG. 22).

Data Analysis

Data analysis was performed by using Prism 5.0 (Graph-Pad Software Inc., CA) software, data were presented as mean±SEM. Paired comparison was performed by using two-sample t test and Mann-Whitney Test, multiple comparison was performed by using Oneway ANOVA.

CONCLUSION

In human Alzheimer hippocampus an increase of GAG binding affinity for Tau was observed. Furthermore in Alzheimer's disease a strong staining with co-localization of HS and hyperphosphorylated Tau was observed which was concentrated around the nuclei. These results showed that HS increased in content in Alzheimer disease. This increase in HS was accompanied with alterations in the structure and composition of HS and together with putative increase in 3-O-sulfation as detected by transcript over-expression. 3-O-sulfation is a HS biosynthetic modification characteristically found in heparin and carried out by 3-O-sulfotransferases (3-OSTs). HS modified by 3-OSTs could then play important roles in Alzheimer's disease. The expression of two 3-OST isoforms was markedly increased in Alzheimer's disease brains. Our results, reinforced by literature data indicating that Tau conformational changes induced by heparin can induce Tau hyperphosphorylation, suggest that this pathological signature of rare sulfation pattern in HS from Alzheimer's disease brains could be involved in pathology. The presence of transcripts corresponding to 3-OST was confirmed in the transgenic hTAU-P301L zebrafish model used in this study. This model is also characterized by abnormal hyperphosphorylation of Tau protein.

Here, it has been demonstrated in vivo that by decreasing the expression of 3-OST-2 by morpholino, accumulation of abnormal Tau hyperphosphorylation was markedly decreased. This strongly suggests an essential requirement for HS in the phosphorylation process. Particularly, HS structure and composition seams to require 3-O-sulfation for pathological Tau modification.

The decreased accumulation of hyperphosphorylated Tau after silencing of 3-OST-2 suggests that 3-O-sulfated HS stimulate interaction between Tau protein with kinases and/or phosphatases or that particular sulfated sequences of HS can regulate the affinity of Tau for kinases and/or phosphatases.

The changes induced in the structures of 3-O-sulfated HS present in Alzheimer disease, followed inhibition of 3-OST-2 may prevent a possible conformational Tau change that promotes microtubule disassembly and polymerization of the protein, this polymerization ends in the formation of insoluble PHFs, These changes might expose Tau to phosphatases, leading to lowered levels of phosphorylated Tau accumulation. Several evidences suggest that oligomeric forms of Tau might also have a role in disease pathogenesis, and dissolution of NFTs using drugs targeting Tau aggregation could conceivably result in increased amounts of available Tau oligomers. Thus, inhibition of 3-OST-2 protects cells from Tau abnormal phosphorylation, from microtubule disassembly and from PHFs formation.

The results of this study suggest the feasibility of targeting Tau phosphorylation by approaches other than inhibition of protein kinases or NFTs disaggregation strategies. The inhibitory effect of the 3-OST-2 morpholino on Tau phosphorylation in vivo, and/or the use of siRNA in cells, permit further studies on the mechanism of the inhibitory effect.

Example 13

Aβ Peptide Neurotoxicity Protection Assay

F6 or other HM were assayed on their capacities to modify Ab42 toxicity in differentiated and in undifferentiated human SH-SY5Y cells (Datki et al., 2003). Undifferentiated SH-SY5Y cells were maintained at 37° C. and 5% CO2 in DMEM supplemented with 10% FBS. For the assay, cells were seeded in 96 wells plates at 15 000 cells/well and maintained in DMEM supplemented with 10% FBS for 24 h. For the differentiated cells assay, medium was supplemented with 10 retinoic acid (Sigma-Aldrich) and cells were allowed to differentiate for 3 days. Retinoic acid treatment was not performed for the undifferentiated cells assay. Human Aβ25-35 peptide or Aβ42 peptide (Sigma-Aldrich), as indicated, was extemporary aggregated (50 μM) in aqueous solution by gentle shaking at rt for 3 days. Aggregated Aβ42 was then added to the differentiated or undifferentiated cells at 10 μM for Aβ42 or 25 μM for Aβ25-35 (final concentrations). The Aβ peptide concentration was fixed by dose-effect experiments to obtain near 50% of cell viability (data not shown). F6 or other molecules were added to cells at 1 or 10 μg/mL final concentration with the aggregated Aβ42 peptide and cells were incubated for 1 day. Cell viability was measured by the MTT assay (Mosmann, 1983). Briefly, medium was exchanged and 10 μL of a MTT stock solution (5 mg/mL) was added to each well. Cells were incubated for 2 h at rt and the MTT solution was discarded. DMSO was added to each well and optical density was read at 560 nm. Optical density was directly correlated to cell count by means of calibration curves for both, differentiated an undifferentiated cells (data not shown).

Western Blotting of Tau:

protein extracts (30 μg of protein) were blotted for detection of p-Tau using antibody Tau180 (commercially available at Thermo Fisher Scientific Inc. I 3747 N Meridian Rd, Rockford, Ill. USA 61101).

Structural features of the Heparan sulfate mimetics used in this study (example 13)

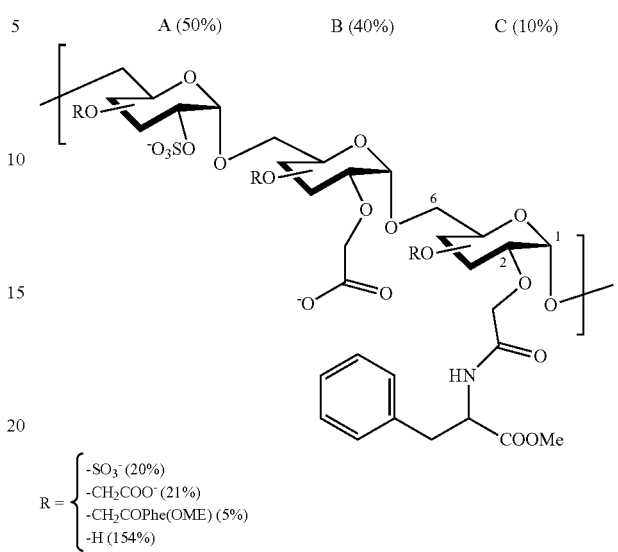

Structural Features of Anti-Tau HM

|  | Nombre of glu. (dp) | dsS | dsCM | ds hydrophobicity |
|---|---|---|---|---|
| Dextran (Dx) | ~250 | 0 | 0 | 0 |
| D4 | ~50 | 0.2 | 0.75 | 0 |
| E5 | ~50 | 1 | 0.5 | 0 |
| D6 | 8-15 | 1.2 | 0.6 | 0.2 |
| F6 | ~33 | 0.7 | 0.75 | 0.15 |

Results are presented FIGS. 25 to 29.

The invention claimed is:

1. A method for an in vitro screening for a modulator of the activity and/or level of a molecule selected from the group consisting of (1) a gene; (2) a transcription of a gene; (3) a translation product of a gene; (4) a fragment or derivative of (1), (2), or (3); (5) heparan sulfate; or a (6) Tau protein, the method comprising:
   a) contacting a sample of a biological fluid collected from a subject being subject to a Tauopathy, provided that said Tauopathy is different from a prion disease, with a test compound,
   b) determining the activity and/or level of at least one of the molecules (1)-(6) according to the following (i)-(vi) respectively for (1)-(6):
      i. for (1), at least one gene selected from the group consisting of the nucleotide sequences of SEQ ID NO: 1 and SEQ ID NO: 3 and coding for an heparin-glucosamine 3-O-sulfotransferase, and/ r
      ii. for (2), at least one transcription product of a gene selected from the group consisting of the nucleotide sequences of SEQ ID NO: 1 and SEQ ID NO: 3 and coding for an heparin-glucosamine 3-O-sulfotransferase,
      iii. for (3), at least one translation product of a gene selected from the group consisting of the nucleotide sequences of SEQ ID NO: 1 and SEQ ID NO: 3, said translation product being set forth respectively by SEQ ID NO: 2 and SEQ ID NO: 4,
      iv. for (4), a fragment or derivative of the gene of (i), the transcription product of (ii), or the translation product of (iii), v. for (5), 3-O-sulfated heparan sulfate, vi. for (6), abnormally phosphorylated Tau protein and/or total Tau protein, c) determining the activity and/or level determined in step b), i-vi, in a control sample of a biological fluid collected from a subject with a Tauopathy but not contacted with said test compound, d) comparing said activity and/or level determined in the contacted sample of biological fluid contacted with the test compound in step a) with the activity and/or level determined in the non-contacted sample of biological fluid not contacted with the test compound in step c), wherein an alteration in said activity and/or level of the contacted sample indicates that the test compound is a modulator of said i-vi, provided that the activity and/or the level determined in step b) is one of:

(i),
(ii),
(iii),
(iv),
(v),
both (v) and (iv) together,
(iv) and at least one of (i), (ii), and (iii), and
(v) and at least one of (i), (ii), and (iii).

2. The method according to claim 1, wherein the subject is a mammal, a human, a mouse, a SAMP8 mouse, a 3xTg-AD mice model of AD, or a Zebra fish.

3. The method according to claim 1, wherein said Tauopathy is Alzheimer's disease.

4. The method according to claim 1, wherein said the level of 3-O-sulfated heparan sulfate is the level of 3-O-sulfated heparan sulfate disaccharide.

* * * * *